(12) United States Patent
Masuo et al.

(10) Patent No.: US 7,925,340 B2
(45) Date of Patent: Apr. 12, 2011

(54) TRUNK VISCERAL FAT MEASURING METHOD AND APPARATUS, TRUNK SKELETAL MUSCLE AMOUNT MEASURING APPARATUS, TRUNK SUBCUTANEOUS FAT MEASURING METHOD AND APPARATUS, AND TRUNK VISCERAL AND SUBCUTANEOUS FAT MEASURING METHOD AND APPARATUS

(75) Inventors: Yoshihisa Masuo, Otsu (JP); Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 1371 days.

(21) Appl. No.: 11/402,995

(22) Filed: Apr. 13, 2006

(65) Prior Publication Data

US 2006/0235327 A1    Oct. 19, 2006

(30) Foreign Application Priority Data

Apr. 13, 2005 (JP) ................... 2005-116059
Apr. 27, 2005 (JP) ................... 2005-130258
May 2, 2005 (JP) ................... 2005-134048
May 2, 2005 (JP) ................... 2005-134049

(51) Int. Cl.
*A61B 5/05* (2006.01)
*A61B 5/103* (2006.01)
*A61B 5/117* (2006.01)

(52) U.S. Cl. ................... 600/547; 600/587
(58) Field of Classification Search ............... 600/547
See application file for complete search history.

(56) References Cited

U.S. PATENT DOCUMENTS
3,994,284 A  11/1976  Voelker
(Continued)

FOREIGN PATENT DOCUMENTS
EP      1 203 562 A2    5/2002
(Continued)

OTHER PUBLICATIONS

Kanai et al., "Human Body Impedance for Electromagnetic Hazard Analysis in the VLF to MF Band", IEEE Transactions on Microwave Theory and Techniques, vol. MTT-32, No. 8, Aug. 1984, p. 763-772.*

(Continued)

*Primary Examiner* — Jeffrey G Hoekstra
*Assistant Examiner* — Devin Henson
(74) *Attorney, Agent, or Firm* — McDermott Will & Emery LLP

(57) ABSTRACT

A method and apparatus capable of measuring visceral fat tissues accumulated in the trunk with high accuracy apply a current to a body part where a subcutaneous fat tissue layer is thin or a body part where a skeletal muscle tissue layer has no or a thin muscle belly portion from a pair of current applying electrodes, measure a potential difference which has occurred in the tissue through which the current has passed by a pair of voltage measuring electrodes, and determine the visceral fat tissue volume of the trunk by use of the impedance of the trunk which has been obtained by use of the measured potential difference.

14 Claims, 35 Drawing Sheets

U.S. PATENT DOCUMENTS

| | | | |
|---|---|---|---|
| 5,052,405 A | 10/1991 | Batchelder | |
| 5,335,667 A | 8/1994 | Cha et al. | |
| 5,423,326 A | 6/1995 | Wang et al. | |
| 6,308,096 B1 | 10/2001 | Masuo | |
| 6,978,170 B1 | 12/2005 | Onda et al. | |
| 2002/0052697 A1 | 5/2002 | Serita | |
| 2004/0059242 A1* | 3/2004 | Masuo et al. | 600/547 |
| 2004/0077969 A1* | 4/2004 | Onda et al. | 600/547 |
| 2005/0101875 A1* | 5/2005 | Semler et al. | 600/509 |
| 2005/0107717 A1* | 5/2005 | Yamamoto et al. | 600/547 |
| 2006/0025701 A1 | 2/2006 | Kasahara | |
| 2006/0224080 A1* | 10/2006 | Oku et al. | 600/547 |
| 2009/0082679 A1* | 3/2009 | Chetham | 600/508 |

FOREIGN PATENT DOCUMENTS

| | | |
|---|---|---|
| EP | 1 621 131 A1 | 2/2006 |
| JP | 2002-238871 | 8/2002 |
| JP | 2002-369806 | 12/2002 |
| WO | WO 2006/027360 A1 | 3/2006 |

OTHER PUBLICATIONS

European Search Report issued in corresponding European Patent Application No. 06007739.3-2305, Dated Dec. 5, 2006.

European Search Report issued in corresponding European Patent Application No. EP 06 00 7739, dated Sep. 18, 2006.

* cited by examiner

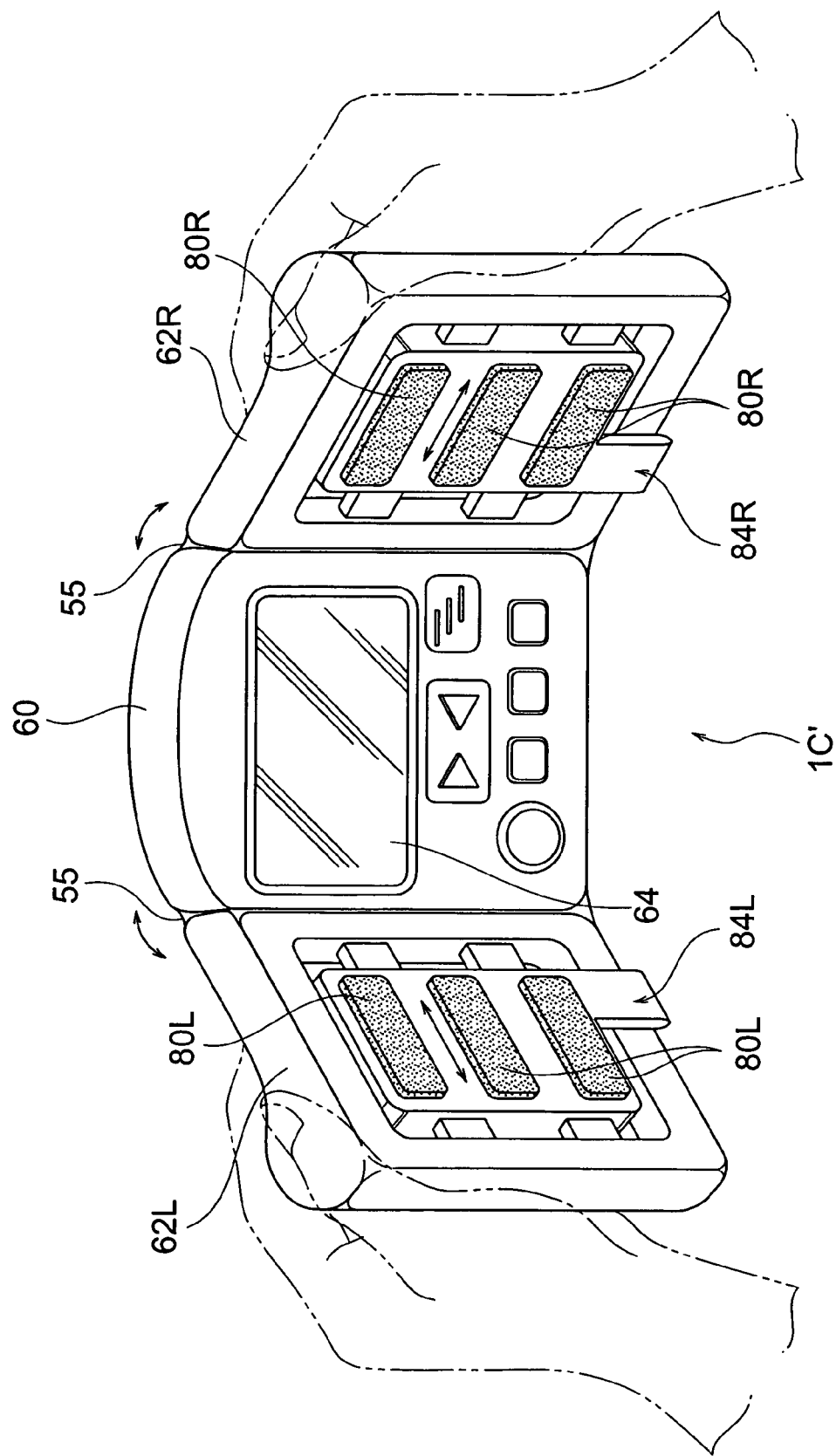

TRUNK VISCERAL FAT MEASURING METHOD AND APPARATUS, TRUNK SKELETAL MUSCLE AMOUNT MEASURING APPARATUS, TRUNK SUBCUTANEOUS FAT MEASURING METHOD AND APPARATUS, AND TRUNK VISCERAL AND SUBCUTANEOUS FAT MEASURING METHOD AND APPARATUS

BACKGROUND OF THE INVENTION (i) Field of the Invention

The present invention relates to a trunk visceral fat measuring method and apparatus, a trunk skeletal muscle amount measuring apparatus, a trunk subcutaneous fat measuring method and apparatus, and a trunk visceral and subcutaneous fat measuring method and apparatus.

(ii) Description of the Related Art

A technique for estimating body fat tissues by use of a bioelectrical impedance method has been spread as a technique for measuring body fat tissues and a body fat percentage. In reality, however, it does not measure fat tissues directly but electrically measures fat free tissues other than the fat tissues in which water is dominant. In particular, in whole body measurement, a conventional type (between-one-hand-and-one-foot lead system) models a body part between one hand and one foot in a supine position by one cylinder. As simple techniques, a between-palms lead system which makes a measurement in a standing position, a between-soles lead system integrated with a scale, and a technique for measuring an impedance by dividing a body into the upper limb and the lower limb, the upper limb, the lower limb and the trunk or five segments, e.g. the left and right upper extremities, the left and right lower extremities and the trunk, and applying a cylindrical model to each segment have been increasing popular. Further, a simplified impedance measurement technique comprising disposing current applying electrodes and voltage measuring electrodes around the navel of the trunk and measuring the impedance of the abdomen to estimate a visceral fat tissue amount has been applied for patent (refer to Patent Literatures 1 and 2).

Patent Literature 1

Japanese Patent Application No. 3,396,677

Patent Literature 2

Japanese Patent Application No. 3,396,674

However, the usefulness of information of body fat for screening lifestyle-related diseases such as diabetes, hypertension and hyperlipemia has been receiving particular attention, and the significance of measurement of visceral fat adhered or accumulated around the splanchnic organs has been increasing day by day.

Visceral fat tissues are fat tissues distributed around the abdomen of the trunk in a concentrated manner and have been determined by an image of a cross-sectional area of the fat tissues of the abdomen by X-ray CT or MRI. However, this requires a large-scale apparatus and has problems of X-ray exposure and high costs and is therefore not suited for measurement in the field and household. Consequently, the visceral fat tissues are generally estimated from correlation with the fat tissues of the whole body or correlation with the fat free tissues of the whole body and cannot secure adequate reliability for screening.

Recently, a method comprising disposing electrodes around the navel of the trunk and measuring the internal impedance of the trunk to estimate visceral fat tissue information has also been under development. However, this method is based on significant correlation existing among a skeletal muscle tissue layer, a subcutaneous fat tissue layer and visceral fat tissues and based on the premise that if information of any of these tissues can be acquired, the information can be roughly estimated. Therefore, while good results can be expected for highly independent, healthy subjects who can have highly significant correlation among the tissues, significant errors may be contained in measurement results for subjects having different correlations among the tissues, e.g. subjects having significantly enlarged visceral fat tissues and having significantly low correlation between the subcutaneous fat tissue layer or skeletal muscle tissue layer and the visceral fat tissues. That is, even this method under development has a significant problem in measurement on paralyzed patients and patients who need nursing care, particularly patients confined to bed, although the method can somehow make the measurement on healthy subjects capable of leading independent life regardless of where on the whole circumference of the navel the electrodes are disposed.

Further, this method under development is said to be a sophisticated technique in that it passes a current through a tissue part to be measured from the surface of the abdomen to acquire an impedance value associated with the internal tissue. However, it is an actual situation that measured impedance information itself has hardly useful sensitivity to visceral fat tissues due to the problem of the internal structure of the trunk which is a body part to be measured. That is, the trunk which is a body part to be measured is thick and short and has a multiple structure, i.e. a structure in which the visceral fat tissues to be measured together with splanchnic organ tissues and spinal tissues are covered with a skeletal muscle tissue layer showing very good electrical conductivity and the skeletal muscle tissue layer is covered with a subcutaneous fat tissue layer showing very poor electrical conductivity. In particular, around the visceral fat tissues to be measured, splanchnic organ tissues showing lower electrical conductivity than the skeletal muscle tissue layer and visceral fat tissues of poor electrical conductivity which are adhered and accumulated to the splanchnic organ tissues are dominant and constitute a complicated structure, resulting in very poor electrical conductivity of the tissues under the skeletal muscle tissue layer is very poor. For this reason, even if current applying electrodes are simply disposed around the abdomen, most of current passes through the skeletal muscle tissue layer, and current density distribution is observed from surface measuring electrodes as electrical potential distribution dominated by the skeletal muscle tissue layer. Further, applied current density distribution is determined from the surface area of the current applying electrode or the width of the electrode in the abdominal circumferential direction, and observation of information in a spreading resistance region showing high current density in the subcutaneous fat tissue layer right underneath the electrodes.

Further, since the trunk which is a body part to be measured is thick and short, sensitivity in the subcutaneous fat tissue layer in the current density concentrating (spreading resistance) region right underneath the current applying electrodes becomes high. Further, since the skeletal muscle tissues have very high electrical conductivity as compared with the fat tissues, most of current having passed through the subcutaneous fat tissue layer returns to the opposing current applying electrode via the skeletal muscle tissue layer and the subcutaneous fat tissue layer, and as a result, electrical potential distribution in the tissues under the skeletal muscle tissue layer is significantly distorted by the skeletal muscle tissue layer. Thus, in the conventional method, most of electrical potential measured is information of the subcutaneous fat tissue layer, energization of the visceral fat tissues to be measured, i.e. the splanchnic organ tissues and the visceral fat tissues adhered and accumulated therearound can be hardly expected, and only information with a very low measurement sensitivity of not higher than 10% of all impedance measurement section can be acquired.

To avoid these problems, a method comprising incorporating abdominal circumferential length having high correlation with a subcutaneous fat tissue layer area into an estimation expression to prevent an increase in estimation error is conceived. However, this method is merely indirect estimation by correlation between constituent tissues and is hardly called a measurement method having energization sensitivity required in the middle of the abdomen. That is, individual errors deviated from statistical correlation design cannot be assured, and particularly when the amount of the subcutaneous or visceral fat tissues is abnormally large or the intermediate skeletal muscle tissue layer is large or small, a significant error may occur. The subcutaneous fat tissue layer area has high correlation with the abdominal circumferential length, because the trunk of human being is concentric tissue arrangement design, the subcutaneous fat tissue layer is the outermost layer and its area is determined by outer circumferential length and subcutaneous fat tissue thickness.

To dispose electrodes on the trunk, a four-electrode technique is generally used. This method passes a current through the body of a subject and measures a potential difference which has occurred in a body part to be measured of the subject by the applied current so as to measure a bioelectrical impedance in the measured body part. When the four-electrode technique is applied to a thick and short body part to be measured such as the trunk, a current density concentrating region (or a spreading resistance region) when a current has just started to spread is, for example, right underneath current applying electrodes, so that a large potential difference occurs in the vicinity of the subcutaneous fat tissue layer and constitutes most of potential difference measured between voltage measuring electrodes. To reduce the influence by the spreading resistance, it is important to dispose the current applying electrodes and the voltage measuring electrodes with sufficient distance secured therebetween. Since general measurement is carried out under conditions which can secure a long measurement section and sufficient distance between the voltage measuring electrodes, so-called S/N sensitivity (N is the influence (noise) by the spreading resistance, and S is a signal measured between the voltage electrodes) should be secured sufficiently. However, in the case of a thick and short body part to be measured such as the trunk, when the voltage measuring electrodes are moved away to secure distance from the current applying electrodes so as to render N small, the distance between the voltage measuring electrodes becomes small. As a result, S becomes small, resulting in deterioration in S/N. Further, the spreading resistance portion showing high current density is a subcutaneous fat tissue layer portion and subjects liable to become obese with thick fat are common, so that N becomes quite large and S/N further deteriorates. Thus, when the four-electrode technique is applied to a thick and short body part to be measured such as the trunk, it is expected to be quite impossible to secure useful S/N sensitivity to visceral fat tissues merely by disposing the electrodes around the navel. S/N will be further described in detail in descriptions about Examples to be described later.

An object of the present invention is to solve the above problems of the prior art and provide a method and apparatus which can secure sensitivity required for measurement even in splanchnic organ tissue and visceral fat tissue regions having low electrical conductivity and measure information of fat tissues accumulated in the trunk, particularly, fat tissues adhered and accumulated around splanchnic organ tissues and fat tissues accumulated in the subcutaneous layer with high accuracy and with ease.

Another object of the present invention is to provide a method and apparatus which can secure sensitivity required for measurement even in splanchnic organ tissue and visceral fat tissue regions having low electrical conductivity and measure information of fat tissues accumulated in the trunk, particularly, fat tissues adhered and accumulated around splanchnic organ tissues with high accuracy and with ease and a health guideline advising apparatus.

Another object of the present invention is to provide a method and apparatus which can secure sensitivity required for measurement even in splanchnic organ tissue and visceral fat tissue regions having low electrical conductivity and measure information of fat tissues accumulated in the trunk, particularly, fat tissues adhered and accumulated around splanchnic organ tissues and fat tissues accumulated in the subcutaneous layer and subcutaneous fat tissue layer information simultaneously only by switching.

Another object of the present invention is to provide a trunk visceral fat measuring method and apparatus which can secure sensitivity required for measurement even in splanchnic organ tissue and visceral fat tissue regions having low electrical conductivity, measure information of fat tissues accumulated in the trunk, particularly, visceral fat tissues adhered and accumulated around splanchnic organ tissues and subcutaneous fat tissues accumulated in the subcutaneous layer with high accuracy and ease, and provide measurement result information having high measurement reproducibility and high reliability and excluding error factors ascribable to intricately mixed tissues.

SUMMARY OF THE INVENTION (1) According to one aspect of the present invention, there is provided a trunk visceral fat measuring method comprising the steps of:

applying a current from a pair of current applying electrodes to at least one of a body part where a subcutaneous fat tissue layer is thin and a body part where a skeletal muscle tissue layer has no or a thin muscle belly portion, measuring a potential difference which has occurred in the tissue through which the current has passed by a pair of voltage measuring electrodes, and determining the visceral fat tissue amount of the trunk by use of the impedance of the trunk which has been obtained by use of the potential difference.

According to one embodiment of the present invention, it is preferable that the current applying electrodes be disposed in the trunk circumferential direction and the voltage measuring electrodes be disposed at positions remote from the current applying electrodes in the trunk length direction to make the measurement.

According to another embodiment of the present invention, it is preferable that the voltage measuring electrodes measure the potential difference in a body part where the subcutaneous fat tissue layer is thin or a body part where the skeletal muscle tissue layer has no or a thin muscle belly portion.

According to still another embodiment of the present invention, it is preferable that the above trunk visceral fat measuring method determine a trunk skeletal muscle tissue volume based on body specifying information, determine the impedance of trunk skeletal muscle tissue layer based on the determined trunk skeletal muscle tissue volume and body specifying information, determine the splanchnic organ tissue volume of the trunk based on body specifying information, determine the impedance of the splanchnic organ tissue of the trunk based on the determined splanchnic organ tissue volume of the trunk and body specifying information, determine the impedance of the visceral fat tissue of the trunk based on the determined impedance of the trunk, the determined impedance of the trunk skeletal muscle tissue layer and the determined impedance of the splanchnic organ tissue of the trunk, and determine the visceral fat tissue amount of the trunk based on the determined impedance of the visceral fat tissue of the trunk and body specifying information.

According to still another embodiment of the present invention, the step of determining the impedance of the visceral fat tissue of the trunk based on the impedance of the trunk, the determined impedance of the trunk skeletal muscle tissue layer and the impedance of the splanchnic organ tissue of the trunk is characterized by an electrical equivalent circuit of the trunk in which the impedance of the trunk skeletal muscle tissue layer is connected in parallel to a series circuit of the impedance of the splanchnic organ tissue of the trunk and the impedance of the trunk visceral fat tissue.

According to still another embodiment of the present invention, the body part may be a section between the navel and the upper border of the iliac crest or aponeurosis between the rectus abdominis muscle and the external abdominal oblique muscle.

According to still another embodiment of the present invention, measurement of the impedance of the trunk may be carried out around the abdomen.

According to still another embodiment of the present invention, at least one electrode out of the current applying electrodes and the voltage measuring electrodes may be disposed off the abdominal circumference.

According to still another embodiment of the present invention, the current applying electrodes may be disposed on the abdominal circumference, and one or both of the voltage measuring electrodes may be disposed off the abdominal circumference.

According to still another embodiment of the present invention, the current applying electrodes may be disposed in the sections on the left and right sides when viewed with the navel as the center therebetween, while the voltage measuring electrodes may be disposed in the sections on the left and right sides when viewed with the navel as the center therebetween.

According to still another embodiment of the present invention, the voltage measuring electrodes may be disposed in the trunk longitudinal direction within an abdominal region off the abdominal circumference.

(2) According to another aspect of the present invention, a trunk visceral fat measuring apparatus is provided that comprises a pair of current applying electrodes which apply a current to at least one of a body part where a subcutaneous fat tissue layer is thin and a body part where a skeletal muscle tissue layer has no or a thin muscle belly portion and a pair of voltage measuring electrodes which measure a potential difference which has occurred in the tissue through which the current has passed and that determines the visceral fat tissue amount of the trunk by use of the impedance of the trunk which has been obtained by use of the potential difference.

According to one embodiment of the present invention, the current applying electrodes may be disposed in the trunk circumferential direction, and the voltage measuring electrodes may be disposed at positions remote from the current applying electrodes in the trunk length direction.

According to another embodiment of the present invention, it is preferable that the voltage measuring electrodes measure the potential difference in a body part where the subcutaneous fat tissue layer is thin or a body part where the skeletal muscle tissue layer has no or a thin muscle belly portion.

According to still another embodiment of the present invention, the above trunk visceral fat measuring apparatus may further comprise:
trunk skeletal muscle tissue volume estimating means,
trunk skeletal muscle tissue layer impedance estimating means,
trunk splanchnic organ tissue impedance estimating means,
trunk visceral fat tissue impedance estimating means, and
trunk visceral fat tissue amount estimating means,
wherein
the trunk skeletal muscle tissue volume estimating means estimates a trunk skeletal muscle tissue volume based on body specifying information,
the trunk skeletal muscle tissue layer impedance estimating means estimates the impedance of trunk skeletal muscle tissue layer based on the estimated trunk skeletal muscle tissue volume and body specifying information,
the trunk splanchnic organ tissue impedance estimating means estimates the splanchnic organ tissue volume of the trunk based on body specifying information and estimates the impedance of the splanchnic organ tissue of the trunk based on the estimated splanchnic organ tissue volume of the trunk and body specifying information,
the trunk visceral fat tissue impedance estimating means estimates the impedance of the visceral fat tissue of the trunk based on the estimated impedance of the trunk, the estimated impedance of the trunk skeletal muscle tissue layer and the estimated impedance of the splanchnic organ tissue of the trunk, and
the trunk visceral fat tissue amount estimating means estimates the visceral fat tissue amount of the trunk based on the estimated impedance of the visceral fat tissue of the trunk and body specifying information.

According to still another embodiment of the present invention, the trunk visceral fat tissue impedance estimating means may estimate the trunk visceral fat tissue impedance with an electrical equivalent circuit of the trunk in which the impedance of the trunk skeletal muscle tissue layer is connected in parallel to a series circuit of the impedance of the splanchnic organ tissue of the trunk and the impedance of the trunk visceral fat tissue.

According to still another embodiment of the present invention, the above trunk visceral fat measuring apparatus may further comprise breathing change influence removing means for removing the influence of change caused by breathing based on the impedance of the trunk which is measured in a sampling period shorter than breathing cycle time.

According to still another embodiment of the present invention, the above trunk visceral fat measuring apparatus may further comprise abnormal value determination process means for performing an abnormal value determination process by comparing the measured impedance of the trunk with a general value of a group.

According to still another embodiment of the present invention, the above trunk visceral fat measuring apparatus may further comprise display means for displaying advice information based on the result of determination made by the abnormal value determination process means.

According to still another embodiment of the present invention, the trunk visceral fat tissue amount may be represented by a trunk visceral fat percentage, a trunk visceral fat tissue cross-sectional area, a trunk visceral fat tissue volume or a trunk visceral fat tissue weight.

According to one embodiment of the present invention, in a trunk visceral fat measuring method that measures a trunk visceral fat tissue volume by use of the method described in (1), it is possible to:

apply a current from a pair of current applying electrodes to a body part where a subcutaneous fat tissue layer is thin or a body part where a skeletal muscle tissue layer has no or a thin muscle belly portion at first frequency and second frequency which is higher than the first frequency, measure a potential difference which has occurred by the current by a pair of voltage measuring electrodes, determine the impedance of the trunk, and determine the visceral fat tissue amount of the trunk by use of the determined impedance of the trunk.

According to another embodiment of the present invention, in a trunk visceral fat measuring method that measures a trunk visceral fat tissue volume by use of the method described in (1), it is possible to:

apply a current from a pair of current applying electrodes to a body part where a subcutaneous fat tissue layer is thin or a body part where a skeletal muscle tissue layer has no or a thin muscle belly portion at first frequency and second frequency which is higher than the first frequency, measure a potential difference which has occurred by the current by a pair of voltage measuring electrodes, measure the impedance of the trunk, determine the impedance of the skeletal muscle tissue layer of the trunk based on the measured impedance of the trunk, determine the splanchnic organ tissue volume of the trunk based on body specifying information, determine the impedance of the splanchnic organ tissues of the trunk based on the determined splanchnic organ tissue volume of the trunk and body specifying information, determine the impedance of the visceral fat tissues of the trunk based on the measured impedance of the trunk, the determined impedance of the skeletal muscle tissue layer of the trunk and the determined impedance of the splanchnic organ tissues of the trunk, and determine the visceral fat tissue amount of the trunk based on the determined impedance of the visceral fat tissues of the trunk and body specifying information.

According to still another embodiment of the present invention, in a trunk visceral fat measuring method that measures a trunk visceral fat tissue volume by use of the method described in (1), it is possible to:

apply a current from a pair of current applying electrodes to a body part where a subcutaneous fat tissue layer is thin or a body part where a skeletal muscle tissue layer has no or a thin muscle belly portion at first frequency and second frequency which is higher than the first frequency, measure a potential difference which has occurred by the current by a pair of voltage measuring electrodes, measure the impedance of the trunk, determine the impedance of the skeletal muscle tissue layer of the trunk based on the measured impedance of the trunk, determine the subcutaneous fat tissue volume of the trunk based on body specifying information, determine the impedance of the subcutaneous fat tissue layer of the trunk based on the determined subcutaneous fat tissue volume of the trunk and body specifying information, determine the splanchnic organ tissue volume of the trunk based on body specifying information, determine the impedance of the splanchnic organ tissues of the trunk based on the determined splanchnic organ tissue volume of the trunk and body specifying information, determine the impedance of the visceral fat tissues of the trunk based on the measured impedance of the trunk, the determined impedance of the skeletal muscle tissue layer of the trunk, the determined impedance of the subcutaneous fat tissue layer of the trunk and the determined impedance of the splanchnic organ tissues of the trunk, and determine the visceral fat tissue amount of the trunk based on the determined impedance of the visceral fat tissues of the trunk and body specifying information.

According to still another embodiment of the present invention, in a trunk visceral fat measuring method that measures a trunk visceral fat tissue volume by use of the method described in (1), it is possible to:

apply a current from a pair of current applying electrodes to a body part where a subcutaneous fat tissue layer is thin or a body part where a skeletal muscle tissue layer has no or a thin muscle belly portion at first frequency and second frequency which is higher than the first frequency, measure a potential difference which has occurred by the current by a pair of voltage measuring electrodes, measure the impedance of the trunk, determine the splanchnic organ tissue volume of the trunk based on body specifying information, determine the impedance of the splanchnic organ tissues of the trunk based on the determined splanchnic organ tissue volume of the trunk and body specifying information, determine the impedance of the visceral fat tissues of the trunk based on the measured impedance of the trunk and the determined impedance of the splanchnic organ tissues of the trunk, and determine the visceral fat tissue amount of the trunk based on the determined impedance of the visceral fat tissues of the trunk and body specifying information.

According to still another embodiment of the present invention, in a trunk visceral fat measuring method that measures a trunk visceral fat tissue volume by use of the method described in (1), it is possible to:

apply a current from a pair of current applying electrodes to a body part where a subcutaneous fat tissue layer is thin or a body part where a skeletal muscle tissue layer has no or a thin muscle belly portion at first frequency and second frequency which is higher than the first frequency, measure a potential difference which has occurred by the current by a pair of voltage measuring electrodes, measure the impedance of the trunk, determine the subcutaneous fat tissue volume of the trunk based on body specifying information, determine the impedance of the subcutaneous fat tissue layer of the trunk based on the determined subcutaneous fat tissue volume of the trunk and body specifying information, determine the splanchnic organ tissue volume of the trunk based on body specifying information, determine the impedance of the splanchnic organ tissues of the trunk based on the determined splanchnic organ tissue volume of the trunk and body specifying information, determine the impedance of the visceral fat tissues of the trunk based on the measured impedance of the trunk, the determined impedance of the subcutaneous fat tissue layer of the trunk and the determined impedance of the splanchnic organ tissues of the trunk, and determine the visceral fat tissue amount of the trunk based on the determined impedance of the visceral fat tissues of the trunk and body specifying information.

According to still another embodiment of the present invention, the step of determining the impedance of the visceral fat tissues of the trunk may be characterized by an electrical equivalent circuit of the trunk in which the impedance of the trunk skeletal muscle tissue layer is connected in parallel to a series circuit of the impedance of the splanchnic organ tissues of the trunk and the impedance of the trunk visceral fat tissues.

According to still another embodiment of the present invention, the step of determining the impedance of the visceral fat tissues of the trunk may be characterized by an electrical equivalent circuit of the trunk in which the impedance of the subcutaneous fat tissue layer of the trunk and the impedance of the trunk skeletal muscle tissue layer are connected in parallel to a series circuit of the impedance of the splanchnic organ tissues of the trunk and the impedance of the trunk visceral fat tissues.

According to still another embodiment of the present invention, a trunk visceral fat measuring apparatus that measures a trunk visceral fat tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency and a pair of voltage measuring electrodes which measure a voltage generated by the current, and the apparatus measures the impedance of the trunk at the first and second frequencies and determines the visceral fat tissue amount of the trunk by use of the measured impedances of the trunk.

According to still another embodiment of the present invention, a trunk visceral fat measuring apparatus that measures a trunk visceral fat tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency and a pair of voltage measuring electrodes which measure a potential difference which has occurred by the current, and the apparatus further comprises trunk bioelectrical impedance measuring means for measuring the impedance of the trunk at the first and second frequencies, trunk skeletal muscle tissue layer impedance estimating means for estimating the impedance of the skeletal muscle tissue layer of the trunk based on the measured impedances of the trunk, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the measured impedances of the trunk, the estimated impedance of the skeletal muscle tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

According to still another embodiment of the present invention, a trunk visceral fat measuring apparatus that measures a trunk visceral fat tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency and a pair of voltage measuring electrodes which measure a potential difference which has occurred by the current, and the apparatus further comprises trunk bioelectrical impedance measuring means for measuring the impedance of the trunk at the first and second frequencies, trunk skeletal muscle tissue layer impedance estimating means for estimating the impedance of the skeletal muscle tissue layer of the trunk based on the measured impedances of the trunk, trunk subcutaneous fat tissue layer impedance estimating means for estimating the subcutaneous fat tissue volume of the trunk based on body specifying information and estimating the impedance of the subcutaneous fat tissue layer of the trunk based on the estimated subcutaneous fat tissue volume of the trunk and body specifying information, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the measured impedances of the trunk, the estimated impedance of the skeletal muscle tissue layer of the trunk, the estimated impedance of the subcutaneous fat tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

According to still another embodiment of the present invention, a trunk visceral fat measuring apparatus that measures a trunk visceral fat tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly-portion at first frequency and second frequency which is higher than the first frequency and a pair of voltage measuring electrodes which measure a potential difference which has occurred by the current, and the apparatus further comprises trunk bioelectrical impedance measuring means for measuring the impedance of the trunk at the first and second frequencies, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the measured impedances of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

According to still another embodiment of the present invention, a trunk visceral fat measuring apparatus that measures a trunk visceral fat tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency and a pair of voltage measuring electrodes which measure a potential difference which has occurred by the current, and the apparatus further comprises trunk bioelectrical impedance measuring means for measuring the impedance of the trunk at the first and second frequencies, trunk subcutaneous fat tissue layer impedance estimating means for estimating the subcutaneous fat tissue volume of the trunk based on body specifying information and estimating the impedance of the subcutaneous fat tissue layer of the trunk based on the estimated subcutaneous fat tissue volume of the trunk and body specifying information, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the measured impedances of the trunk, the estimated impedance of the subcutaneous fat tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

According to still another embodiment of the present invention, the trunk visceral fat tissue impedance estimating means may make an estimation with an electrical equivalent circuit of the trunk in which the impedance of the trunk skeletal muscle tissue layer is connected in parallel to a series circuit of the impedance of the splanchnic organ tissues of the trunk and the impedance of the trunk visceral fat tissues.

According to still another embodiment of the present invention, the trunk visceral fat tissue impedance estimating means may make an estimation with an electrical equivalent circuit of the trunk in which the impedance of the subcutaneous fat tissue layer of the trunk and the impedance of the trunk skeletal muscle tissue layer are connected in parallel to a series circuit of the impedance of the splanchnic organ tissues of the trunk and the impedance of the trunk visceral fat tissues.

According to still another embodiment of the present invention, a trunk skeletal muscle volume measuring apparatus that measures a trunk skeletal muscle tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency and a pair of voltage measuring electrodes which measure a potential difference which has occurred by the current, and the apparatus measures the impedance of the trunk at the first and second frequencies and determines the skeletal muscle tissue volume of the trunk by use of the measured impedances of the trunk.

According to still another embodiment of the present invention, a trunk skeletal muscle volume measuring apparatus that measures a trunk skeletal muscle tissue volume by use of the apparatus described in (2) may be such that:

the apparatus comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency and a pair of voltage measuring electrodes which measure a potential difference which has occurred by the current, and the apparatus further comprises trunk bioelectrical impedance measuring means for measuring the impedance of the trunk at the first and second frequencies, trunk skeletal muscle tissue layer impedance estimating means for estimating the impedance of the skeletal muscle tissue layer of the trunk based on the impedances measured at the first and second frequencies, and trunk skeletal muscle tissue volume estimating means for estimating a trunk skeletal muscle tissue volume based on the estimated impedance of the skeletal muscle tissue layer of the trunk and body specifying information.

According to one embodiment of the present invention, the method described in (1) may be such that:

the current applying electrodes are disposed in the trunk circumferential direction, one of the voltage measuring electrodes is disposed in the vicinity of one of the current applying electrodes, and the other voltage measuring electrode is disposed at a position remote from the one of the current applying electrodes in the trunk length direction to measure the impedance of the trunk so as to determine trunk subcutaneous fat information.

According to another embodiment of the present invention, the method described in (1) may be such that:

a current is applied from one of the current applying electrodes to a body part where a subcutaneous fat tissue layer is thin or a body part where a skeletal muscle tissue layer has no or a thin muscle belly portion, one of the voltage measuring electrodes is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information.

According to still another embodiment of the present invention, the method described in (1) may be such that:

a current is applied from one current applying electrode included in at least one current applying electrode pair to a body part where a subcutaneous fat tissue layer is thin or a body part where a skeletal muscle tissue layer has no or a thin muscle belly portion;

one voltage measuring electrode included in one voltage measuring electrode pair out of at least two voltage measuring electrode pairs is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information;

the other voltage measuring electrode pair out of at least two voltage measuring electrode pairs are disposed at a remote position where the influence of the spreading resistance right underneath the current applying electrode is weak to measure a voltage so as to obtain visceral fat tissue information; and the one voltage measuring electrode pair and the other voltage measuring electrode pair are selected to obtain the subcutaneous fat tissue layer information and the visceral fat tissue information selectively.

According to still another embodiment of the present invention, the method described in (1) may:

determine the subcutaneous fat tissue volume of the trunk based on the impedance of the trunk which has been determined by use of the potential difference measured by the above one voltage measuring electrode pair and body specifying information, determine the impedance of trunk subcutaneous fat tissue layer based on the determined subcutaneous fat tissue volume of the trunk and body specifying information, determine the skeletal muscle tissue volume of the trunk based on body specifying information, determine the impedance of skeletal muscle tissue layer based on the determined skeletal muscle tissue volume of the trunk and body specifying information, determine the splanchnic organ tissue volume of the trunk based on body specifying information, determine the impedance of the splanchnic organ tissues of the trunk based on the determined splanchnic organ tissue volume of the trunk and body specifying information, determine the impedance of the visceral fat tissues of the trunk based on the impedance of the trunk which has been determined by use of the potential difference measured by the above other voltage measuring electrode pair, the determined impedance of the subcutaneous fat tissue layer of the trunk, the determined impedance of the skeletal muscle tissue layer of the trunk and the determined impedance of the splanchnic organ tissues of the trunk, and determine the visceral fat tissue amount of the trunk based on the determined impedance of the visceral fat tissues of the trunk and body specifying information.

According to still another embodiment of the present invention, the step of determining the impedance of the visceral fat tissues of the trunk based on the impedance of the trunk, the determined impedance of the skeletal muscle tissue layer of the trunk and the impedance of the splanchnic organ tissues of the trunk may be characterized by an electrical equivalent circuit of the trunk in which the impedance of the skeletal muscle tissue layer of the trunk is connected in parallel to a series circuit of the impedance of the splanchnic organ tissues of the trunk and the impedance of the visceral fat tissues of the trunk.

According to still another embodiment of the present invention, the step of determining the impedance of the visceral fat tissues of the trunk based on the impedance of the trunk, the determined impedance of the skeletal muscle tissue layer of the trunk and the impedance of the splanchnic organ tissues of the trunk may be characterized by an electrical equivalent circuit of the trunk in which the impedance of the skeletal muscle tissue layer of the trunk and the impedance of the subcutaneous fat tissue layer of the trunk are connected in parallel to a series circuit of the impedance of the splanchnic organ tissues of the trunk and the impedance of the visceral fat tissues of the trunk.

According to still another embodiment of the present invention, the apparatus described in (2) may:

comprise a pair of current applying electrodes disposed in the trunk circumferential direction, and voltage measuring electrodes one of which is disposed in the vicinity of one of the current applying electrodes and the other of which is disposed at a position remote from the one of the current applying electrodes in the trunk length direction, and determine trunk subcutaneous fat information by measuring the impedance of the trunk.

According to still another embodiment of the present invention, the apparatus described in (2) may be such that:

one of the current applying electrodes applies a current to a body part where subcutaneous fat is thin or a body part where a skeletal muscle tissue layer has no or a thin muscle belly portion, and the other current applying electrode applies a current to a body part where subcutaneous fat is thick;

one of the voltage measuring electrodes is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information.

According to still another embodiment of the present invention, the apparatus described in (2) may be such that:

one current applying electrode included in at least one current applying electrode pair applies a current to a body part where subcutaneous fat is thin or a body part where a skeletal muscle tissue layer has no or a thin muscle belly portion, and the other current applying electrode applies a current to a body part where subcutaneous fat is thick;

one voltage measuring electrode included in one voltage measuring electrode pair out of at least two voltage measuring electrode pairs is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information;

the other voltage measuring electrode pair out of at least two voltage measuring electrode pairs are disposed at a remote position where the influence of the spreading resistance right underneath the current applying electrode is weak to measure a potential difference so as to obtain visceral fat tissue information; and a switching device for selecting the one voltage measuring electrode pair and the other voltage measuring electrode pair to obtain the subcutaneous fat tissue information and the visceral fat tissue information selectively is further provided.

According to still another embodiment of the present invention, the apparatus described in (2) may further comprise:

trunk subcutaneous fat tissue volume estimating means for estimating the subcutaneous fat tissue volume of the trunk based on the impedance of the trunk which has been determined by use of the potential difference measured by the above one voltage measuring electrode pair and body specifying information, trunk subcutaneous fat tissue volume estimating means for estimating the subcutaneous fat tissue volume of the trunk based on the estimated subcutaneous fat tissue volume of the trunk and body specifying information, trunk subcutaneous fat tissue layer impedance estimating means for estimating the impedance of the subcutaneous fat tissue layer of the trunk based on the estimated subcutaneous fat tissue volume of the trunk and body specifying information, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the estimated impedance of the trunk, the estimated impedance of the skeletal muscle tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

According to one embodiment of the present invention, the method described in (1) may be such that:

a pair of current applying electrodes are disposed at a body part where a subcutaneous fat tissue layer is thin or a body part where a skeletal muscle tissue layer has no or a thin muscle belly portion, at least one pair of current applying electrodes or at least one pair of voltage measuring electrodes are further disposed on the navel circumferential surface or at a position distant from the navel circumferential surface in the trunk longitudinal direction by a certain distance, internal tissue information around the navel is measured in turn by a combination of the current applying electrode pair and the voltage measuring electrode pair, and the impedance of the trunk is measured by processing the measured informations.

According to another embodiment of the present invention, the method described in (1) may be such that:

the impedance of the trunk is measured, the impedance of the skeletal muscle tissue layer of the trunk is determined based on body specifying information, the impedance of the splanchnic organ tissues of the trunk is determined based on body specifying information, the impedance of the visceral fat tissues of the trunk is determined based on the measured impedance of the trunk, the determined impedance of the skeletal muscle tissue layer of the trunk and the determined impedance of the splanchnic organ tissues of the trunk, and the visceral fat tissue volume of the trunk is determined based on the determined impedance of the visceral fat tissues of the trunk and body specifying information.

According to still another embodiment of the present invention, the impedance of the skeletal muscle tissue layer of the trunk may be determined based on the skeletal muscle tissue volume of the trunk which has been determined based on body specifying information and body specifying information, and the impedance of the splanchnic organ tissues of the trunk may be determined based on the splanchnic organ tissue volume of the trunk which has been determined based on body specifying information and body specifying information.

According to still another embodiment of the present invention, the step of determining the impedance of the visceral fat tissues of the trunk based on the impedance of the trunk, the determined impedance of the skeletal muscle tissue layer of the trunk and the impedance of the splanchnic organ tissues of the trunk may be characterized by an electrical equivalent circuit of the trunk in which the impedance of the skeletal muscle tissue layer of the trunk is connected in parallel to a series circuit of the impedance of the splanchnic organ tissues of the trunk and the impedance of the visceral fat tissues of the trunk.

According to still another embodiment of the present invention, the apparatus described in (2) may comprise:

a pair of current applying electrodes disposed at a body part where a subcutaneous fat tissue layer is thin or a body part where a skeletal muscle tissue layer has no or a thin muscle belly portion, at least one pair of current applying electrodes or at least one pair of voltage measuring electrodes which are disposed on the navel circumferential surface or at a position distant from the navel circumferential surface in the trunk longitudinal direction by a certain distance, and means for measuring internal tissue information around the navel in turn by a combination of the current applying electrode pair and the voltage measuring electrode pair and measuring the impedance of the trunk by processing the measured informations.

According to still another embodiment of the present invention, the apparatus described in (2) may further comprise:

trunk bioelectrical impedance measuring means for measuring the impedance of the trunk, trunk skeletal muscle tissue layer impedance estimating means for estimating the impedance of the skeletal muscle tissue layer of the trunk based on body specifying information, trunk splanchnic organ tissue impedance estimating means for estimating the impedance of the splanchnic organ tissues of the trunk based on body specifying information, trunk visceral fat tissue impedance estimating means for estimating the impedance of the visceral fat tissues of the trunk based on the measured impedance of the trunk, the estimated impedance of the skeletal muscle tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

According to still another embodiment of the present invention, the trunk skeletal muscle tissue layer impedance estimating means may estimate the skeletal muscle tissue volume of the trunk based on body specifying information and estimate the impedance of the skeletal muscle tissue layer of the trunk based on the estimated skeletal muscle tissue volume of the trunk and body specifying information, and the trunk splanchnic organ tissue impedance estimating means may estimate the splanchnic organ tissue volume of the trunk based on body specifying information and estimating the impedance of the splanchnic organ tissues of the trunk based on the estimated splanchnic organ tissue volume of the trunk and body specifying information.

According to still another embodiment of the present invention, the trunk visceral fat tissue impedance estimating means may make an estimation with an electrical equivalent circuit of the trunk in which the impedance of the skeletal muscle tissue layer of the trunk is connected in parallel to a series circuit of the impedance of the splanchnic organ tissues of the trunk and the impedance of the visceral fat tissues of the trunk.

From another aspect, the present invention may be regarded as a trunk visceral fat measuring method for measuring the visceral fat tissues of the trunk that comprises the steps of:

applying a current from a pair of current applying electrodes to a body part where a subcutaneous fat tissue layer is thin or a body part where a skeletal muscle tissue layer has no or a thin muscle belly portion, at first frequency and second frequency which is higher than the first frequency, measuring a potential difference which has occurred by the current by a pair of voltage measuring electrodes, measuring the bioelectrical impedance of the trunk, and determining the visceral fat tissue volume of the trunk by use of the measured bioelectrical impedance.

Further, from another aspect, the present invention may be regarded as a trunk visceral fat measuring method for measuring the visceral fat tissues of the trunk that comprises the steps of:

applying a current from a pair of current applying electrodes to a body part where a subcutaneous fat tissue layer is thin or a body part where a skeletal muscle tissue layer has no or a thin muscle belly portion, at first frequency and second frequency which is higher than the first frequency, measuring a potential difference which has occurred by the current by a pair of voltage measuring electrodes, measuring the bioelectrical impedance of the trunk, determining the impedance of the skeletal muscle tissue layer of the trunk based on the bioelectrical impedances of the trunk measured at the first and second frequencies, determining the splanchnic organ tissue volume of the trunk based on body specifying information, determining the impedance of the splanchnic organ tissues of the trunk based on the determined splanchnic organ tissue volume of the trunk and body specifying information, determining the impedance of the visceral fat tissues of the trunk based on the determined bioelectrical impedance of the trunk, the determined impedance of the skeletal muscle tissue layer of the trunk and the determined impedance of the splanchnic organ tissues of the trunk, and determining the visceral fat tissue volume of the trunk based on the determined impedance of the visceral fat tissues of the trunk and body specifying information.

Further, from another aspect, the present invention may be regarded as a trunk visceral fat measuring method for measuring the visceral fat tissues of the trunk that comprises the steps of:

applying a current from a pair of current applying electrodes to a body part where a subcutaneous fat tissue layer is thin or a body part where a skeletal muscle tissue layer has no or a thin muscle belly portion, at first frequency and second frequency which is higher than the first frequency, measuring a potential difference which has occurred by the current by a pair of voltage measuring electrodes, measuring the bioelectrical impedance of the trunk, determining the impedance of the skeletal muscle tissue layer of the trunk based on the bioelectrical impedances of the trunk measured at the first and second frequencies, determining the subcutaneous fat tissue volume of the trunk based on body specifying information, determining the impedance of the subcutaneous fat tissue layer of the trunk based on the determined subcutaneous fat tissue volume of the trunk and body specifying information, determining the splanchnic organ tissue volume of the trunk based on body specifying information, determining the impedance of the splanchnic organ tissues of the trunk based on the determined splanchnic organ tissue volume of the trunk and body specifying information, determining the impedance of the visceral fat tissues of the trunk based on the determined bioelectrical impedance of the trunk, the determined impedance of the skeletal muscle tissue layer of the trunk, the determined impedance of the subcutaneous fat tissue layer of the trunk and the determined impedance of the splanchnic organ tissues of the trunk, and determining the visceral fat tissue volume of the trunk based on the determined impedance of the visceral fat tissues of the trunk and body specifying information.

Further, from another aspect, the present invention may be regarded as a trunk visceral fat measuring method for measuring the visceral fat tissues of the trunk that comprises the steps of:

applying a current from a pair of current applying electrodes to a body part where a subcutaneous fat tissue layer is thin or a body part where a skeletal muscle tissue layer has no or a thin muscle belly portion, at first frequency and second frequency which is higher than the first frequency, measuring a potential difference which has occurred by the current by a pair of voltage measuring electrodes, measuring the bioelectrical impedance of the trunk, determining the splanchnic organ tissue volume of the trunk based on body specifying information, determining the impedance of the splanchnic organ tissues of the trunk based on the determined splanchnic organ tissue volume of the trunk and body specifying information, determining the impedance of the visceral fat tissues of the trunk based on the bioelectrical impedances of the trunk measured at the first and second frequencies and the determined impedance of the splanchnic organ tissues of the trunk, and determining the visceral fat tissue volume of the trunk based on the determined impedance of the visceral fat tissues of the trunk and body specifying information.

Further, from another aspect, the present invention may be regarded as a trunk visceral fat measuring method for measuring the visceral fat tissues of the trunk that comprises the steps of:

applying a current from a pair of current applying electrodes to a body part where a subcutaneous fat tissue layer is thin or a body part where a skeletal muscle tissue layer has no or a thin muscle belly portion, at first frequency and second frequency which is higher than the first frequency, measuring a potential difference which has occurred by the current by a pair of voltage measuring electrodes, measuring the bioelectrical impedance of the trunk, determining the subcutaneous fat tissue volume of the trunk based on body specifying information, determining the impedance of the subcutaneous fat tissue layer of the trunk based on the determined subcutaneous fat tissue volume of the trunk and body specifying information, determining the splanchnic organ tissue volume of the trunk based on body specifying information, determining the impedance of the splanchnic organ tissues of the trunk based on the determined splanchnic organ tissue volume of the trunk and body specifying information, determining the impedance of the visceral fat tissues of the trunk based on the bioelectrical impedances of the trunk measured at the first and second frequencies, the determined impedance of the subcutaneous fat tissue layer of the trunk and the determined impedance of the splanchnic organ tissues of the trunk, and determining the visceral fat tissue volume of the trunk based on the determined impedance of the visceral fat tissues of the trunk and body specifying information.

Further, from another aspect, the present invention may be regarded as a trunk visceral fat measuring apparatus for measuring the visceral fat tissues of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a voltage generated by the current, and measures the bioelectrical impedance of the trunk at the first and second frequencies and determines the visceral fat tissue volume of the trunk by use of the measured bioelectrical impedances.

Further, from another aspect, the present invention may be regarded as a trunk visceral fat measuring apparatus for measuring the visceral fat tissues of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a potential difference which has occurred by the current, and further comprises trunk bioelectrical impedance measuring means for measuring the bioelectrical impedance of the trunk at the first and second frequencies, trunk skeletal muscle tissue layer impedance estimating means for estimating the impedance of the skeletal muscle tissue layer of the trunk based on the bioelectrical impedances of the trunk measured at the first and second frequencies, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the measured bioelectrical impedances of the trunk, the estimated impedance of the skeletal muscle tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

Further, from another aspect, the present invention may be regarded as a trunk visceral fat measuring apparatus for measuring the visceral fat tissues of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a potential difference which has occurred by the current, and further comprises trunk bioelectrical impedance measuring means for measuring the bioelectrical impedance of the trunk at the first and second frequencies, trunk skeletal muscle tissue layer impedance estimating means for estimating the impedance of the skeletal muscle tissue layer of the trunk based on the bioelectrical impedances of the trunk measured at the first and second frequencies, trunk subcutaneous fat tissue layer impedance estimating means for estimating the subcutaneous fat tissue volume of the trunk based on body specifying information and estimating the impedance of the subcutaneous fat tissue layer of the trunk based on the estimated subcutaneous fat tissue volume of the trunk and body specifying information, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the measured bioelectrical impedances of the trunk, the estimated impedance of the skeletal muscle tissue layer of the trunk, the estimated impedance of the subcutaneous fat tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

Further, from another aspect, the present invention may be regarded as a trunk visceral fat measuring apparatus for measuring the visceral fat tissues of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a potential difference which has occurred by the current, and further comprises trunk bioelectrical impedance measuring means for measuring the bioelectrical impedance of the trunk at the first and second frequencies, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the bioelectrical impedances of the trunk measured at the first and second frequencies and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

Further, from another aspect, the present invention may be regarded as a trunk visceral fat measuring apparatus for measuring the visceral fat tissues of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a potential difference which has occurred by the current, and further comprises trunk bioelectrical impedance measuring means for measuring the bioelectrical impedance of the trunk at the first and second frequencies, trunk subcutaneous fat tissue layer impedance estimating means for estimating the subcutaneous fat tissue volume of the trunk based on body specifying information and estimating the impedance of the subcutaneous fat tissue layer of the trunk based on the estimated subcutaneous fat tissue volume of the trunk and body specifying information, trunk splanchnic organ tissue impedance estimating means for estimating the splanchnic organ tissue volume of the trunk based on body specifying information and estimating the impedance of the splanchnic organ tissues of the trunk based on the estimated splanchnic organ tissue volume of the trunk and body specifying information, trunk visceral fat tissue impedance estimating means for estimating the impedance of the visceral fat tissues of the trunk based on the bioelectrical impedances of the trunk measured at the first and second frequencies, the estimated impedance of the subcutaneous fat tissue layer of the trunk and the estimated impedance of the splanchnic organ tissues of the trunk, and trunk visceral fat tissue volume estimating means for estimating the visceral fat tissue volume of the trunk based on the estimated impedance of the visceral fat tissues of the trunk and body specifying information.

Further, from another aspect, the present invention may be regarded as a trunk skeletal muscle volume measuring apparatus for measuring the skeletal muscle tissue volume of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a potential difference that has occurred by the current, and measures the bioelectrical impedance of the trunk at the first and second frequencies and determines the skeletal muscle tissue volume of the trunk by use of the measured bioelectrical impedances.

Further, from another aspect, the present invention may be regarded as a trunk skeletal muscle volume measuring apparatus for measuring the skeletal muscle tissue volume of the trunk which:

comprises a pair of current applying electrodes which apply a current to a body part where a subcutaneous fat tissue layer is thin or a body part where a skeletal muscle tissue layer has no or a thin muscle belly portion at first frequency and second frequency which is higher than the first frequency, and a pair of voltage measuring electrodes which measure a potential difference which has occurred by the current, and further comprises trunk bioelectrical impedance measuring means for measuring the bioelectrical impedance of the trunk at the first and second frequencies, trunk skeletal muscle tissue layer impedance estimating means for estimating the impedance of the skeletal muscle tissue layer of the trunk based on the bioelectrical impedances of the trunk measured at the first and second frequencies, and trunk skeletal muscle tissue volume estimating means for estimating the skeletal muscle tissue volume of the trunk based on the estimated impedance of the skeletal muscle tissue layer of the trunk and body specifying information.

Further, from another aspect, the present invention may be regarded as a trunk subcutaneous fat measuring method, wherein a pair of current applying electrodes are disposed in the trunk circumferential direction, one of voltage measuring electrodes is disposed in the vicinity of one of the current applying electrodes, and the other voltage measuring electrode is disposed at a position remote from the one of the current applying electrodes in the trunk length direction to measure the impedance of the trunk so as to determine trunk subcutaneous fat information.

Further, from another aspect, the present invention may be regarded as a trunk subcutaneous fat measuring method, wherein a current is applied from one current applying electrode included in a current applying electrode pair to a body part where a subcutaneous fat tissue layer is thin or a body part where a skeletal muscle tissue layer has no or a thin muscle belly portion;

one voltage measuring electrode included in a voltage measuring electrode pair is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information.

Further, from another aspect, the present invention may be regarded as a trunk visceral/subcutaneous fat measuring method, wherein a current is applied from one current applying electrode included in at least one current applying electrode pair to a body part where a subcutaneous fat tissue layer is thin or a body part where a skeletal muscle tissue layer has no or a thin muscle belly portion;

one voltage measuring electrode included in a voltage measuring electrode pair out of at least two voltage measuring electrode pairs is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information;

the other voltage measuring electrode pair out of at least two voltage measuring electrode pairs are disposed at a remote position where the influence of the spreading resistance right underneath the current applying electrode is weak to measure a voltage so as to obtain visceral fat tissue information; and the one voltage measuring electrode pair and the other voltage measuring electrode pair are selected to obtain the subcutaneous fat tissue layer information and the visceral fat tissue information selectively.

Further, from another aspect, the present invention may be regarded as a trunk subcutaneous fat measuring apparatus which:

comprises a pair of current applying electrodes disposed in the trunk circumferential direction and voltage measuring electrodes one of which is disposed in the vicinity of one of the current applying electrodes and the other of which is disposed at a position remote from the one of the current applying electrodes in the trunk length direction, and determines trunk subcutaneous fat information by measuring the impedance of the trunk.

Further, from another aspect, the present invention may be regarded as a trunk subcutaneous fat measuring apparatus, wherein the apparatus comprises a pair of current applying electrodes and a pair of voltage measuring electrodes;

one of the current applying electrodes applies a current to a body part where subcutaneous fat is thin or a body part where a skeletal muscle tissue layer has no or a thin muscle belly portion, and the other current applying electrode applies a current to a body part where subcutaneous fat is thick; and one of the voltage measuring electrodes is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information.

Further, from another aspect, the present invention may be regarded as a trunk visceral/subcutaneous fat measuring apparatus, wherein the apparatus comprises at least one current applying electrode pair and at least two voltage measuring electrode pairs, one current applying electrode included in at least one current applying electrode pair applies a current to a body part where subcutaneous fat is thin or a body part where a skeletal muscle tissue layer has no or a thin muscle belly portion, and the other current applying electrode applies a current to a body part where subcutaneous fat is thick;

one voltage measuring electrode included in one voltage measuring electrode pair out of at least two voltage measuring electrode pairs is disposed at a position where the influence of spreading resistance right underneath the current applying electrode is predominant, and the other voltage measuring electrode is disposed at a remote position where the influence of the spreading resistance right underneath the current applying electrode is weak to measure a potential difference between the voltage measuring electrodes so as to obtain subcutaneous fat tissue information;

the other voltage measuring electrode pair out of at least two voltage measuring electrode pairs are disposed at a remote position where the influence of the spreading resistance right underneath the current applying electrode is weak to measure a potential difference so as to obtain visceral fat tissue information; and the apparatus further comprises a switching device which can select the one voltage measuring electrode pair and the other voltage measuring electrode pair to obtain the subcutaneous fat tissue information and the visceral fat tissue information selectively.

Further, from another aspect, the present invention may be regarded as a trunk visceral fat measuring method for determining the visceral fat tissue volume of the trunk by use of the bioelectrical impedance of the trunk which has been measured by use of a pair of current applying electrodes and a pair of voltage measuring electrodes, wherein a pair of current applying electrodes are disposed at a body part where a subcutaneous fat tissue layer is thin or a body part where a skeletal muscle tissue layer has no or a thin muscle belly portion, at least one pair of current applying electrodes or at least one pair of voltage measuring electrodes are further disposed on the navel circumferential surface or at a position distant from the navel circumferential surface in the trunk longitudinal direction by a certain distance, internal tissue information around the navel is measured in turn by a combination of the current applying electrode pair and the voltage measuring electrode pair, and the bioelectrical impedance of the trunk is measured by processing the measured informations.

Further, from another aspect, the present invention may be regarded as a trunk visceral fat measuring apparatus which determines the visceral fat tissue volume of the trunk by use of the bioelectrical impedance of the trunk which has been measured by use of a pair of current applying electrodes and a pair of voltage measuring electrodes, the apparatus comprising:

a pair of current applying electrodes disposed at a body part where a subcutaneous fat tissue layer is thin or a body part where a skeletal muscle tissue layer has no or a thin muscle belly portion, at least one pair of current applying electrodes or at least one pair of voltage measuring electrodes which are disposed on the navel circumferential surface or at a position distant from the navel circumferential surface in the trunk longitudinal direction by a certain distance, and means for measuring internal tissue information around the navel in turn by a combination of the current applying electrode pair and the voltage measuring electrode pair and measuring the bioelectrical impedance of the trunk by processing the measured informations.

According to the present invention, the visceral fat tissues of the trunk can be measured with high accuracy by increasing the amount of a current applied to splanchnic organ tissues and visceral fat tissues and the sensitivity thereof. As for the N component which is noise caused by disturbance of potential caused by the skeletal muscle tissue layer, the S/N property can be improved by disposing voltage measuring electrodes off the abdominal tissues.

Further, even paralyzed patients and subjects confined to bed such as those who need nursing care can perform a measurement easily by using the front side of the abdomen as a measurement section. Further, since attachment of electrodes to the abdomen can help subjects be aware of a body part to be measured, it is advantageous to an improvement in measurement accuracy and securing of motivation by conscious constraint.

Further, while adhering to a combination with a conventional measurement method and ease of use, highly accurate screening information according to a required level can be exposed for the degree of accumulation of fat tissues adhering around splanchnic organ tissues.

Further, according to the present invention, since the visceral fat tissues of the trunk can be measured with high accuracy by a small and simple apparatus, it can be used as an optimum apparatus for domestic use. Further, the present invention can also perform checking of the condition of the abdomen prior to measurement, i.e. early checking of inflammation and abnormality in body fluid distribution in splanchnic organ tissues and the like and give appropriate health guideline advice according to the checking result. Therefore, users can acquire a variety of information useful for proper exercise of daily diet by food and exercise, maintenance of motivation therefor and sustainable self-management for maintenance and improvement of health in a simple manner, and the information is very useful.

Further, according to the present invention, it is possible to measure a tissue impedance in at least two frequency bands, i.e. a frequency band f1 with high dependency of around 50 kHz and lower and a frequency band f2 with nearly negligible influence of dependency of higher than f1 and 150 kHz and higher (S/N can be barely secured at 100 kHz) by use of the frequency dependency of the skeletal muscle tissue layer and separate internal tissues.

Further, in the trunk section, visceral fat tissue volumes can be separated and measured by use of impedance measured values at the two frequencies and body specifying information.

Further, according to the present invention, measurement result information with high measurement reproducibility and high reliability can be provided, and the influence of error when the positions of measuring electrodes are slightly off the navel circumference can be reduced. In addition, averaged electrical information with high reproducibility can be provided for complicated complex tissues between splanchnic organ tissues and visceral fat tissues, the influence of small changes in position between internal tissues by breathing and posture on measurements can be reduced, and the influence of retention of urine and stool in splanchnic organ tissues can be reduced.

BRIEF DESCRIPTION OF THE DRAWINGS

FIG. 47 is a schematic diagram illustrating a variation of the trunk visceral fat measuring apparatus according to the fourth embodiment of the present invention.

DETAILED DESCRIPTION OF THE PREFERRED EMBODIMENTS

Figure 1:
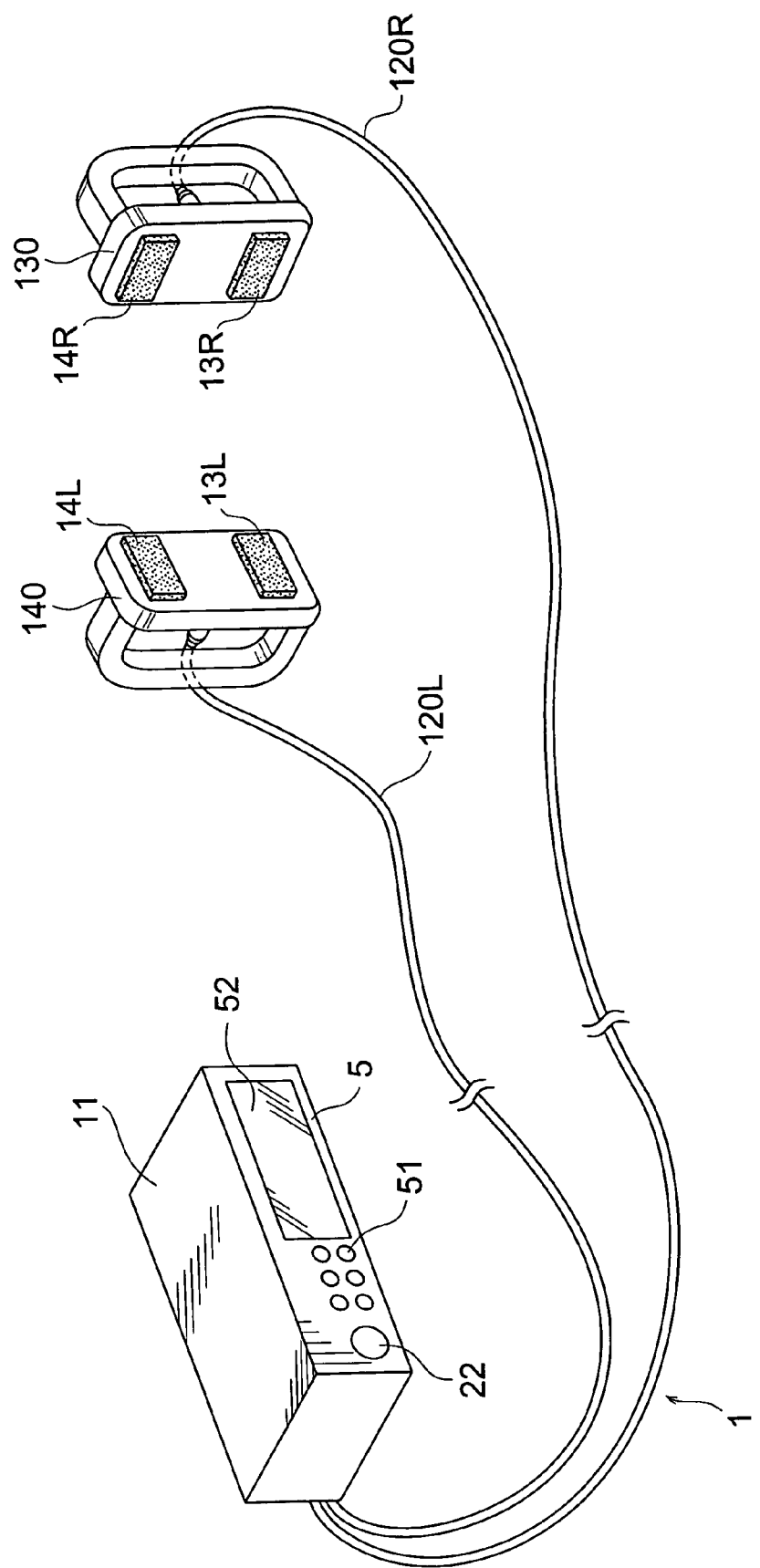
FIG. 1 is a schematic perspective view of the appearance of an example of a trunk visceral fat measuring apparatus according to a first embodiment of the present invention.

The principle of measurement of the visceral fat of the trunk according to the present invention will be described before the embodiments and examples of the present invention are described in detail. The present invention basically relates to a method capable of measuring visceral fat tissue information (cross-sectional area, volume or weight) of the trunk (abdomen), more specifically, information about fat tissues accumulated in the trunk, particularly, information about fat tissues adhered and accumulated around splanchnic organ tissues and fat tissues accumulated in the subcutaneous layer, with ease and high accuracy, by use of bioelectrical impedance information and body specifying information.

The present invention uses the following techniques accordingly.

(1) Tissue information included in the bioelectrical impedance information of the trunk is assumed by a series-parallel equivalent circuit model based on the skeletal muscle tissue layer, splanchnic organ tissues and visceral fat tissues. In this case, the splanchnic organ tissues and the visceral fat tissues are considered to be in series (hence, a change in the amount of applied current can be expected according to the size of the visceral fat tissues.)

(2) When abdominal circumferential length can be secured as body specifying information, a subcutaneous fat tissue volume is also included, and the tissue information is assumed by a high-accuracy series-parallel equivalent circuit model based on the subcutaneous fat tissue layer, skeletal muscle tissue layer, splanchnic organ tissues and visceral fat tissues.

(3) Estimation of the subcutaneous fat tissue volume is constituted by a multiple regression formula using abdominal circumferential length out of body specifying information as a main explanatory variable. Further, square of the abdominal circumferential length is set as a main explanatory variable.

(4) Confirmation of splanchnic organ tissue information is constituted by a multiple regression formula using body height information out of body specifying information as a main explanatory variable. It is used for confirmation of unconfirmed information for estimation of visceral fat tissue information.

(5) Reference measurements of tissues used for multiple regression analysis (calibration curve preparation technique) for quantifying tissues can be achieved by a tissue cross-sectional area (CSA) from an X-ray CT tomographic image of navel area, CSA by MRI, and the tissue volume and weight (conversion of the volume to the weight can be calculated from tissue density information by previous research) using DEXA or MRI (integration processing in the longitudinal direction for each slice) in the whole trunk. DEXA can achieve reference measurement of the total fat tissue information of abdominal visceral fat tissues and subcutaneous fat tissues.

(6) To acquire visceral fat tissue information with high accuracy by use of the above techniques, a measure to replace a change in measured impedance information of the trunk by breathing with a given condition value is required. An impedance measurement sampling period is set within a half of a general breathing cycle, a change in breathing is monitored with time, and a breathing cycle and the maximum and minimum values in the breathing cycle are determined in each breathing cycle, thereby making possible acquisition of the median in quiet breathing.

(7) Further, advance checking of the adverse effects by drinking and eating before measurement and retention of urine in the bladder is enabled by measured impedance information. In general, information about the skeletal muscle tissue layer is predominantly reflected in the impedance value of the trunk, in a group of ordinary healthy subjects. Further, the information about the skeletal muscle tissue layer of the trunk is very small as a measurement value and is not significantly different among individuals. The reason is that since it has design having a high correlation with antigravity muscles that develop by supporting the weights thereof under the gravity of the earth, it is determined mostly by a body size except for groups of special subjects such as subjects who are confined to bed and free from the influence of gravity and athletes of sports which impose stress whish is several times larger than the weights of the athletes on the athletes. In addition to the skeletal muscle tissue layer and the change in breathing, the adverse effects by drinking and eating and retention of urine in the bladder significantly influence the impedance of the trunk. Therefore, when the impedance values of the trunks are collected as group data and the mean value [mean] and deviation [SD] are checked, it is understood that the effects by drinking and eating and retention of urine in the bladder exceed 2 SD. However, when quasi-general groups such as athletes of certain level are taken into account, the effects can be screened by setting 3 SD as a criterion.

(8) Impedance information of the trunk (middle) portion and impedance measuring frequency for measuring the impedance information are implemented by two frequencies. By use of body specifying information, skeletal muscle tissue layer information of the abdomen (middle portion) is exposed. It is used for confirmation of unconfirmed information for estimation of visceral fat tissue information.

(9) A serial tissue structure of splanchnic organ tissues and visceral fat tissues can be specified by measuring the trunk by two frequencies on a parallel configuration of the serial tissue structure of splanchnic organ tissues and visceral fat tissues and the skeletal muscle tissue layer.

Hereinafter, the measurement principle of the present invention based on the above techniques will be further described.

1. Formation of Electrical Equivalent Circuit Model of Trunk Constituting Tissues (1) It can be considered that the trunk is primarily constituted by a subcutaneous fat tissue layer, a skeletal muscle tissue layer (abdominal muscles, back muscles), splanchnic organ tissues and visceral fat tissues adhered therebetween. Bone tissues are not named as constituting tissues because the bone tissues have a very high quantitative correlation with the skeletal muscle tissue layer and can be considered as an integrated tissue structure with the skeletal muscle tissue layer. It is assumed that as to volume-resistivity, conductivity becomes very high by including myeloid tissues in a living body and it has properties close to those of the skeletal muscle tissue layer and the splanchnic organ tissues. Therefore, when these four tissues are represented by an electrical equivalent circuit model, the splanchnic organ tissues and the visceral fat tissues are constituted in series, and the subcutaneous fat tissue layer and the skeletal muscle tissue layer are constituted in parallel with the serially combined tissues. This equivalent circuit model will be described in detail in descriptions of Examples to be described later. According to this model, a current passes predominantly through the skeletal muscle tissue layer when the current is passed in the longitudinal direction of the trunk. Because the visceral fat tissues adhere to gaps around the splanchnic organ tissues and because the splanchnic organ tissues shows electrical conductivity close to that of the skeletal muscle tissue layer when the visceral fat tissues do not exist or exist in small quantity, a current also passes through the splanchnic organ tissue side. Further, the larger the quantity of the visceral fat tissues becomes, the smaller the amount of a current passing through a combined tissue layer as a complex of the splanchnic organ tissues and the visceral fat tissues becomes. A model expression when the measured impedance of the trunk and the four tissues constituting the trunk are represented by an equivalent circuit model can be expressed as follows.

$$Z_{tm} = ZFS//ZMM//(ZVM+ZFV) \quad \text{expression 1}$$

impedance of entire trunk: $Z_{tm}$ impedance of subcutaneous fat tissue layer: ZFS . . . volume-resistivity is high.

impedance of skeletal muscle tissue layer: ZMM . . . volume-resistivity is low.

impedance of splanchnic organ tissues: ZVM . . . volume-resistivity is considered to be close to that of skeletal muscle tissue layer.

impedance of visceral fat tissues: ZFV . . . volume-resistivity is considered to be equal to or slightly lower than that of subcutaneous fat tissue layer. It is conceived that the quantity of blood vessels in the tissues and the amount of blood are large due to faster synthesis and decomposition of fat than subcutaneous fat.

The electrical characteristics between tissues are determined by volume-resistivity $\rho[\Omega m]$ rather than impedance. According to the above relationships, the electrical characteristic values of the tissues are generally described by the following relationships.

$\rho MM << \rho(VM+FV) < \rho FS$ $\rho VM << \rho FV$ $\rho MM = \rho VM$, or, $\rho MM < \rho VM$ $\rho FV = \rho FS$, or, $\rho FV < FS$ volume-resistivity of subcutaneous fat tissue layer: $\rho FS$ volume-resistivity of combined tissue layer of splanchnic organ tissues and visceral fat tissues inside skeletal muscle tissue layer: $\rho(VM+FV)$ volume-resistivity of skeletal muscle tissue layer: $\rho MM$ Therefore, in relation to the expression 1, the comparative relationship of the electrical characteristics between the tissues can be expressed as follows.

$$ZFS >> (ZVM+ZFV) >> ZMM \quad \text{expression 2}$$

2. Estimations of Trunk Skeletal Muscle Tissue Cross-Sectional Area (AMM) and Trunk Skeletal Muscle Tissue Layer Impedance (ZMM)

(2) A visceral fat tissue volume can be expressed by a cross-sectional area or a volume. In the case of the cross-sectional area, in measurement around the navel, a cross-sectional area by CT (X ray-CT, MRI) is considered to be a general measurement standard. Meanwhile, in the case of the volume, it can be determined by integrating a cross-sectional area by slicing by CT with a plurality of slice information in the longitudinal direction. A skeletal muscle tissue volume (skeletal muscle volume) is considered to have a high correlation with both of the cross-sectional area and the volume. In this case, the cross-sectional area is considered. The cross-sectional area (AMM) of the skeletal muscle tissue layer can be roughly estimated by body specifying information, because the development design of the skeletal muscle tissue layer of a body is mostly determined by development and adaptation for supporting its own weight under the gravity of the earth. Therefore, the cross-sectional area (AMM) can be estimated by body specifying information, except for those unadapted to gravity such as athletes, paralyzed patients and those who need nursing care. This estimation is made by substituting a body height H, a body weight W and age AGE into the following expression:

$$AMM = a \times H + b \times W + c \times AGE + d \quad \text{expression 3}$$

wherein a, b, c and d are constants.

(3) A trunk skeletal muscle tissue layer impedance (ZMM) can also be estimated by body specifying information. For the sake of convenience, the above estimated cross-sectional-area (AMM) is used in this case. This estimation can be made by use of the following expression:

$$ZMM = a0 \times H/AMM + b3 \quad \text{expression 4}$$

wherein a0 and b0 are constants.

3. Estimations of Visceral Fat Tissue Impedance (ZFV) and Visceral Fat Tissue Volume (AFV)

The following two approaches are conceivable from the relational expressions 1 and 2 as techniques capable of estimating visceral fat tissue information.

(4) Approach 1

The subcutaneous fat tissue layer is omitted from the viewpoint of the equivalent circuit of the trunk since it has high volume-resistivity as compared with other constituting tissues. That is, it can be considered that an impedance value measured in the trunk includes measured information about fat free tissues including visceral fat tissues excluding the subcutaneous fat tissue layer of the trunk. Therefore, this relational expression can be expressed as follows.

$$Z_{tm} \approx ZMM//(ZVM+ZFV) \quad \text{expression 5}$$

The expression can be converted into the following expression.

$$1/Z_{tm} \approx 1/ZMM + 1/(ZVM+ZFV) \quad \text{expression 6}$$

The impedance ZFV of the visceral fat tissues can be calculated by exposing the impedance ZMM of the skeletal muscle tissue layer and the impedance ZVM of the splanchnic organ tissues by the following means. Then, a visceral fat tissue volume can be estimated from the impedance information of the visceral fat tissues. The expression 6 is turned into the following expression 7 by deriving ZFV from the expression 6, and impedance information having visceral fat tissue information can be determined.

$$ZFV=1/[1/Z_{tm}-1/ZMM]-ZVM \quad \text{expression 7}$$

(5) Approach 2

Although the subcutaneous fat tissue layer is not taken into consideration in the above approach 1, this can cause an error for subjects having a large quantity of subcutaneous fat tissues. Hence, the approach 2 is a method following the expression 1 as it is.

The impedance ZMM of the skeletal muscle tissue layer and the impedance ZVM of the splanchnic organ tissues are the same as those in the above technique, and the impedance ZFS of the subcutaneous fat tissue layer has an useful relationship with a subcutaneous fat tissue volume as in the case of the other tissues. It is generally reported that the subcutaneous fat tissue volume has a very high correlation with circumferential length on the tissue surface, i.e. abdominal circumferential length (particularly for subjects having a large quantity of subcutaneous fat tissues or when the subcutaneous fat tissues are large as compared with fat free tissues excluding the subcutaneous fat tissues). Therefore, the subcutaneous fat tissue layer can be estimated from abdominal circumferential length information. Consequently, the impedance of the subcutaneous fat tissue layer can be estimated from the abdominal circumferential length information. Then, the impedance ZFV of the visceral fat tissues can be calculated in the same manner as in the above approach. Then, a visceral fat tissue volume can be estimated from the impedance information of the visceral fat tissues.

The expression 1 can be converted into the following expressions.

$$1/Z_{tm}=1/ZFS+1/ZMM+1/(ZVM+ZFV) \quad \text{expression 8}$$

$$ZFV=1/[1/Z_{tm}-1/ZMM-1/ZFS]-ZVM \quad \text{expression 9}$$

(6) The visceral fat tissue volume (AFV) is treated as a visceral fat tissue cross-sectional area in this case. The visceral fat tissue volume (AFV) can be calculated from the above impedance information and body height information in the following expression 10.

$$AFV=aa \times H/ZFV+bb \quad \text{expression 10}$$

wherein aa and bb are constants.

4. Estimations of Splanchnic Organ Tissue Volume [AVM] and Splanchnic Organ Tissue Impedance [ZVM]

(7) The splanchnic organ tissue volume [VM] of the trunk can be estimated from body (individual) specifying information including a body height, a body weight, gender and age. Of explanatory variables, the influence of body height term is significant.

$$\text{Splanchnic Organ Tissue Volume}[AVM]=a1 \times \text{Body Height}[H]+b1 \times \text{Body Weight}[W]+c1 \times \text{Age}[age]+d1 \quad \text{expression 11}$$

wherein a1, b1, c1 and d1 are constants showing different values for a male and a female.

Measurement of the reference volume for the visceral fat tissue volume VM used in the calibration curve (regression formula) is a tissue volume obtained by integrating CSA (tissue cross-sectional area) for each slice obtained by MRI or X-ray CT in the longitudinal direction or CSA from one slice of the navel site or the like. The tissue volume can be converted into a tissue amount by converting tissue density information known by previous research papers and the like into weight.

(8) Next, the impedance ZVM of the splanchnic organ tissues is estimated.

The impedance [ZVM] of the splanchnic organ tissues can be estimated from body (individual) specifying information including a body height, a body weight, gender and age. Of explanatory variables, the influence of body height term is significant. For the sake of convenience, the above estimated splanchnic organ tissue volume [AVM] is used in this case. This estimation can be made by use of the following expression.

$$ZVM=a2 \times H/AVM+b2 \quad \text{expression 12}$$

wherein a2 and b2 are constants.

5. Estimation of Subcutaneous Fat Tissue Volume [AFS] (Part 1)

(9) The subcutaneous fat tissue volume [AFS] of the trunk can be estimated from abdominal circumferential length [Lw]$^2$. Further, an improvement in accuracy can be expected by adding other body specifying information as explanatory variables to form multiple regression formulae.

For Male: Subcutaneous Fat Tissue Volume$[AFS]=$
$a10 \times$Abdominal Circumferential Length$[Lw]^2+$
$b10 \times$Body Height$[H]+c10 \times$Body Weight$[W]+$
$d10 \times$age$[Age]+e10$ \quad expression 13

For Female: Subcutaneous Fat Tissue Volume$[AFS]=$
$a11 \times$Abdominal Circumferential Length$[Lw]^2+$
$b11 \leq$Body Height$[H]+c11 \times$BodyWeight$[W]+$
$d11 \times$age$[Age]+e11$ \quad expression 14 wherein a10, a11, b10, b11, c10, c11, d10, d11, e10 and e11 are regression coefficients and constants.

Measurement of the reference volume for the subcutaneous fat tissue volume FS used in the calibration curve (regression formula) is a tissue volume obtained by integrating CSA (tissue cross-sectional area) for each slice obtained by MRI or X-ray CT in the longitudinal direction or CSA from one slice of the navel site or the like. The tissue volume can be converted into a tissue amount by converting tissue density information known by previous research papers and the like into weight.

6. Estimation of Trunk Visceral Fat/Subcutaneous Fat Ratio [V/S] (Part 1)

(10) A visceral fat/subcutaneous fat ratio [V/S] can be determined from a subcutaneous fat tissue volume [AFS] from the expressions 13 and 14 and a visceral fat tissue volume [AFV] from the expression 10.

$$V/S=AFV/AFS \quad \text{expression 15}$$

7. Determination of Abnormality in Splanchnic Organ Tissues by Impedance of Trunk (Middle Portion)

(11) The impedance Ztm of the trunk which is required to estimate the visceral fat tissue volume requires measurement of information of high stability and reliability because the trunk is a body part which changes significantly by breathing and drinking and eating. Thus, highly reliable impedance information of the trunk can be secured by performing the following processes. Further, determination of tissue abnormality in the trunk is also possible from the viewpoint as information associated with disturbance in body fluid distribution in the trunk.

(12) Process of Removing Influence of Change by Breathing (a) The impedance of the trunk is measured in a sampling period which is shorter than ½ of general breathing cycle time.

(b) Measured data in each sampling is subjected to a smoothing process by moving average or the like.
(c) The periodicity of breathing and the maximum and minimum values in each period are detected from the processed time-series data.
(d) The maximum value and the minimum value in each period are averaged, respectively.
(e) The averaged maximum value and the averaged minimum value are averaged to calculate the mean value of breathing.
(f) It is determined that the mean value of breathing has been confirmed at the point when the mean value of breathing in each breathing cycle enters a stable range within a predetermined number of times, and the impedance value of the confirmed median value is registered as the impedance value of the trunk, thereby ending the measurement.

(13) Process of Determining Abnormal Value by Drinking and Eating and Retention of Water (e.g. Urine) in Bladder or the like (a) An impedance of $26.7 \pm 4.8\Omega$ (mean±SD) of the trunk is a general value for a group.
(b) On the contrary, a value at the time of constipation or when urine is retained in the bladder or the stomach is filled with food and drink exceeds mean±3 SD.
(c) Thus, when a measured value exceeding 3 SD is obtained, a subject is informed of a possibility of the influence of drinking and eating, urine in the bladder and the like and is urged to make the measurement in the optimum environment. However, a subject showing different development of the skeletal muscle tissue layer and splanchnic organ tissues from standard sizes actually without their influence is urged to continue the measurement.
(d) Further, as a method of increasing determination sensitivity, the specified value is subdivided according to gender, body weights and body heights. Alternatively, the specified value is specified as a value per unit by dividing it by a body weight or a body height.

8. Measurement of Impedance of Skeletal Muscle Tissue Layer by Two Frequencies

(14) The skeletal muscle tissue layer of each body part is constituted by a mixture of spindle muscles whose muscle fiber direction is nearly straight with respect to the longitudinal direction and pinnate muscles whose muscle fibers run diagonally like bird's feathers and can achieve various functions.

(15) An indicator which indicates the electrical characteristic of the skeletal muscle tissue layer is volume-resistivity $\rho[\Omega \cdot cm]$. It has been reported that this value in the skeletal muscle tissue layer varies greatly depending on the muscle fiber direction and the value differs by $\rho 90°/\rho 0°=5$ to 10 times between when a current is passed in the muscle fiber direction and when a current is passed at 90° to the muscle fiber direction.

(16) Further, it has also been reported that this volume-resistivity has frequency characteristics and the sensitivity to muscle fibers becomes the highest in a frequency band around f1:50 kHz. That is, the spindle muscles and the pinnate muscles or even the pinnate muscles themselves differ in volume-resistivity depending on the pinnate angle, and when it is assumed that the current passing direction of a model in which muscles of particular characteristics exist in parallel is the longitudinal direction, a larger amount of a current passes through muscles with lower volume-resistivity, a smaller amount of a current passes through muscle with a larger pinnate angle, and combined impedance information of the measurement section is measured at sensitivity which is predominant over tissues allowing a large amount of a current to pass therethrough. It is said that a frequency band of f2:150 kHz higher than f1 or higher is hardly susceptible to the influence of the muscle fiber running direction. That is, impedance information indicating the entire skeletal muscle tissue layer in the measurement section can be obtained easily. However, although it can be said that f2 is more advantageous in measurement of skeletal muscle tissue volume, biased measurement sensitivity information obtained by f1 may be more advantageous in estimation of tissue information associated with body performance such as a body fat percentage.

9. Estimation from Two Frequency Impedance Measured Information of Trunk Skeletal Muscle Tissue Layer [ZMM] and Trunk Skeletal Muscle Tissue Cross-Sectional Area [AMM]

(17) The impedance of the trunk is measured by frequency f1 which is liable to be influenced in the muscle fiber running direction of the skeletal muscle tissue layer and frequency f2 which is not influenced in a frequency band higher than the frequency f1 and combined with body specifying information to specify the visceral fat tissue volume in the middle portion of the trunk. The skeletal muscle tissue layer has electrical frequency characteristics, and volume-resistivity $\rho[\Omega cm]$ indicating electrical characteristics changes greatly according to the running angle between the muscle fiber direction and the current passing direction. Further, it is said that the frequency showing high sensitivity to muscle fibers is around f1:50 kHz. Further, frequency which can penetrate muscle fibers and cell membranes indicates a stable volume-resistivity $\rho[\Omega cm]$ value which is not influenced by running of the cell membranes and muscle fibers. It is said that the stable frequency band is f2:150 kHz or higher. Even with 10 kHz, a certain level of stability can be secured as a relative characteristic to f1. Thus, use of a frequency band f1:50 kHz with the highest sensitivity to muscle fiber running and a high frequency band f2:150 kHz or higher (assumed to be 150 kHz in this case) which is not influenced by muscle fiber running is considered.

It is also said that stable frequency for cell membranes is higher than that for muscle fibers and is required to be about 250 kHz.

First, steps in the case of an electrical equivalent circuit for the trunk without the subcutaneous fat tissue layer of FIG. 5 will be described.

(18) [Step 1]
The impedances of the skeletal muscle tissue layer by the two frequencies are:
ZMM(f1): impedance of skeletal muscle tissue layer by f1, and
ZMM(f2): impedance of skeletal muscle tissue layer by f2.
In this case, it is assumed that the splanchnic organ tissues and the visceral fat tissues undergo no change in volume-resistivity in the frequency bands of f1 and f2.

The impedances of the trunk measured by the two frequencies are:
Ztm(f1): impedance of trunk by f1, and
Ztm(f2): impedance of trunk by f2.

The muscle fiber running frequency characteristic of the skeletal muscle tissue layer of the trunk can be represented by a nearly constant attenuation coefficient n, and the following expression holds.

$$ZMM(f1)/n=ZMM(f2) \quad \text{expression 16}$$

Thus, computation expressions are represented as follows.

$$Ztm(f1)=ZMM(f1)//(ZVM+ZFV)$$

$$1/Ztm(f1)=1/ZMM(f1)+1/[ZVM+ZFV] \quad \text{expression 17}$$

$$Ztm(f2)=ZMM(f2)//(ZVM+ZFV)$$

$$1/Ztm(f2)=1/ZMM(f2)+1/[ZVM+ZFV] \quad \text{expression 18}$$

The following expression can be obtained by substituting the expression 16 into the expression 18.

$$Ztm(f2)=[ZMM(f1)/n]//(ZVM+ZFV)$$

$$1/Ztm(f2)=1/[ZMM(f1)/n]+1/[ZVM+ZFV] \quad \text{expression 19}$$

The following expression can be obtained from the expressions 17 and 19.

$$1/[ZVM+ZFV]=1/Ztm(f1)-1/ZMM(f1)=1/Ztm(f2)-1/[ZMM(f1)/n] \quad \text{expression 20}$$

The following expression can be obtained from the expression 20.

$$1/ZMM(f1)=[1/Ztm(f2)-1/Ztm(f1)]/(n-1) \quad \text{expression 21}$$

The following expression can be obtained by substituting the expression 21 into the expression 17.

$$1/Ztm(f1)=[1/Ztm(f2)-1/Ztm(f1)]/(n-1)+1/[ZVM+ZFV] \quad \text{expression 22}$$

Thus, ZFV can be obtained as follows by transforming the expression 22.

$$ZFV=[(n-1)\times Ztm(f1)]/[n-Ztm(f1)/Ztm(f2)]-ZVM \quad \text{expression 23}$$

(19) [Step 2]

The impedance value measured by the frequency f2 of the skeletal muscle tissue layer of the trunk is information suitable for estimating the skeletal muscle tissue volume [MMtm] of the trunk. The reason is that in the case of the frequency f1, a difference in impedance sensitivity for each constituting muscle due to a difference in the muscle fiber running direction is conceived as an estimation error. Therefore, the impedance of the skeletal muscle tissue layer of the trunk can be expressed as follows by transforming the expression 8 by the expression 3.

$$ZMM(f2)=ZMM(f1)/n=[1/Ztm(f2)-1/Ztm(f1)]/[n\times(n-1)] \quad \text{expression 24}$$

Then, since the skeletal muscle tissue volume [MMtm] of the trunk is proportional to a body height H ($\propto$ length Lwt in the trunk width direction) and is inversely proportional to the impedance ZMM(f2) of the skeletal muscle tissue layer, it can be estimated by the following expression. A method for measuring the standard tissue volume for regression analysis of this expression is a volume by a cross-sectional area and integration processing of each slice by MRI and CT.

$$AMM=a0\times H/ZMM(f2)+b0 \quad \text{expression 25}$$

In the above expression, the information of the expression 24 is used as ZMM(f2).

10. Estimation of Subcutaneous Fat Tissue Volume [AFS] (Part 2)

(20) A method of measuring the subcutaneous fat tissue volume [AFS] of the trunk will be described.

To obtain subcutaneous fat tissue information (specifically, a voltage value or an impedance value), spreading resistance is used in this case. The spreading resistance has been generally considered unfavorable. In particular, since spreading resistance right underneath a current applying electrode represents information about the subcutaneous fat tissue layer, useful subcutaneous fat information can be obtained by measuring a voltage in this region.

To measure spreading resistance, at least a pair of current applying electrodes and at least a pair of voltage measuring electrodes capable of measuring a potential difference which occurs in a subject by a current applied from the current applying electrodes are provided. One of the current applying electrodes, for example, a current applying electrode, is used to apply a current to a body part where the subcutaneous fat tissue layer is thin or a body part having no or a little abdominal muscle portion of the skeletal muscle tissue layer, and the other current applying electrode (e.g. a current applying electrode 13L to be described later) is used to apply a current to a body part where the subcutaneous fat tissue layer is thick.

Meanwhile, voltage measuring electrodes included in the voltage measuring electrode pairs (e.g. voltage measuring electrodes 14La and 14Ra to be described later) are disposed at a site where the influence of spreading resistance right underneath the current applying electrode is dominant, i.e., in the vicinity of the current applying electrodes. On the other hand, the other voltage measuring electrodes (e.g. voltage measuring electrodes 14Lb and 14Rb to be described later) are disposed at a remote site where the influence of the spreading resistance right underneath the current applying electrode is weak, i.e., at a body part where the electrodes are not or hardly influenced by the subcutaneous fat tissue layer right underneath the current applying electrode. The former voltage measuring electrodes 14La and 14Ra may be disposed at a body part where fat is accumulated very thickly to the extent that the subcutaneous fat tissue layer reflects individual differences, such as around the navel, a lateral abdominal region (upper border of the iliac crest) or a lateral back region, and the latter voltage measuring electrodes 14Lb and 14Rb may be disposed at a body part where fat is liable to be accumulated and a body part where fat is hardly accumulated to the extent that the subcutaneous fat tissue layer reflects individual differences, e.g. between the navel and the upper border of the iliac crest (near the aponeurosis between the external abdominal oblique muscle and the rectus abdominis muscle).

The measurement values of potential differences V2 and V3 which occur between the voltage measuring electrodes (such as the voltage measuring electrodes 14La, 14Ra, 14Lb and 14Rb) by a current applied from the current applying electrodes are considered impedance information which is proportional to the impedance (ZFS) value of the subcutaneous fat portion and to the thickness ($L_{FS}$) information of the subcutaneous fat tissue layer. When the impedance of the spreading resistance is represented by $\Delta Z$ and a constant corresponding to the area of the current applying electrode is represented by A0, the following expression holds.

$$\Delta Z \propto ZFS \propto L_{FS}/A0 \propto L_{FS}$$

Thus, the cross-sectional area AFS of the subcutaneous fat tissue layer can be determined by the following expression.

$$AFS=Lw\times L_{FS}=aa0\times ZFS\times Lw+bb0 \quad \text{expression 26}$$

In the above expression, Lw represents abdominal circumferential length, i.e. the length of the circumference of the abdomen 16, and aa0 and bb0 are constants showing different values for a male and a female.

Measurement of the reference volume for the visceral fat tissue volume VM used in the calibration curve (regression formula) is a tissue volume obtained by integrating CSA (tissue cross-sectional area) for each slice obtained by MRI or X-ray CT in the longitudinal direction or CSA from one slice of the navel site or the like. The tissue volume can be converted into a tissue amount by converting tissue density information known by previous research papers and the like into weight.

11. Estimation of Trunk Visceral Fat/Subcutaneous Fat Ratio [V/S] (Part 2)

(21) A visceral fat/subcutaneous fat ratio [V/S] can be determined from the subcutaneous fat tissue volume [AFS] from the expression 26 and the visceral fat tissue volume [AFV] from the expression 10.

$$V/S=AFV/AFS \quad \text{expression 27}$$

First Embodiment

Next, examples of a trunk visceral fat measuring method and apparatus according to a first embodiment of the present invention will be described based on the above measurement principles of the present invention.

Figure 2:
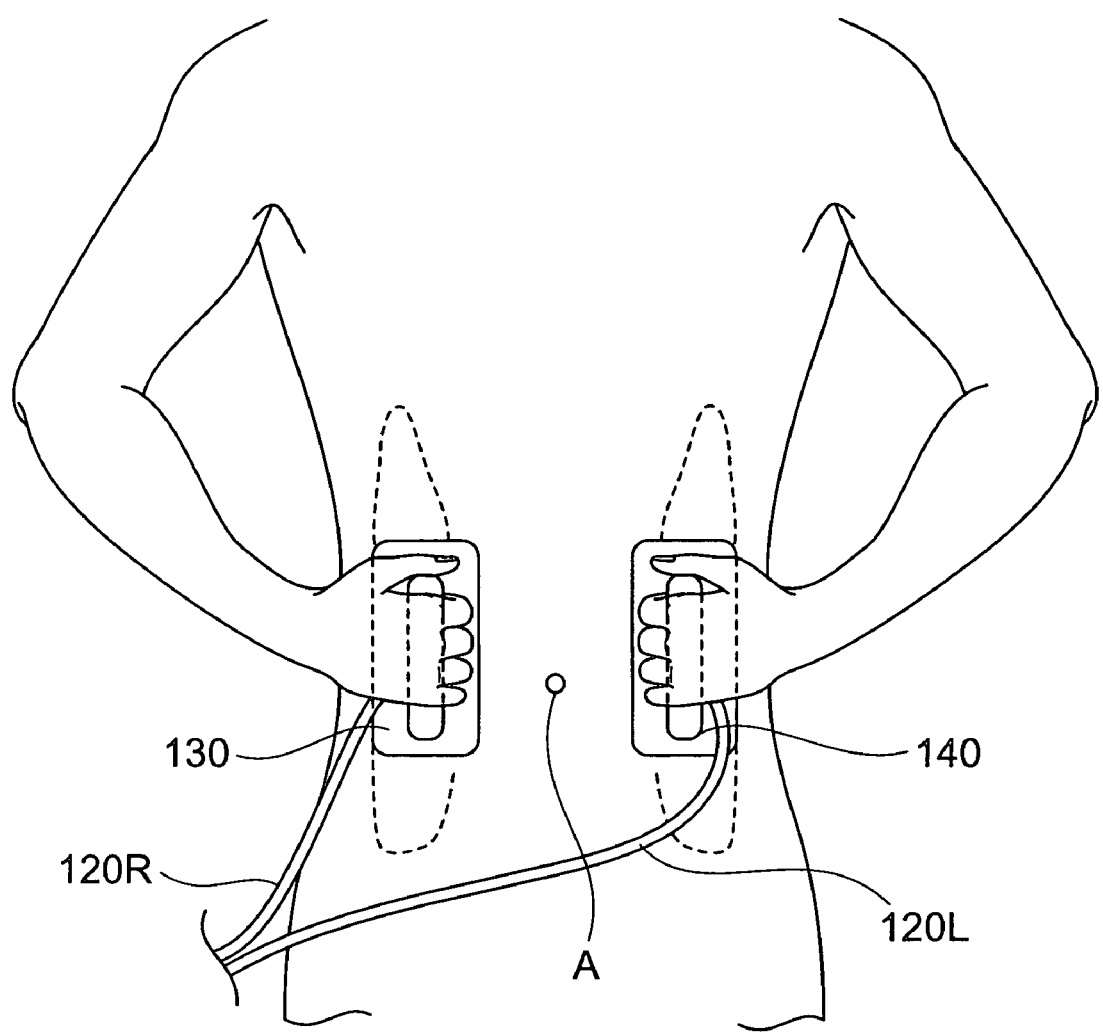
FIG. 2 is a diagram illustrating how to use the apparatus.
Figure 3:
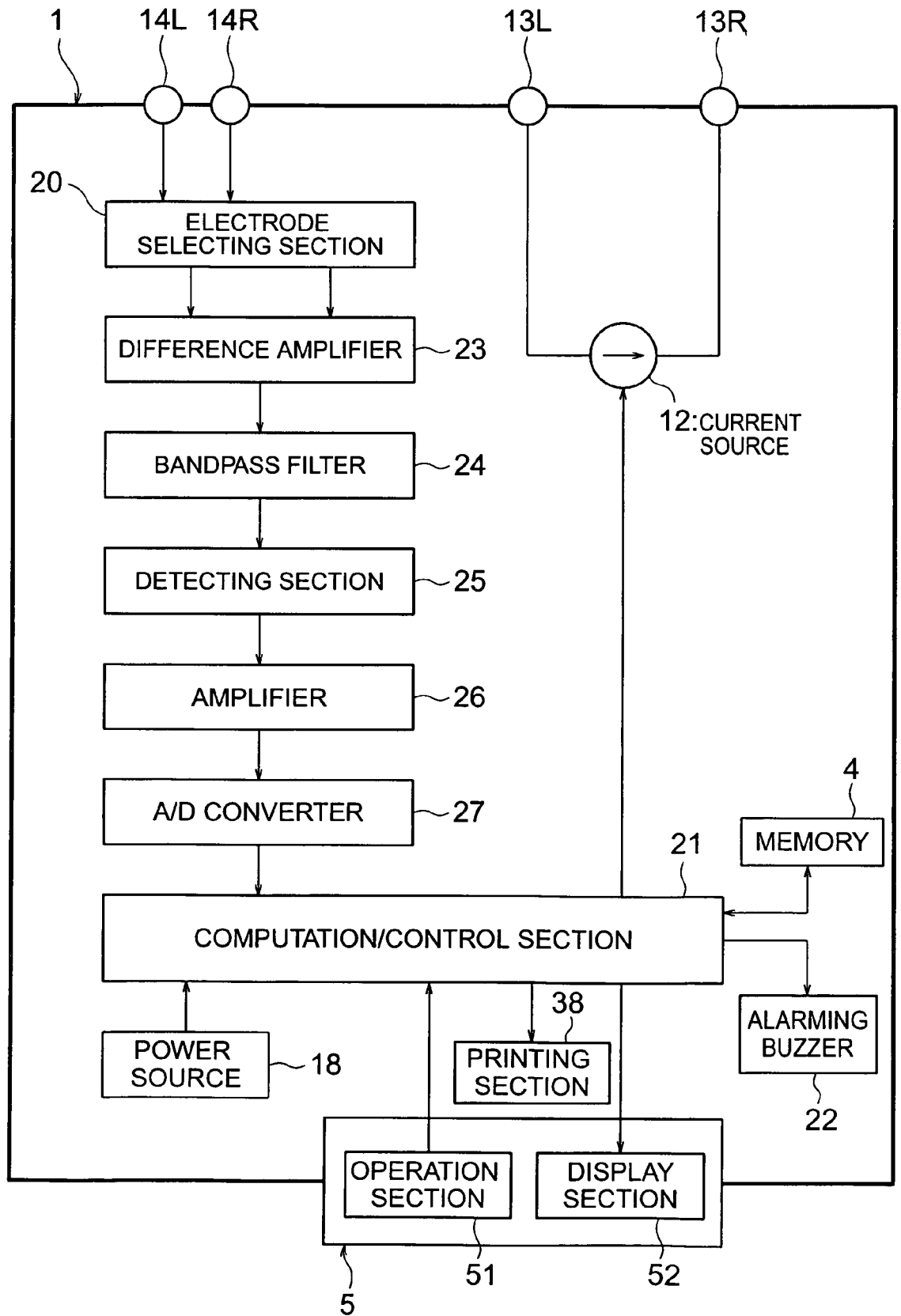
FIG. 3 is a block diagram illustrating the main unit of the trunk visceral fat measuring apparatus according to the first embodiment of the present invention.

FIG. 1 is a schematic perspective view of the appearance of an example of the trunk visceral fat measuring apparatus according to the first embodiment of the present invention, FIG. 2 is a diagram illustrating how to use the apparatus, and FIG. 3 is a block diagram showing a main unit included in the trunk visceral fat measuring apparatus according to the first embodiment.

The trunk visceral fat measuring apparatus 1 according to the first embodiment of the present invention comprises a main unit 11, and two grip electrodes 130 and 140 which are connected to the main unit 11 via cables 120L and 120R, when viewed from the outside. The grip electrodes 130 and 140 may be of handy type as shown in FIG. 2. When a subject actually uses the apparatus, he grips the grip electrodes 130 and 140 in the hands and presses the electrodes against a body part to be measured on his body, such as the abdomen.

On the front of the main unit 11, an operation section (input section) 51, an operation display panel 5 having a display section 52 and an alarming buzzer 22 are provided. In the main unit 11, as is obvious from FIG. 3, a computation/control section 21, a power source (power supply) 18, a storage section (memory) 4, a printing section 38, an impedance measuring section and the like are provided.

The operation section (input section) 51 can be used to input body specifying information including a body height and a body weight, for example. The operation display panel 5 displays various results, advice information and the like through the display section 52. This operation display panel 5 may be formed as a touch-panel type liquid crystal display resulting from integration of the operation section (input section) 51 and the display section 52.

The computation/control section 21 performs various inputs and outputs, measurements, computations and the like, such as computations of trunk skeletal muscle tissue cross-sectional area, trunk skeletal muscle tissue layer impedance, visceral fat tissue impedance, visceral fat tissue volume, splanchnic organ tissue volume, splanchnic organ tissue impedance, subcutaneous fat tissue volume, trunk visceral fat/subcutaneous fat ratio and the like based on body weight specifying information (such as a body weight) input from the operation section (input section) 51, measured impedances and the expressions 1 to 15, a process of removing the influence of change by breathing, a process of determining abnormality in splanchnic organ tissues, and the like.

The power source 18 supplies electric power to the sections in the electrical system of the present apparatus.

The storage section 4 stores not only body specifying information such as a body height and a trunk length and the above expressions 1 to 15 but also appropriate messages for health guideline advice as will be described later.

The printing section 38 prints various results, advice information and the like which are displayed on the display section 52.

The impedance measuring section comprises current applying electrodes 13L and 13R for applying a current to a body part to be measured of a subject, voltage measuring electrodes 14L and 14R for measuring a potential difference in the body part to be measured of the subject, a current source 12 for supplying a current to the current applying electrodes 13, an electrode selecting section 20 for selecting an electrode when three or more (not shown) voltage measuring electrodes 14 exist, a difference amplifier 23 for amplifying a measured potential difference, a bandpass filter 24 for filtering, a detecting section 25, an amplifier 26, and an A/D converter 27.

On the contact surfaces of the grip electrodes 130 and 140, the current applying electrodes 13R and 13L are provided in the lower portion and the voltage measuring electrodes 14R and 14L are provided in the upper portion, respectively.

The current applying electrodes 13R and 13L and the voltage measuring electrodes 14R and 14L may be implemented by metal-plating the surfaces of an SUS material and a resin material, for example. In the electrodes of this type, the surfaces of the metal electrodes are coated with a water-retentive polymer film, so that the electrodes are used in measurement after sprayed or wetted with water. By being wetted with water, the electrodes can secure stability in electrical contact with the skin. Further, although not particularly shown, electrodes of stickable type can also be used. These secure stability in contact with the skin by attaching a replaceable adhesive pad to the base electrode surfaces of the electrodes. The electrodes of this type are commonly used in low-frequency therapy equipment or as electrodes for electrocardiograms. They are classified into a disposable form which is removed and disposed after measurement and a form which is disposed and replaced only when the pad surface had become dirty and lost adhesiveness or water has evaporated and protected by a cover sheet until disposed.

Figure 4:
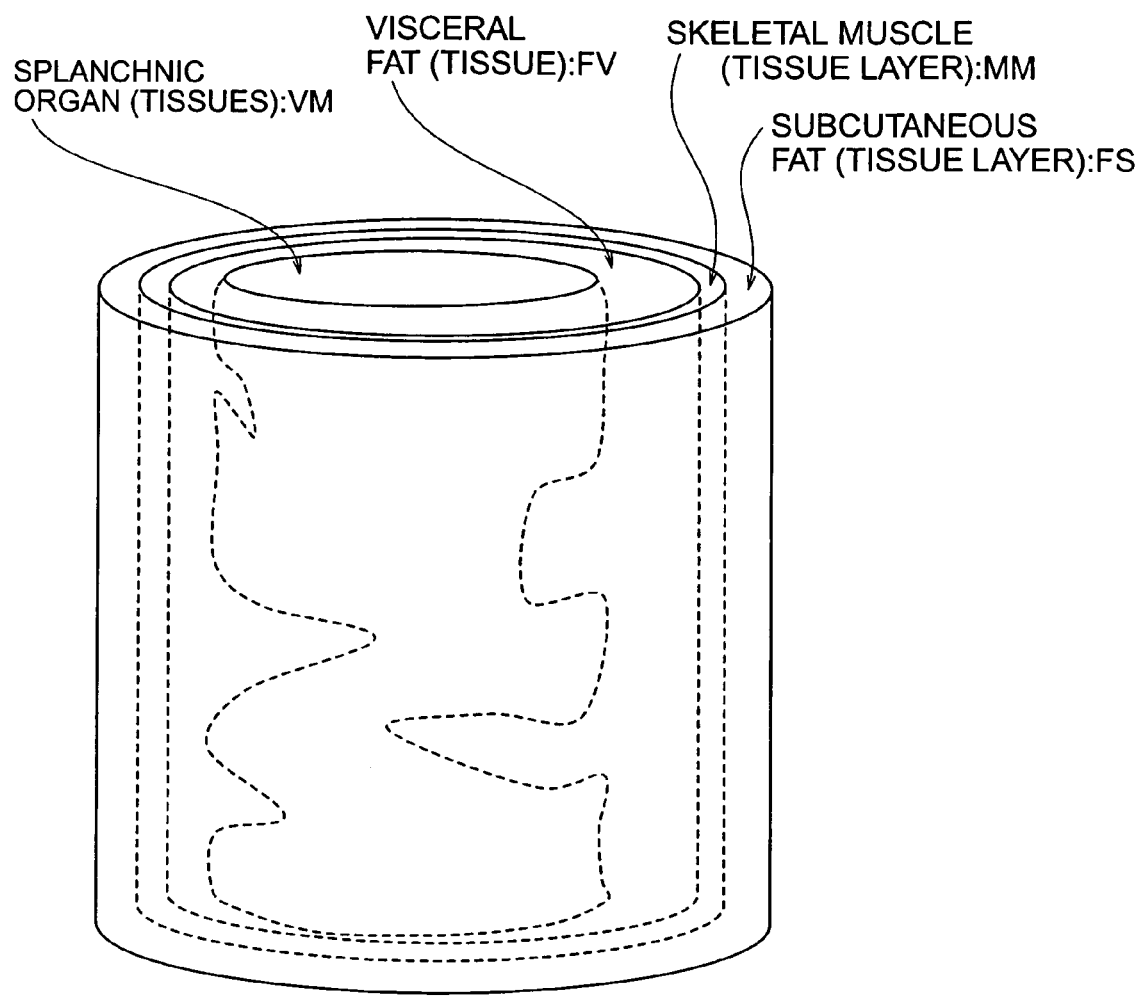
FIG. 4 is a schematic diagram illustrating the structure of the abdominal region of the trunk.

To describe the principles of the present invention, an electrical equivalent circuit model is introduced. FIG. 4 is a diagram which schematically shows the structure of the trunk (abdomen) on which this equivalent circuit is based. From the viewpoint of electrical characteristics, the trunk can be divided into a subcutaneous fat tissue layer (FS), a skeletal muscle tissue layer (MM), splanchnic organ tissues (VM) and visceral fat tissues (FV) which adhere between the splanchnic organ tissues.

Figure 5:
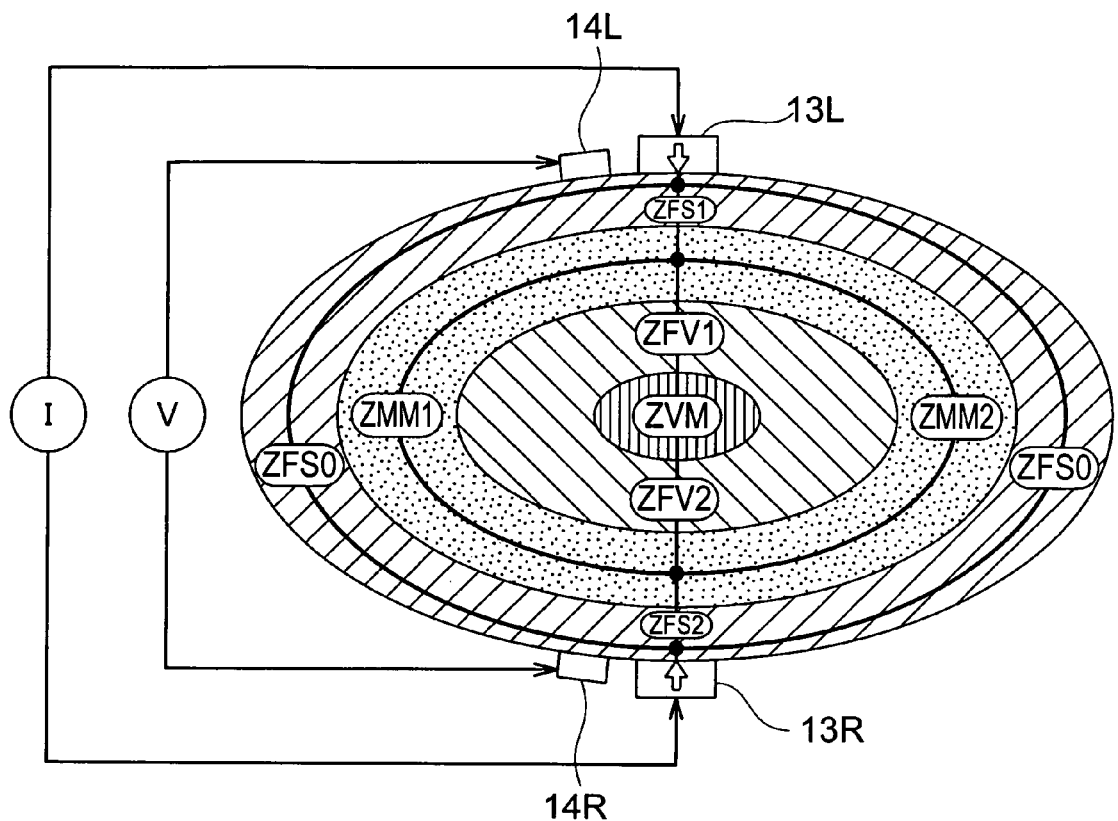
FIG. 5 is a cross-sectional view of the abdomen at the navel height of the trunk shown in FIG. 4.

FIG. 5 is a cross-sectional view at the navel height of the trunk shown in FIG. 4. As shown in this drawing, the cross section of the trunk includes the outermost subcutaneous fat tissue layer (FS), the skeletal muscle tissue layer (MM) which is situated immediately medial to the subcutaneous fat tissue layer (FS), the innermost splanchnic organ tissues (VM) and the visceral fat tissues (FV) which surround the splanchnic organ tissues (VM).

Figure 6:
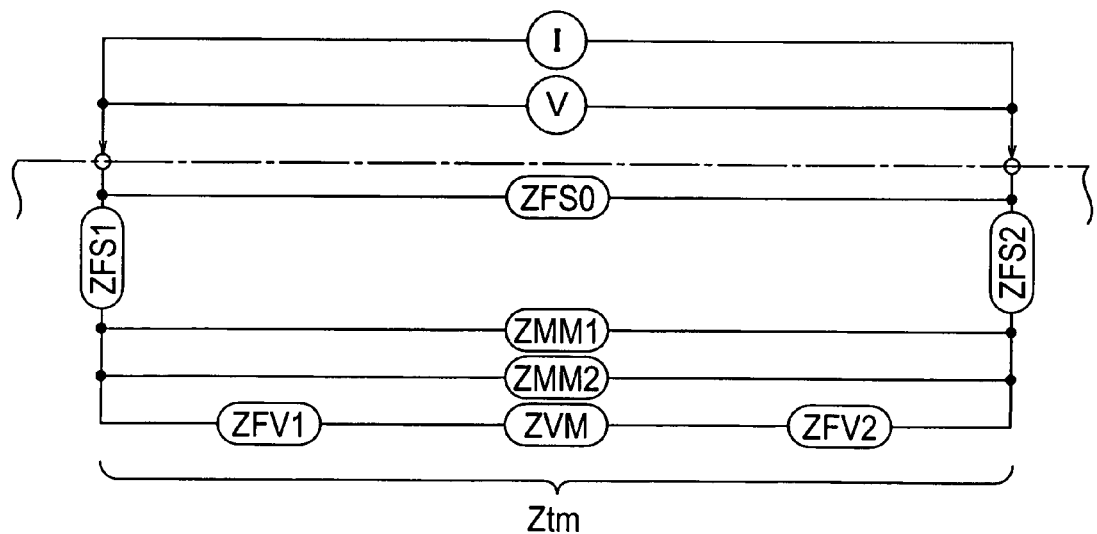
FIG. 6 is a diagram illustrating the model diagram of FIG. 5 as an electrical equivalent circuit.

FIG. 6 is a diagram showing the schematic diagram shown in FIG. 5 as an electrical equivalent circuit. For example, when a current (I) is applied from the current applying electrodes 13L and 13R and a potential difference (V) is measured by the voltage measuring electrodes 14L and 14R, electrical resistances in this equivalent circuit appear primarily as the impedances (ZFS1, ZFS2) of the subcutaneous fat tissue layer on the front and back sides of the navel, the impedance (ZFS0) of the subcutaneous fat tissue layer around the abdomen, the impedances (ZMM1, ZMM2) of the skeletal muscle tissue layer on the left and right sides of the navel, the impedances (ZFV1, ZFV2) of the visceral fat tissues on the front and back sides of the navel, and the impedance (ZVM) of the splanchnic organ tissues in the middle of the trunk.

Figure 7:
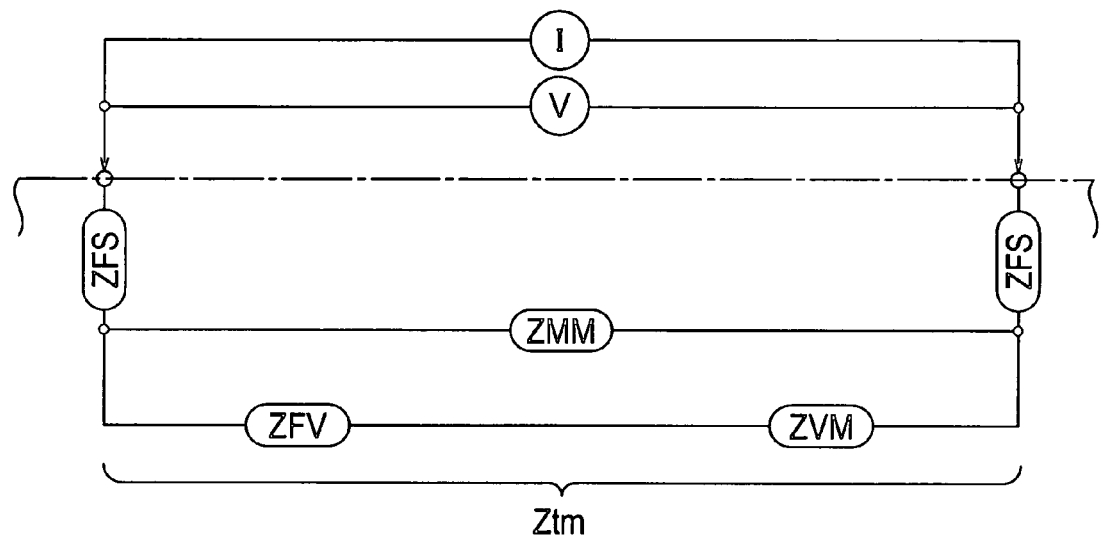
FIG. 7 is a diagram illustrating the circuit of FIG. 6 in a simplified form.

FIG. 7 is a diagram showing the circuit of FIG. 6 in a more simplified form. Since ZFS1 and ZFS2 are thought to have nearly the same size, they are indicated as the same value ZFS in this case, and ZMM1 and ZMM2 or ZFV1 and ZFV2 are indicated as ZMM and ZFV, respectively. Further, ZFS0 is omitted since its electrical conductivity is thought to be significantly lower than those of other regions. It should be clear from the description in the above section (1) in "1. Formation of Electrical Equivalent Circuit Model of Trunk Constituting Tissues" that ZFS0 can be omitted.

Figure 8:
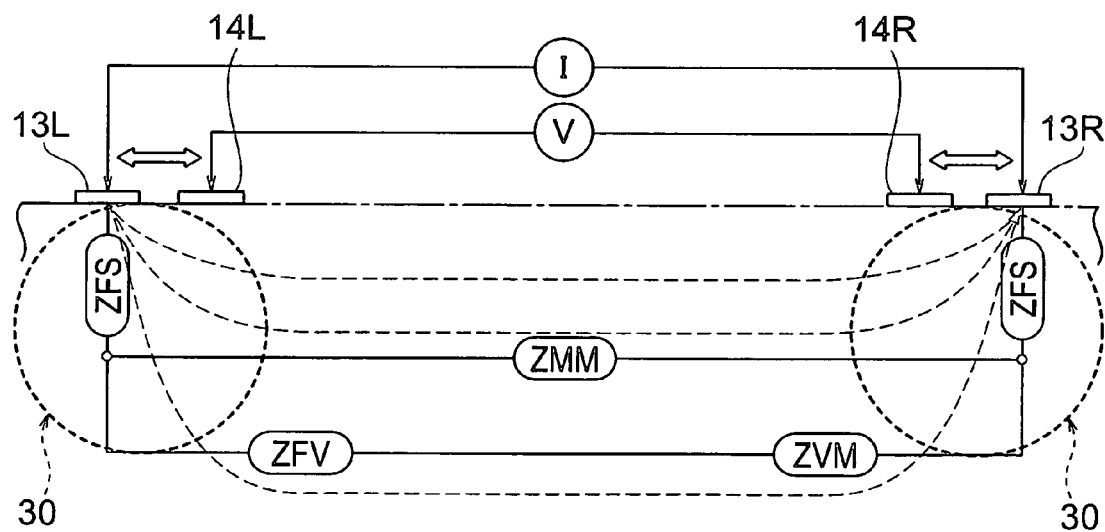
FIG. 8 is a diagram illustrating the relationship between the distance between the electrodes and spreading resistance.

Next, the relationship between the distance between the electrodes and spreading resistance in a four-electrode technique will be described with reference to FIG. 8. FIG. 8 is a diagram showing the relationship between the distance between the electrodes and spreading resistance. In FIG. 8, regions 30 circled in a dotted line indicate spreading resistance regions. Although a current from the current applying electrodes gradually spreads through the body of a subject after applied, the current spreads not so widely in the regions immediately after application, i.e. the spreading resistance regions. Therefore, current density in these regions becomes very high as compared with other regions. Accordingly, when the current applying electrodes 13 and the voltage measuring electrodes 14 are disposed very close to each other, a voltage measured by the voltage measuring electrodes 14 is influenced greatly by the current in the spreading resistance regions.

For example, as is obvious from the above expression 2, the impedance (ZFS) of the subcutaneous fat tissue layer around the navel, the impedance (ZFS0) of the subcutaneous fat tissue layer around the abdomen, the impedance (ZMM) of the skeletal muscle tissue layer, the impedance (ZFV) of the visceral fat tissues and the impedance (ZVM) of the splanchnic organ tissues in the middle of the trunk have the following relationship.

$$ZFS >> (ZVM+ZFV) >> ZMM$$

Therefore, a voltage measuring impedance $\Sigma Z1$ when the current applying electrodes and the voltage measuring electrodes are disposed very close to each other with almost no distance therebetween is expressed as follows.

$$\Sigma Z1 = 2 \times ZFS + ZMM // (ZVM+ZFV) \approx 2 \times ZFS$$

As is clear from this, since ZFS is amplified several times by the influence of spreading resistance, information by ZFS is dominant in this case.

To make the influence of spreading resistance small, the distance between the current applying electrodes and the voltage measuring electrodes must be large. For example, a voltage measuring impedance $\Sigma Z2$ when the current applying electrodes and the voltage measuring electrodes are disposed with a distance of about 10 cm therebetween is expressed as follows.

$$\Sigma Z2 \approx 2 \times ZFS + ZMM // (ZVM+ZFV)$$

As is obvious, although the influence of spreading resistance has been somewhat reduced by increasing the distance between the electrodes, the information by ZFS is still dominant.

Figure 9:
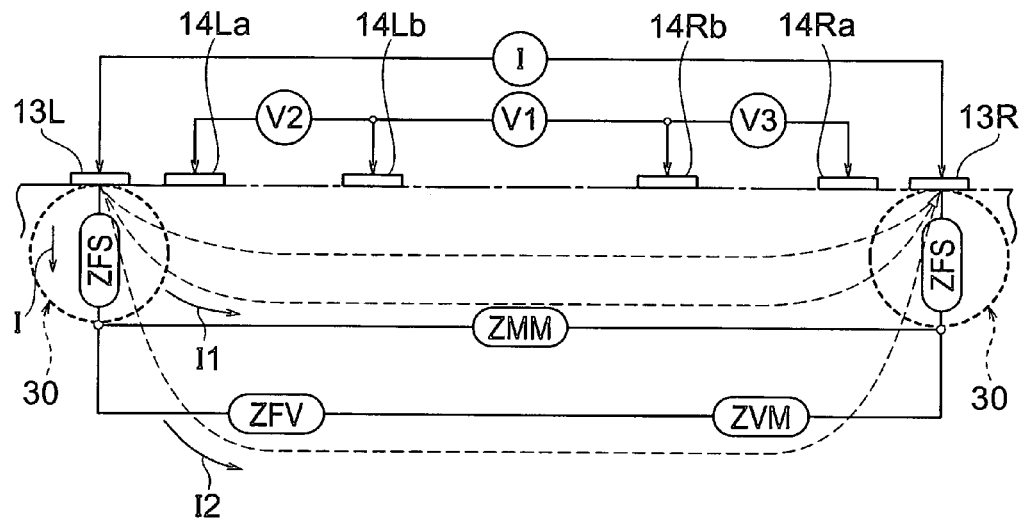
FIG. 9 is a diagram illustrating the relationship between the distance between the electrodes and spreading resistance.

To examine the influence of spreading resistance closely, a case where the electrodes 13L and 14Lb, the electrodes 14Lb and 14Rb, and the electrodes 14Rb and 13R are disposed with a distance of about 10 cm, i.e. about ⅓ of the distance between the electrodes 13L and 13R, therebetween, respectively, as shown in FIG. 9 is considered. However, the electrodes 14La and 14Ra are disposed very close to the electrodes 13L and 13R, respectively, with almost no distance therebetween. A voltage measuring impedance $\Sigma Z3$ in this case is expressed as follows.

$$\Sigma Z3 \approx 2 \times ZFS + ZMM // (ZVM+ZFV)$$

The relationship between voltage drops measured between the electrodes is roughly expressed as follows.

$$V1 = I \times ZMM // (ZVM+ZFV)$$

$$V2 = V3 = I \times 2 \times ZFS$$

$$V1:(V2+V3) \approx 1\sim2:10\sim20 = S:N$$

Variations such as 1~2 in S and 10~20 in N in the above expression are ascribable to an individual difference in the thickness of the subcutaneous fat tissue layer and the degree of development of the skeletal muscle tissue layer. As is understood from these results, it is not ensured that satisfactory S/N can be secured even if the distance between the electrodes is adjusted.

Further, since most of current passes predominantly through the skeletal muscle tissue layer, sufficient sensitivity of energization through a mixed tissue layer comprising splanchnic organ tissues and visceral fat tissues cannot be secured. That is, when a current passing through the skeletal muscle tissue layer is I1 and a current passing through the splanchnic organ tissues and visceral fat tissues to be measured is I2, the following expressions hold.

$$V1 = I \times ZMM // (ZVM+ZFV) = I1 \times ZMM = I2 \times (ZVM+ZFV)$$

$$I = I1 + I2$$

Therefore, the following expression holds.

$$ZMM:(ZVM+ZFV) = I2:I1 \approx 1:2 \text{ to } 5$$

As is clear from this, even if the influence of spreading resistance can be eliminated, the current passing through the skeletal muscle tissue layer is two to five times larger than the current passing through the splanchnic organ tissues and the visceral fat tissues, so that the S/N property further deteriorates. Thus, in a thick and short body part to be measured such as the trunk, an improvement in the S/N property is limited, because the upper limit is determined by the distance between the current electrodes even if the distance between the electrodes is adjusted.

Figure 10:
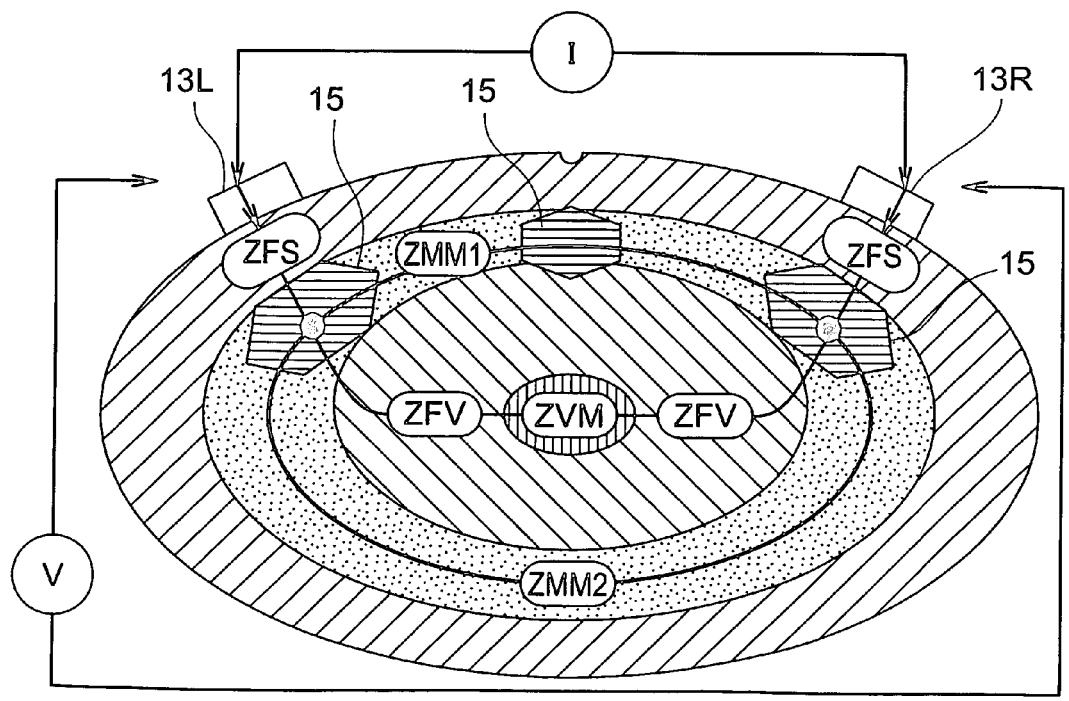
FIG. 10 is a schematic diagram illustrating an example of an electrode arrangement according to the first embodiment of the present invention with the structure of the abdomen of the trunk.

FIG. 10 shows an example of the electrode disposition method according to the present invention in the same manner as in FIG. 5. To secure an optimum S/N condition, the amounts of currents passing from the current applying electrodes 13L and 13R through the splanchnic organ tissues and visceral fat tissues under the skeletal muscle tissue layer are increased to secure the measurement sensitivity for the tissues to be measured. Further, a current is applied from a body part where the subcutaneous fat tissue layer is thin, in other words, a body part where the impedance (ZFS) of the subcutaneous fat tissue layer is small to minimize the influence of spreading resistance and improve the sensitivity of energization through the splanchnic organ tissues and the visceral fat tissues. To reduce the influence of the spreading resistance, measurement of potential difference by the voltage measuring electrodes 14L and 14R is preferably carried out in a body part where the influence of the subcutaneous fat tissue layer is small or the subcutaneous fat tissue layer is thin, in other words, a body part where the impedance (ZFS) of the subcutaneous fat tissue layer is small. Further, when an abdominal circumferential cross-sectional area is a measurement reference, a body part to which a current is applied from the current applying electrodes 13L and 13R is a body part where the subcutaneous fat tissue layer is deposited the most thinly or a skeletal muscle joining area where the skeletal muscle tissue layer has no or a thin muscle belly portion. An example thereof is a tendinous portion 15 (such as tendinous intersection 15A or aponeurosis 15R, 15L). More specifically, the body part is a section between the navel and the upper border of the iliac crest or a tendinous portion (aponeurosis) between the rectus abdominis muscle and the external abdominal oblique muscle.

Further, to secure the optimum S/N condition in the present invention, not all of the four electrodes are disposed on the abdominal circumference, but at least one of them is disposed off the abdominal circumference. By disposing the electrode off the navel circumference, the best distance condition can be secured, and the impedance (ZFS) of the subcutaneous fat tissue layer can be separated and removed as proper measurement of the four-electrode technique.

As such a disposition method, for example, it is conceivable to dispose the current applying electrodes on the abdominal (navel) circumference and dispose one or both of the voltage measuring electrodes off the abdominal (navel) circumference. Further, it is also possible to dispose one of the current applying electrodes on the abdominal (navel) circumference and dispose the other current applying electrode off the abdominal (navel) circumference. Further, the current applying electrodes or the voltage measuring electrodes may be disposed in the above sections, i.e. body parts where the subcutaneous fat tissue layer is thin, on the left and right sides when viewed with the navel A of a subject as the center therebetween. However, the voltage measuring electrodes are disposed in the trunk longitudinal direction within an abdominal region off the abdominal (navel) circumference.

Figure 11:
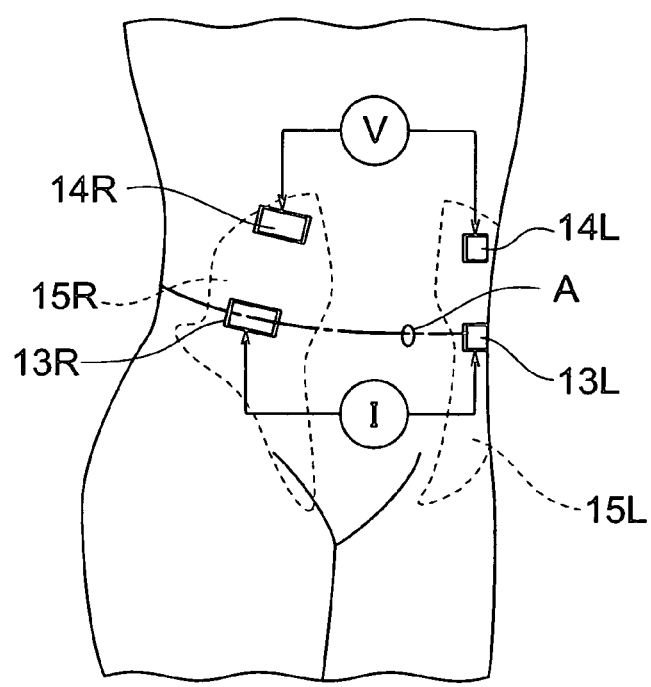
FIG. 11 is a diagram illustrating an example of the electrode arrangement.
Figure 12:
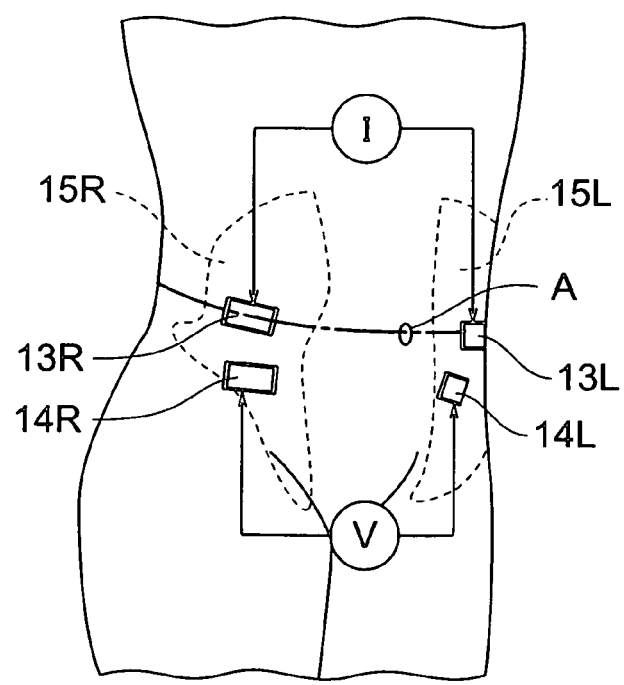
FIG. 12 is a diagram illustrating an example of the electrode arrangement.
Figure 13:
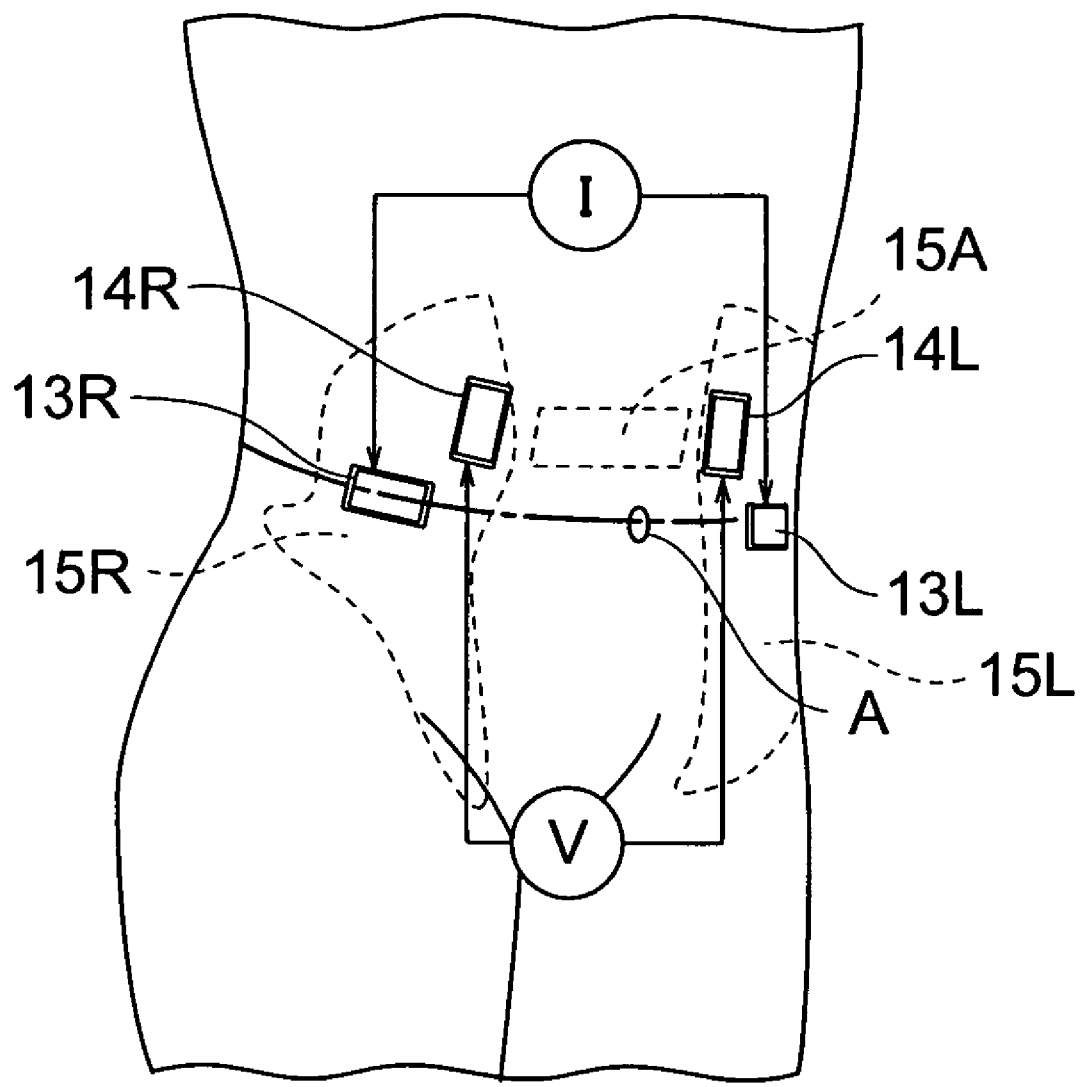
FIG. 13 is a diagram illustrating an example of the electrode arrangement.

FIGS. 11 to 13 show examples of actual electrode arrangements. FIG. 11 is a diagram showing the voltage measuring electrodes disposed above the navel circumference. FIG. 12 is a diagram showing the voltage measuring electrodes disposed below the navel circumference. FIG. 13 is a diagram showing the voltage measuring electrodes disposed above the navel circumference as in FIG. 11 and at the aponeurosis positions of tendinous intersection positions slightly above the navel A of the rectus abdominis muscle.

Next, the operations of the trunk visceral fat measuring apparatus in examples of the present invention shown in FIGS. 1 and 2 will be described with reference to a basic flowchart shown in FIG. 14 and subroutine flowcharts shown in FIGS. 15 to 20.

Figure 14:
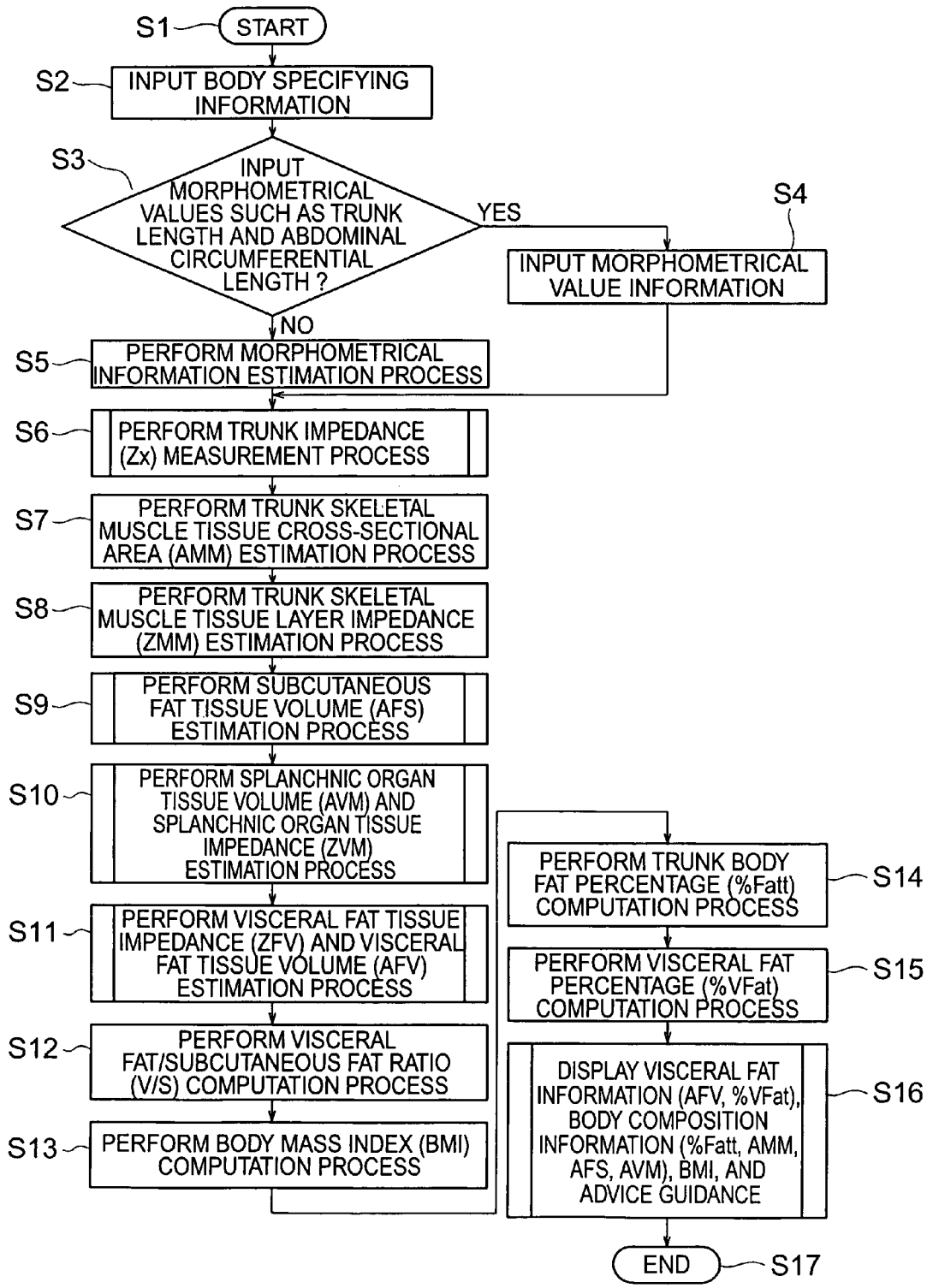
FIG. 14 is a diagram illustrating a basic flowchart for measuring the visceral fat of the trunk according to the first embodiment of the present invention.

In the basic flowchart shown in FIG. 14, firstly, when the power switch (not shown) in the operation section (input section) 51 is pressed, electric power is supplied from the power source 18 to the sections in the electrical system, and the display section 52 displays a screen for inputting body specifying information (such as a body height, a body weight, gender and age) including a body height (STEP S1).

Then, a user inputs a body height, a body weight, gender, age and the like from the operation section (input section) 51 in accordance with the above screen (STEP S2). In this case, although the body weight may be input from the operation section (input section) 51, it is also possible that data measured by a body weight measuring device (not shown) which is connected to the main unit 11 is automatically input and body weight specifying information (body weight) is calculated by the computation/control section 21. These input values are stored in the storage section 4.

Then, in STEP S3, it is determined whether morphometric measured values such as trunk length and abdominal circumferential length are to be input. When these morphometric measured values are to be input, morphometry is carried out and measured values of the trunk length, abdominal circumferential length and the like are input from the operation section (input section) 51 in STEP S4, and the computation/control section 21 then proceeds to STEP S6. When it is determined in STEP S3 that the morphometric measured values are not input, the computation/control section 21 proceeds to STEP S5. These input values are also stored in the storage section 4. Similarly, numerical value data and other data obtained in the following processes are also stored in the storage section 4.

In STEP S5, the computation/control section 21 performs a morphometrical information estimation process (for example, using a calibration curve prepared from human body information database) for estimating trunk length, abdominal circumferential length or the like from the body specifying information such as the body height, body weight, gender and age stored in the storage section 4.

Then, in STEP S6, a trunk impedance measurement process is carried out in the impedance measuring section. This trunk impedance measurement process will be described with reference to the subroutine flowchart shown in FIG. 18.

Then, in STEP S7, the computation/control section 21 performs a trunk skeletal muscle tissue cross-sectional area (AMM) estimation process. This computation is carried out based on the above expression 3 by using, for example, the body height H, body weight W and age Age stored in the storage section 4.

Then, in STEP S8, the computation/control section 21 performs a trunk skeletal muscle tissue layer impedance (ZMM) estimation process. This ZMM is estimated based on the above expression 4 by use of the body height H stored in the storage section 4 and the AMM estimated in STEP S7.

Then, in STEP S9, the computation/control section 21 performs a subcutaneous fat tissue volume (AFS) estimation process. This STEP S9 will be further described later with reference to the subroutine flowchart shown in FIG. 15.

In STEP S10, the computation/control section 21 performs a splanchnic organ tissue volume (AVM) and splanchnic organ tissue impedance (ZVM) estimation process. This STEP S10 will be further described later with reference to the subroutine flowchart shown in FIG. 16.

In STEP S11, the computation/control section 21 performs a visceral fat tissue impedance (ZFV) and visceral fat tissue volume (AFV) estimation process. This STEP S11 will be further described later with reference to the subroutine flowchart shown in FIG. 17.

Then, in STEP S12, the computation/control section 21 computes a visceral fat/subcutaneous fat ratio (V/S). This computation is carried out in accordance with the above expression 15 stored in the storage section 4.

Then, in STEP S13, the computation/control section 21 computes a body mass index (BMI). The body mass index can be calculated from the body weight W and body height H stored in the storage section 4 in accordance with the following expression.

$$BMI = W/H^2$$

Further, in STEP S14, the computation/control section 21 computes a trunk body fat percentage (% Fatt). The trunk body fat percentage can be calculated from the subcutaneous fat tissue volume (AFS), visceral fat tissue volume (AFV), trunk skeletal muscle cross-sectional area (AMM) and splanchnic organ tissue volume (AVM) stored in the storage section 4 in accordance with the following expression.

$$\%Fatt = (AFS + AFV)/[(AFS + AFV) + AMM + AVM] \times 100$$

Then, in STEP S15, the computation/control section 21 computes a visceral fat percentage (% VFat). The visceral fat percentage is calculated from the trunk body fat percentage (% Fatt) and visceral fat/subcutaneous fat ratio (V/S) calculated by the above computations and stored in the storage section 4 in accordance with the following expression.

$$\%VFat = \%Fatt \times (V/S)/[(V/S) + 1]$$

Finally, in STEP S16, the computation/control section 21 displays, in the display section 52, the visceral fat tissue information (AFV, % VFat), body composition information (% Fatt, AMM, AFS, AVM) and body mass index (BMI) obtained by the above computations and advice guidelines obtained by processes to be described later. Thereby, a series of processes are ended (STEP S17).

Figure 15:
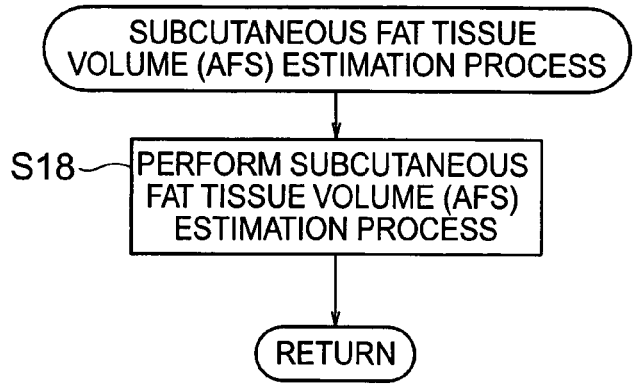
FIG. 15 is a diagram illustrating the process flow of estimation of subcutaneous fat tissue volume as a subroutine of the basic flow of FIG. 14.

Next, the above subcutaneous fat tissue volume (AFS) estimation process in STEP S9 will be described in detail with reference to the subroutine flowchart of FIG. 15. This estimation process is carried out in STEP S18 by use of the numerical values stored in the storage section 4 and the above expressions 13 and 14.

Figure 16:
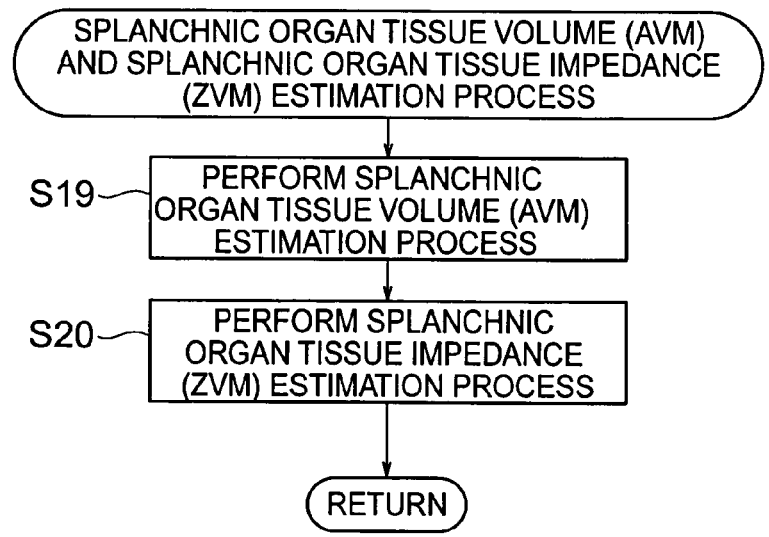
FIG. 16 is a diagram illustrating the process flow of estimation of splanchnic organ tissue volume and splanchnic organ tissue impedance as a subroutine of the basic flow of FIG. 14.

Next, the above splanchnic organ tissue volume (AVM) and splanchnic organ tissue impedance (ZVM) estimation process in STEP S10 will be described in detail with reference to the subroutine flowchart of FIG. 16. This estimation process is carried out by calculating a splanchnic organ tissue volume (AVM) in STEP S19 by use of the numerical values stored in the storage section 4 and the above expression 11 and calculating a splanchnic organ tissue impedance (ZVM) in STEP S20 by use of the numerical values stored in the storage section 4 and the above expression 12.

Figure 17:
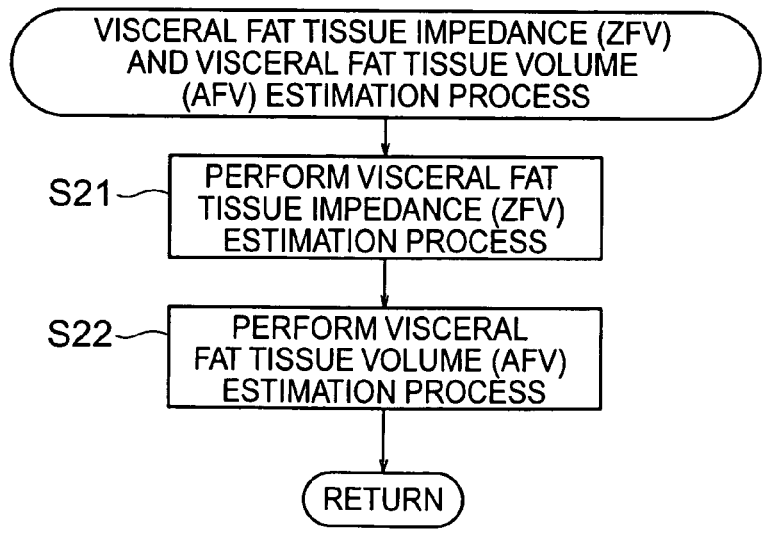
FIG. 17 is a diagram illustrating the process flow of estimation of visceral fat tissue impedance and visceral fat tissue volume as a subroutine of the basic flow of FIG. 14.

Next, the above visceral fat tissue impedance (ZFV) and visceral fat tissue volume (AFV) estimation process in STEP S11 will be described in detail with reference to the subroutine flowchart of FIG. 17. This estimation process is carried out by calculating a visceral fat tissue impedance (ZFV) in STEP S21 by use of the numerical values stored in the storage section 4 and the above expression 7 and calculating a visceral fat tissue volume (AFV) in STEP S22 by use of the body height H stored in the storage section 4, the calculated visceral fat tissue impedance (ZFV) and the above expression 10.

Figure 18:
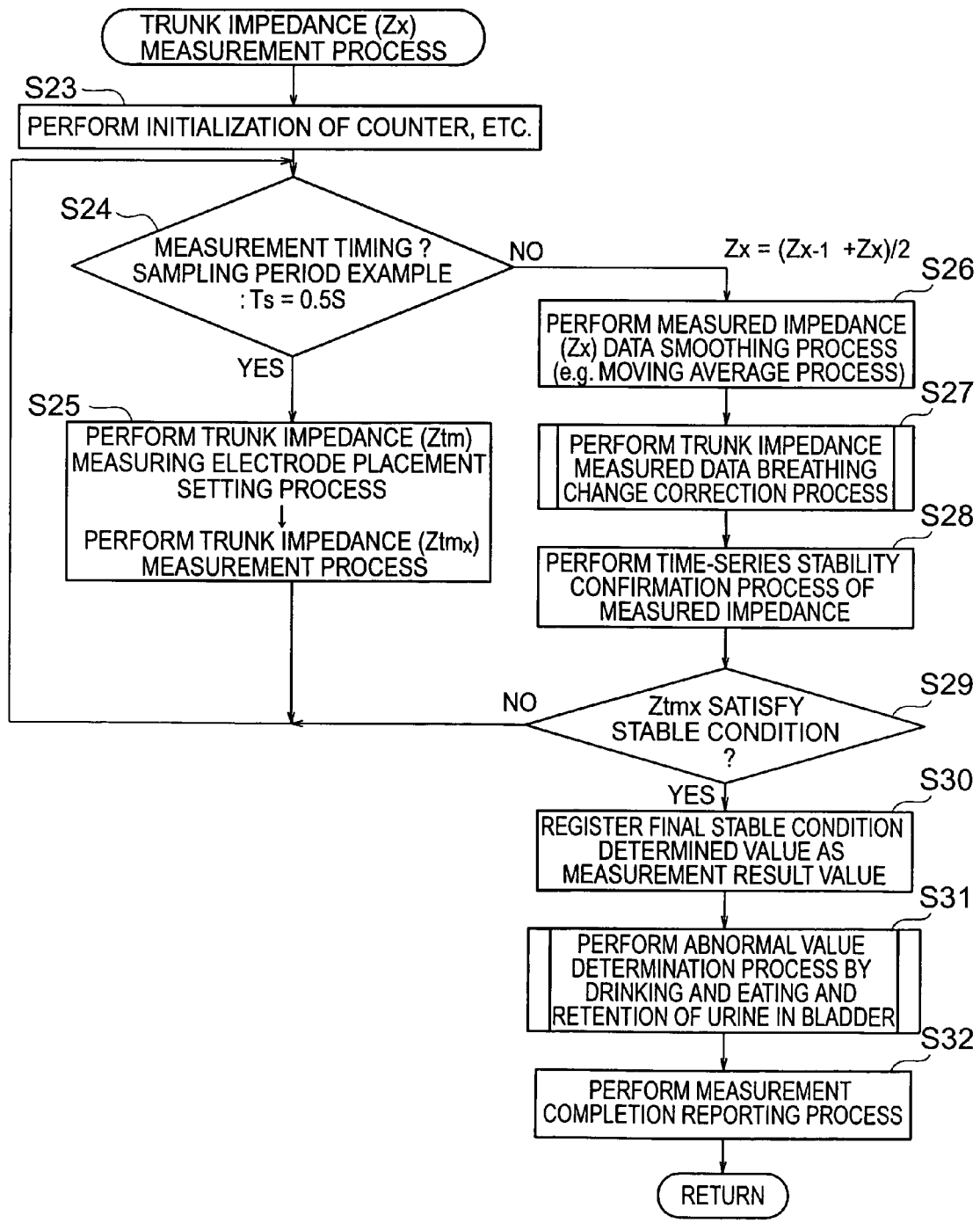
FIG. 18 is a diagram illustrating the process flow of measurement of the impedance of the trunk as a subroutine of the basic flow of FIG. 14.

Next, the trunk impedance measurement process in STEP S6 will be described in detail with reference to the subroutine flowchart of FIG. 18 showing a first embodiment. In this first embodiment, "process of removing influence of change by breathing" and "process of determining abnormal value by drinking and eating and retention of water (e.g. urine) in bladder or the like" as described in (12) and (13) in the above 7. are conducted. Firstly, in STEP S23, the computation/control section 21 initializes a counter, the number of samples for measurement data of the impedance Ztm of the trunk and a flag F. The flag F takes "1" or "0".

Then, in STEP S24, the computation/control section 21 determines whether it is measurement timing. When it has been determined that it is measurement timing, the computation/control section 21 performs a trunk impedance (Ztm) measuring electrode placement setting process and a trunk impedance ($Ztm_x$) measurement process in STEP S25.

Meanwhile, when it has been determined in STEP S24 that it is not measurement timing, the computation/control section 21 proceeds to STEP S26 and performs a measured impedance (Zx) data smoothing process (e.g. a moving average process). Then, in STEP S27, the computation/control section 21 performs a trunk impedance measured data breathing change correction process. This correction process will be further described later with reference to the subroutine chart of FIG. 19.

Then, in STEP S28, the computation/control section 21 performs a time-series stability confirmation process of measured impedance of each body part. This is carried out by determining whether each value after the trunk impedance measured data breathing change correction process in STEP S27 has converged to a value within a predetermined change in a predetermined number of times. In STEP S29, the computation/control section 21 determines whether the measured $Ztm_x$ satisfies a stable condition. This determination is made such that a median breathing value is determined at the point when a median breathing value in each breathing cycle enters a stable range within a predetermined number of times. When it is determined in this STEP S29 that the stable condition is satisfied, the computation/control section 21 proceeds to STEP S30 and registers the impedance value of the determined median value as the impedance value of the trunk and a final stable condition determined value as a measurement result value in the storage section 4. Meanwhile, when it is determined in STEP S29 that the stable condition is not satisfied, the computation/control section 21 returns to STEP S24 and repeats the above processes.

Subsequent to STEP S30, the computation/control section 21 performs an abnormal value determination process by drinking and eating and retention of urine in bladder in STEP S31 and informs completion of measurements by means of an alarming buzzer 22 (refer to FIG. 2), thereby completing measurements. The abnormal value determination process in STEP S31 will be further described later with reference to the subroutine flowchart of FIG. 20.

Figure 19:
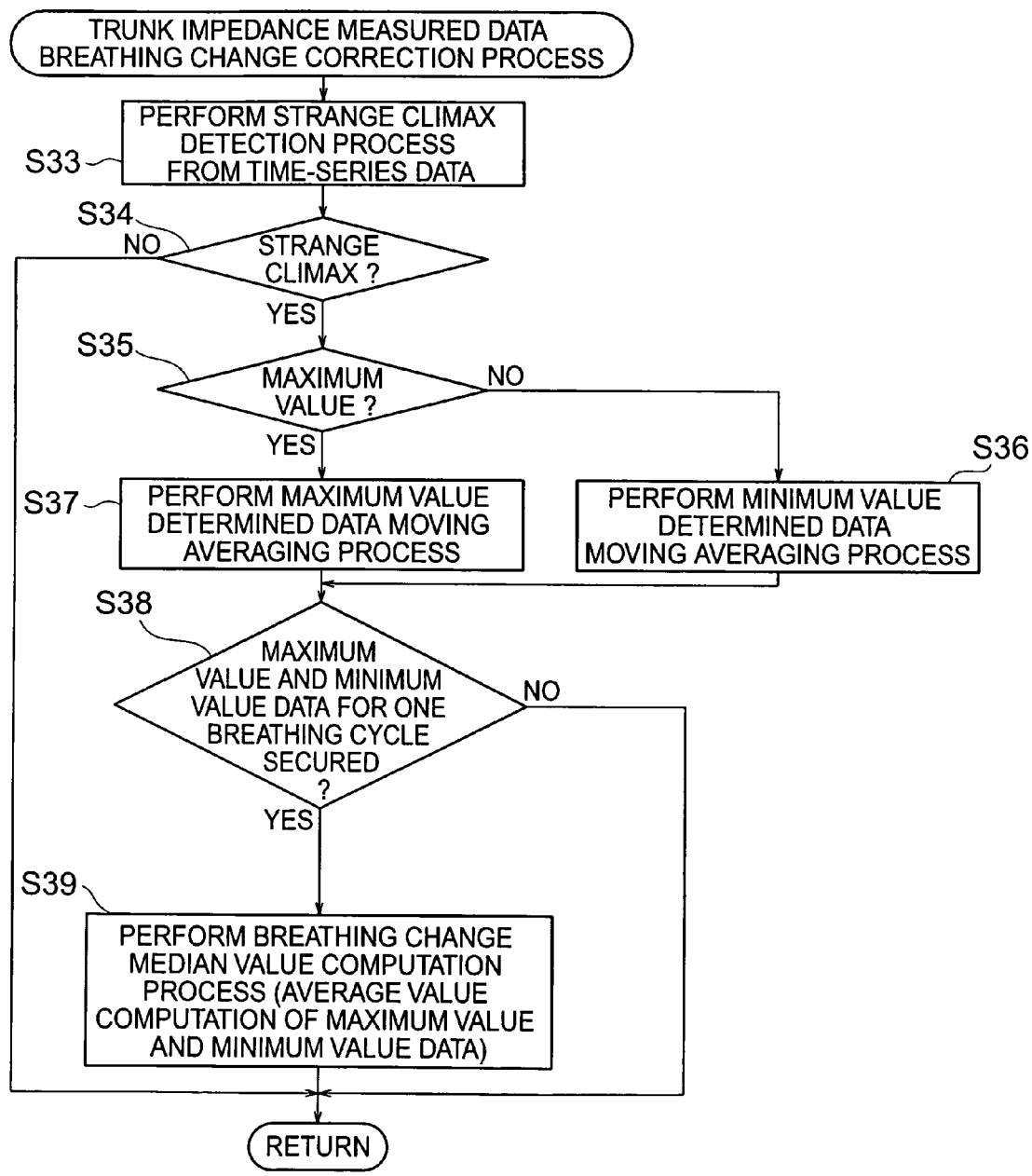
FIG. 19 is a diagram illustrating the process flow of correction of breathing change in the measured data of the impedance of the middle of the abdomen as a subroutine of the trunk impedance measurement process flow of FIG. 18.

Then, the trunk impedance measured data breathing change correction process in STEP S27 will be described in detail with reference to the subroutine flowchart of FIG. 19. Firstly, in STEP S33, the computation/control section 21 performs a strange climax detection process from the time-series data processed in STEP S27. In STEP S34, the computation/control section 21 determines whether it is a strange climax. This is carried out by detecting data of the point of polarity change of differential coefficients or differential values before and after the climax. When it is determined in STEP S34 that it is a strange climax, the computation/control section 21 proceeds to STEP S35 and determines whether it is the maximum value. This is a step of classifying the maximum value and the minimum value. When it is not the maximum value, a minimum value determined data moving averaging process is performed in STEP S36 in accordance with the following expression stored in the storage section 4.

$$[Ztm]\min_x \leftarrow ([Ztm]\min_{x-1} + [Ztm]\min_x)/2$$

When it is determined in STEP S35 that it is the maximum value, a maximum value determined data moving averaging process is performed in STEP S37 in accordance with the following expression stored in the storage section 4.

$$[Ztm]\max_x \leftarrow ([Ztm]\max_{x-1} + [Ztm]\max_x)/2$$

Then, in STEP S38, it is determined whether data of the maximum and minimum values for one breathing cycle has been secured. When it has been determined in STEP S38 that the data has been secured, a breathing change median value computation process (average value computation of maximum value and minimum value data) is performed in STEP S39 in accordance with the following expression stored in the storage section 4.

$$[Ztm]_x \leftarrow ([Ztm]\max_x + [Ztm]\min_x)/2$$

Next, the abnormal value determination process by drinking and eating and retention of urine in bladder in STEP S31 will be described in detail with reference to the subroutine flowchart of FIG. 20. Firstly, in STEP S40, the computation/control section 21 checks whether the trunk impedance (Ztm) is within a normal acceptable range, in accordance with the following expression stored in the storage section 4.

$$\text{Mean} - 3SD \leq Ztm \leq \text{Mean} + 3SD$$

In this case, 26.7±4.8 (Mean±SD) is conceivable as an example of acceptable value.

In STEP S41, it is determined whether the trunk impedance is within the acceptable range. When it is determined that the trunk impedance is not within the acceptable range, the computation/control section 21 proceeds to STEP S42 and performs a process of reporting a message about abnormality in the condition of the trunk (abdomen) and displays appropriate advice in the display section 52. As this advice, "Please prepare for defection or urination due to abnormal trunk condition." is conceivable, for example. Further, when the same determination result is obtained after the preparation, it is possible to complete the measurement by use of an abnormal value so as not to abort the measurement.

When it is determined in STEP S41 that the trunk impedance is within the acceptable range, the computation/control section 21 performs a process of reporting a message about normality in the condition of the trunk (abdomen) and displays appropriate advice in the display section 52 in STEP S43. As this advice, "The condition of the trunk is normal." is conceivable, for example.

According to the present invention, by the above operations, the visceral fat tissue information of the trunk (abdomen) can be obtained, the process of removing the influence of change by breathing and the process of determining abnormality by drinking and eating and retention of water (e.g. urine) in bladder or the like can be performed, and advice corresponding to the result of the abnormality determining process can be provided. Further, although trunk visceral fat tissue information is obtained as a fat percentage in the above embodiment, the present invention is not limited thereto and can obtain the information as a cross-sectional area, volume or weight by use of an appropriate conversion equation.

Figure 21:
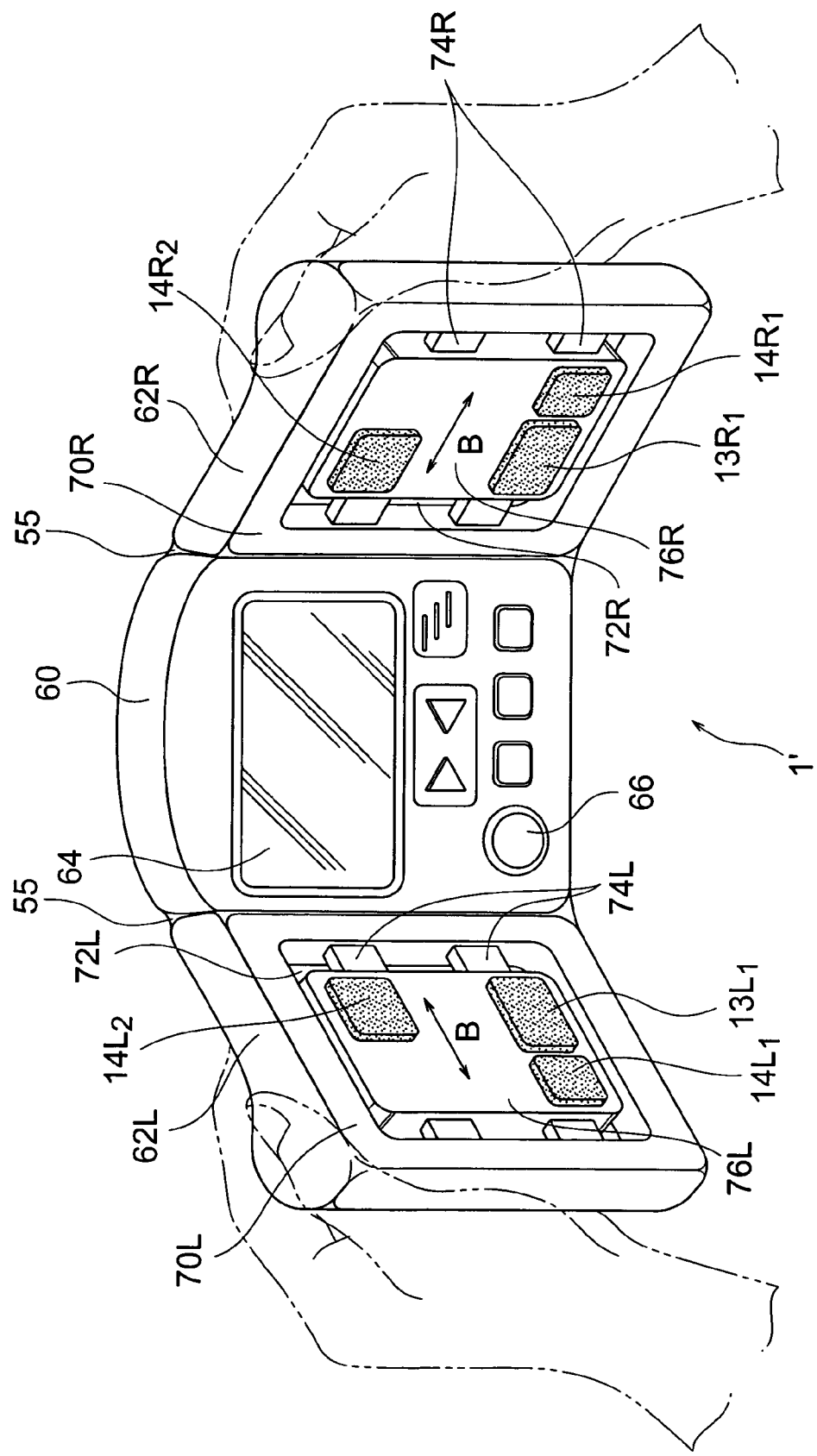
FIG. 21 is an external perspective view of a measuring apparatus according to another embodiment of the present invention.

FIG. 21 is an external perspective view of a variation of the measuring apparatus according to the first embodiment. The same members as those in the above embodiment are given the same numbers. The apparatus 1' in this variation comprises a main unit 60 which is somewhat curved to fit the shape of the abdomen of a subject and electrode supporting sections (grip electrode sections) 62R and 62L which are provided movably on the left and right sides of the main unit 60 by joints 55, in the form of a hinge, for example, so that they can bend toward the main unit 60 to some extent. As shown in FIG. 21, this apparatus 1' may be a handy type and can be used, for example, in such a manner that it is pressed against the abdomen of a subject with the electrode supporting sections 62R and 62L held by the left and right hands of the subject. Because the electrode supporting sections 62R and 62L are connected to the main unit 60 movably, the apparatus 1' fits the abdomen of the subject nicely.

The main unit 60 has a liquid crystal display section 64 and various switches 66 on its abdomen-contacting surface. Upon measurement, these components are positioned on the abdomen side of a subject. Therefore, although the subject cannot see the display section of the main unit 60 during measurement, he can see that after measurement by moving the unit away from the abdomen.

The electrode supporting sections 62 comprise supporting frames 70R and 70L having holes provided at the center, two parallel slide bars 74R which are provided horizontally in the hole 72R of the supporting frame 70R, two parallel slide bars 74L which are provided horizontally in the hole 72L of the supporting frame 70L, and slide supports 76R and 76L which are slidable along the slide bars 74R and 74L, respectively. On the top surfaces of the slide supports 76R and 76L, various electrodes to be disposed on the abdomen of a subject, i.e. a current applying electrode $13L_1$, voltage measuring electrodes $14L_1$ and $14L_2$, a current applying electrode $13R_1$, and voltage measuring electrodes $14R_1$ and $14R_2$.

Figure 25:
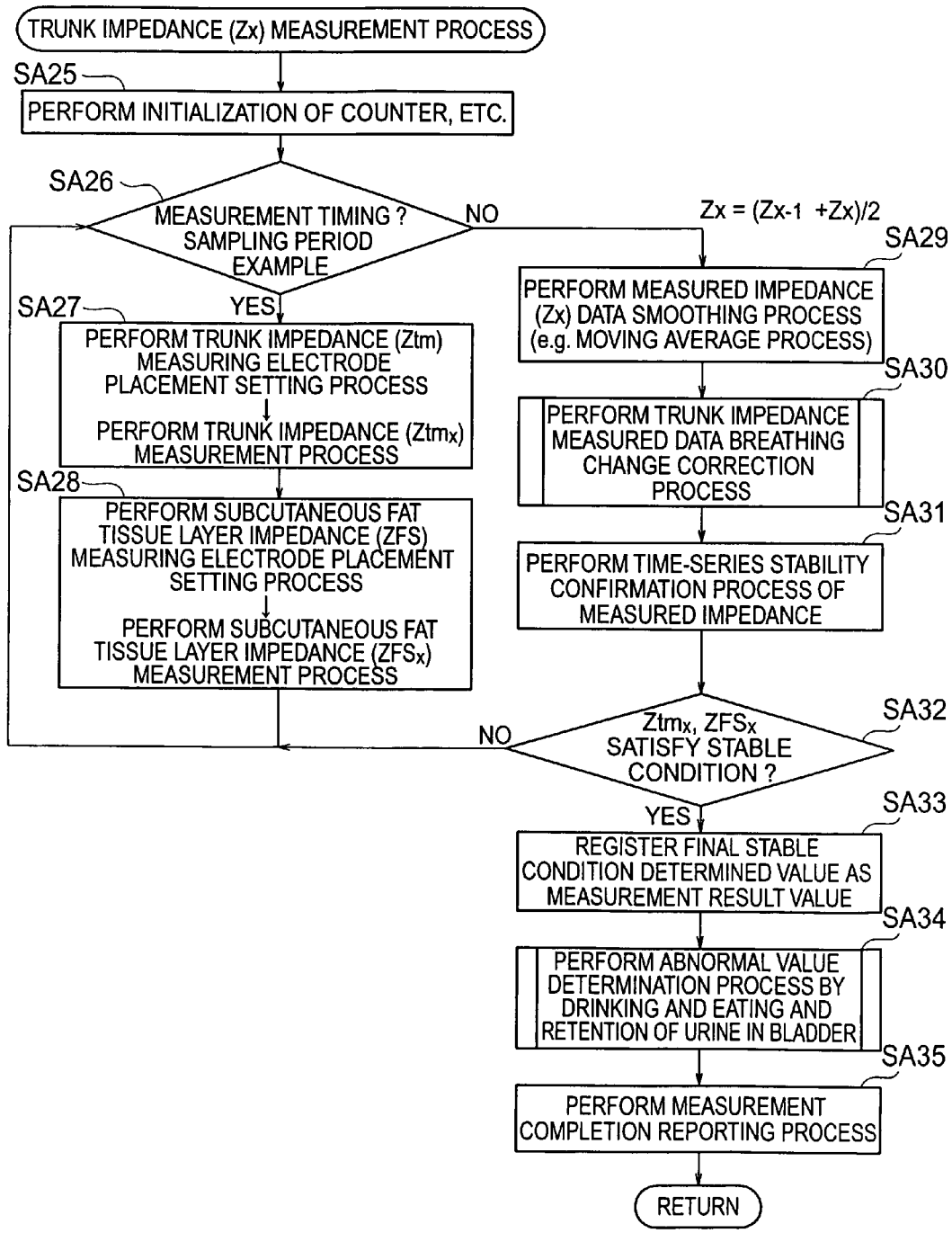
FIG. 25 is a diagram illustrating the process flow of measurement of the impedance of the trunk as a subroutine of the basic flow of FIG. 24.

The numbers and positions of the electrodes 13 and 14 are determined according to applications. In the example of FIG. 25, the electrodes are disposed in the same manner as in FIG. 1. As is obvious from the above constitution, according to the measuring apparatus 1' of the present embodiment, the electrodes 13 and 14 on the slide supports 76 can be set at various widths easily according to the size of the body of a subject by sliding the slide supports 76R and 76L in the directions indicated by arrows A in the drawing.

Second Embodiment

Next, an example of a trunk visceral fat measuring method and apparatus and trunk skeletal muscle volume measuring apparatus according to a second embodiment of the present invention will be described. In the following description and drawings, the same members as those in the first embodiment are given the same numbers.

Figure 22:
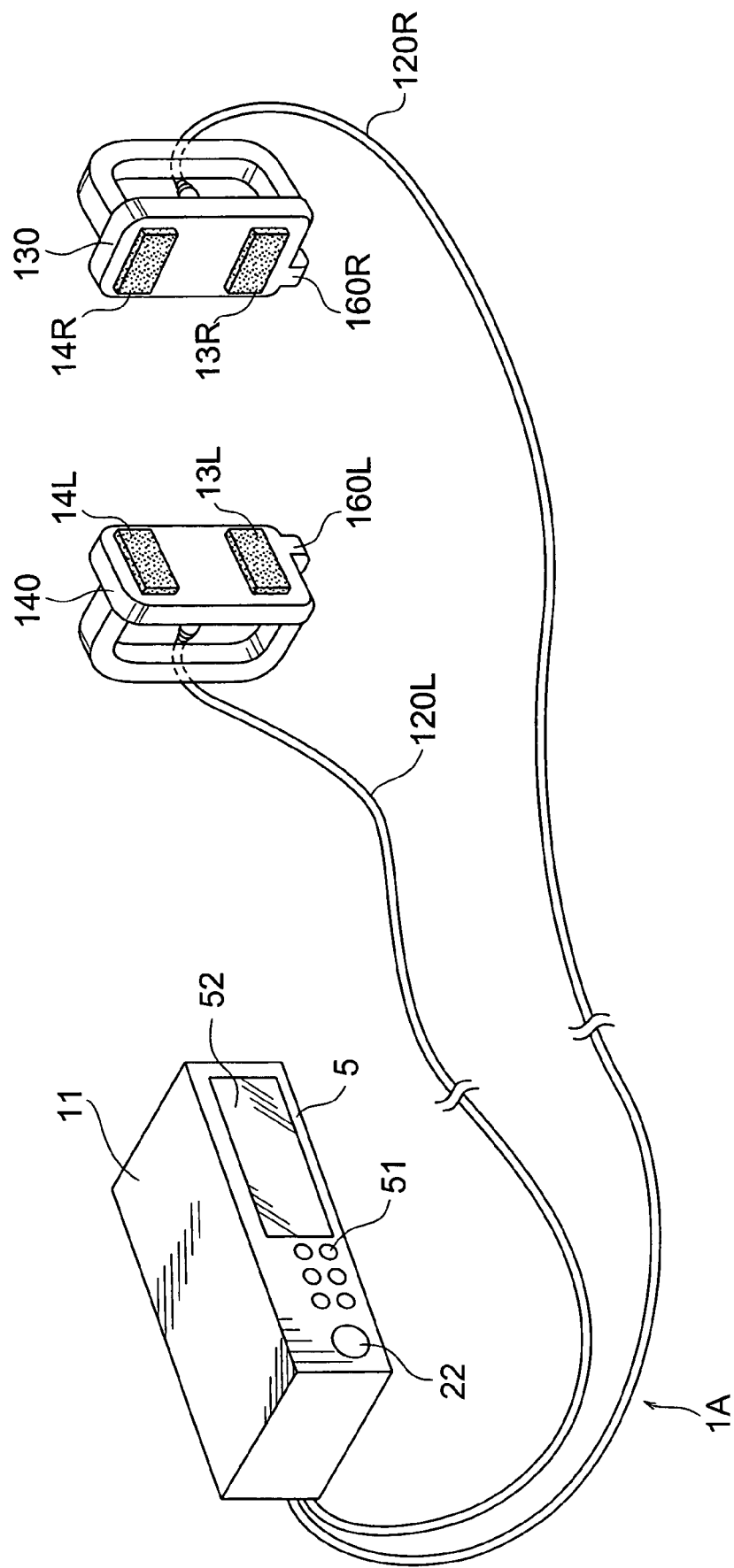
FIG. 22 is a schematic perspective view of the appearance of an example of a trunk visceral fat measuring apparatus according to a second embodiment of the present invention.
Figure 23:
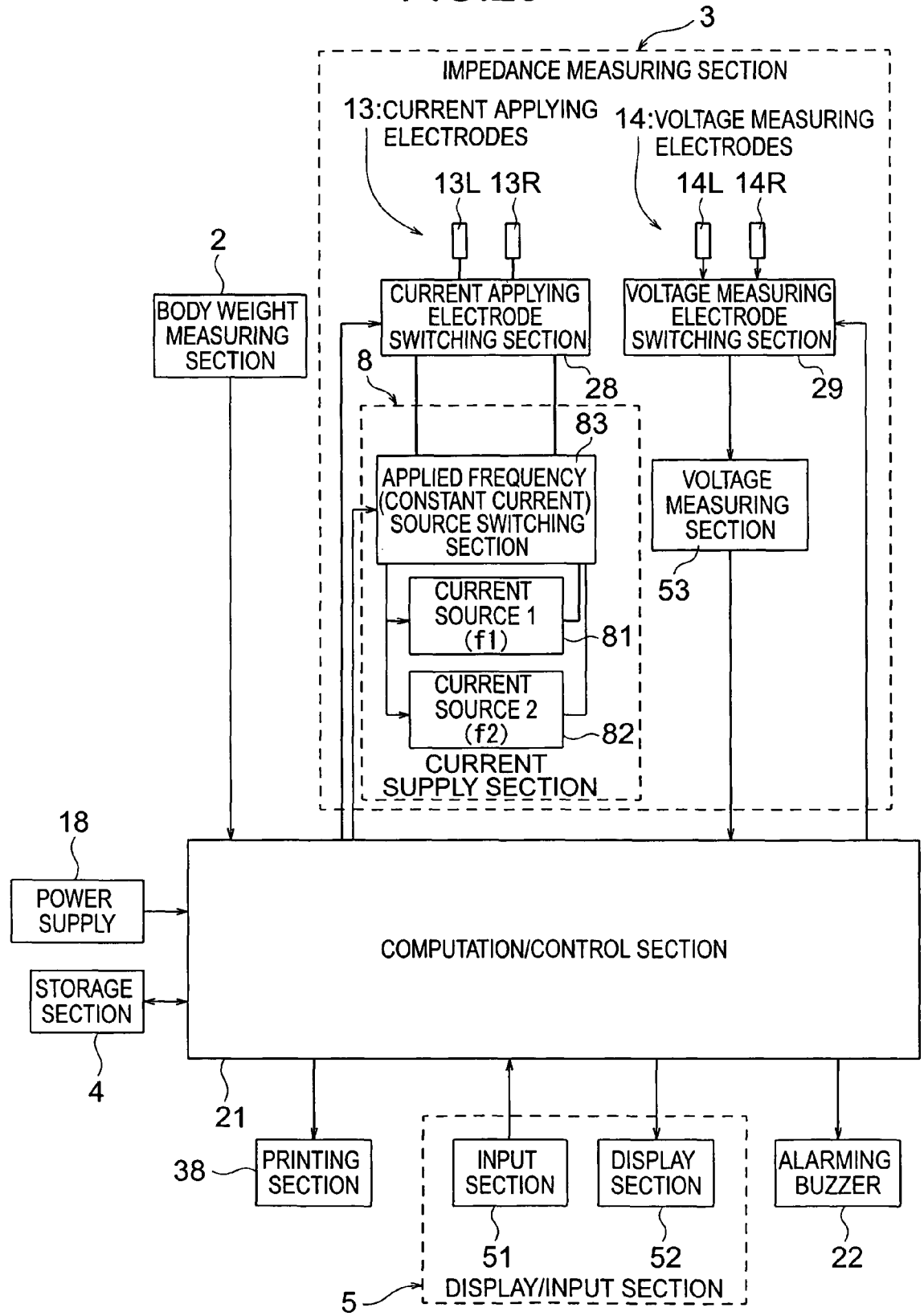
FIG. 23 is a block diagram illustrating the main unit of the trunk visceral fat measuring apparatus according to the second embodiment of the present invention.

FIG. 22 is a diagram corresponding to FIG. 1 and is a schematic perspective view of the appearance of an example of a trunk visceral fat measuring apparatus 1A according to the second embodiment of the present invention. FIG. 23 is a diagram corresponding to FIG. 3 and is a block diagram showing a main unit included in the trunk visceral fat measuring apparatus 1A according to the second embodiment.

As is obvious from FIG. 22, a primary difference in appearance between the apparatus 1 and the apparatus 1A is that the apparatus 1A has guides 160R and 160L. Thereby, in the apparatus 1A, electrodes can be pressed against the same positions all the time by placing the guides 160R and 160L on the pelvis (anterior superior iliac spine). Further, as is obvious from FIG. 23, a primary difference in constitution between the apparatus 1 and the apparatus 1A is that the apparatus 1A has an impedance measuring section 3 for two-frequency measurement in addition to a body weight measuring section 2.

A computation/control section 21 performs various inputs and outputs, measurements, computations and the like, such as computations of trunk skeletal muscle tissue cross-sectional area, trunk skeletal muscle tissue layer impedance, visceral fat tissue impedance, visceral fat tissue volume, splanchnic organ tissue volume, splanchnic organ tissue impedance, subcutaneous fat tissue volume, trunk visceral fat/subcutaneous fat ratio and the like based on body weight specifying information (such as a body weight) input from an input section 51, measured impedances and the expressions 1 to 27, a process of removing the influence of change by breathing, a process of determining abnormality in splanchnic organ tissues, and the like.

A storage section 4 stores not only body specifying information such as a body height and a trunk length and the above expressions 1 to 27 but also appropriate messages for health guideline advice.

The body weight measuring section 2 comprises a weight detecting section, an amplifying section and an AD converting section as in a known scale and measures a potential difference ascribable to body weight specifying information (weight). Although not shown in FIG. 22, the body weight measuring section 2 can be attached to or integrated with the apparatus of FIG. 22 as a unit having the same constitution as that of a general scale.

The impedance measuring section 3 comprises a current supplying section 8, a current applying electrode switching section 28, current applying electrodes 13 (13L, 13R), voltage measuring electrodes 14 (14L, 14R), a voltage measuring electrode switching section 29 and a voltage measuring section 53 and measures a potential difference ascribable to a bioelectrical impedance of each body part (impedance of each body part), as in a known bioelectrical impedance measuring apparatus (e.g. a body fat meter or a body composition meter).

The current supplying section 8 comprises a first current source 81 of frequency f1, a second current source 82 of frequency f2, and an applied frequency (constant current) source switching section 83. In the present embodiment, the frequency f1 is 50 kHz, and the frequency f2 is 150 kHz.

The current applying electrodes 13L and 13R and the voltage measuring electrodes 14L and 14R may be implemented by metal-plating the surfaces of an SUS material and a resin material, as in the case of the current applying electrodes 13R and 13L and the voltage measuring electrodes 14R and 14L in the first embodiment.

The principle of the present invention is the same as that described in the first embodiment with reference to FIGS. 4 to 10, and an example of actual disposition of the electrodes is the same as that described in the first embodiment with reference to FIGS. 11 to 13. Accordingly, descriptions thereof will be omitted.

Next, the operations of the trunk visceral fat measuring method and trunk skeletal muscle volume measuring apparatus in the present embodiment of the present invention shown in FIGS. 22 and 23 will be described with reference to FIGS. 16, 17, 19 and 20 of the first embodiment and a subroutine flowchart shown in FIG. 25 used in place of FIG. 18 of the first embodiment in addition to the basic flowchart shown in FIG. 24.

Figure 24:
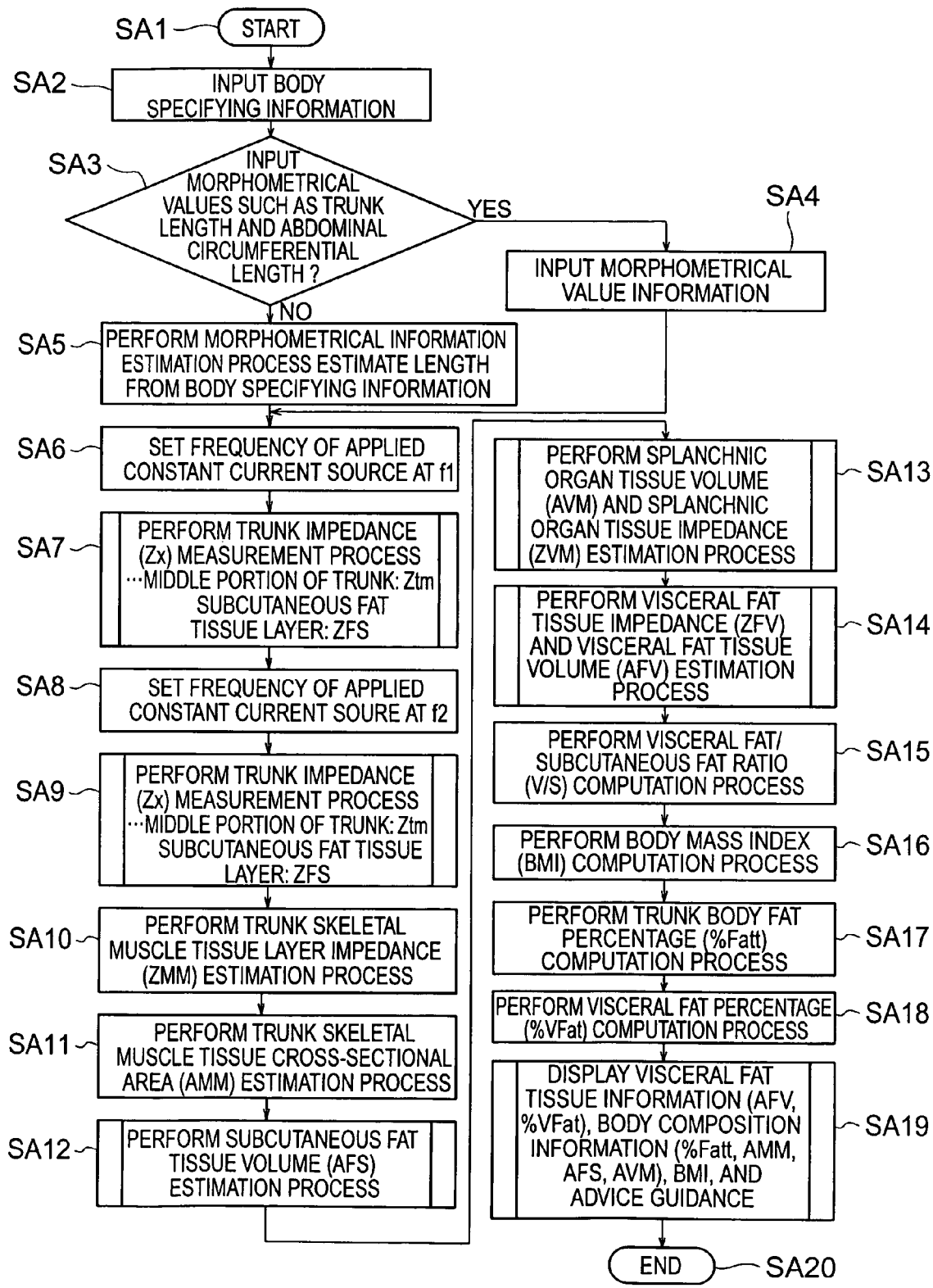
FIG. 24 is a diagram illustrating a basic flowchart for measuring the visceral fat of the trunk according to the second embodiment of the present invention.

In the basic flowchart shown in FIG. 24, firstly, when the power switch (not shown) in the input section 51 is pressed, electrical power is supplied from a power source 18 to the sections in the electrical system, and a display section 52 displays a screen for inputting body specifying information (such as a body height, a body weight, gender and age) including a body height (STEP SA1).

Then, a user inputs a body height, a body weight, gender, age and the like from the input section 51 in accordance with the above screen (STEP SA2). In this case, although the body weight may be input from the input section 51, it is also possible that data measured by a body weight measuring device (not shown) which is connected to the main unit 11 is automatically input and body weight specifying information (body weight) is calculated by the computation/control section 21. These input values are stored in the storage section 4.

Then, in STEP SA3, it is determined whether morphometric measured values such as trunk length and abdominal circumferential length are to be input. When these morphometric measured values are to be input, morphometry is carried out and measured values of the trunk length, abdominal circumferential length and the like are input from the input section 51 in STEP SA4, and the computation/control section 21 then proceeds to STEP SA6. When it is determined in STEP SA3 that the morphometric measured values are not input, the computation/control section 21 proceeds to STEP SA5. These input values are also stored in the storage section 4. Similarly, numerical value data and other data obtained in the following processes are also stored in the storage section 4.

In STEP SA5, the computation/control section 21 performs a morphometrical information estimation process (for example, using a calibration curve prepared from human body information database) for estimating trunk length, abdominal circumferential length or the like from the body specifying information such as the body height, body weight, gender and age stored in the storage section 4.

Then, in STEP SA6, the computation/control section 21 sends a frequency switching control signal to an applied frequency (constant current) source switching section 83 to set the frequency of the applied frequency constant current source for the current applying electrodes 13 at f1.

Then, in STEP SA7, a trunk impedance measurement process is performed in the body part impedance measuring section 3. This trunk impedance measurement process will be further described later with reference to the subroutine flowchart shown in FIG. 25. A trunk impedance Ztm and subcutaneous fat tissue layer impedance ZFS measured in this STEP SA7 are stored in the storage section 4 as Ztm(f1) and ZFS(f1), respectively.

Then, in STEP SA8, the computation/control section 21 sends a frequency switching control signal to the applied frequency (constant current) source switching section 83 to set the frequency of the applied frequency constant current source for the current applying electrodes 13 at f2. Then, in STEP SA9, a trunk impedance measurement process is performed in the body part impedance measuring section 3. This trunk impedance measurement process will be further described later with reference to the subroutine flowchart shown in FIG. 25. A trunk impedance Ztm and subcutaneous fat tissue layer impedance ZFS measured in this STEP SA9 are stored in the storage section 4 as Ztm(f2) and ZFS(f2), respectively.

Then, in STEP SA10, the computation/control section 21 performs a trunk skeletal muscle tissue layer impedance (ZMM) estimation process. In this estimation process, a trunk skeletal muscle tissue layer impedance ZMM is calculated based on the numerical values stored in the storage section 4 and the above expression 24.

Then, in STEP SA11, the computation/control section 21 performs a trunk skeletal muscle tissue cross-sectional area (AMM) estimation process. In this trunk skeletal muscle tissue cross-sectional area estimation process, a trunk skeletal muscle tissue volume MMtm is calculated based on the numerical values stored in the storage section 4 and the above expression 25. After this STEP SA11, the subcutaneous fat tissue layer impedance ZFS is stored in the storage section 4 as [ZFS(f1)+ZFS(f2)]/2.

Then, in STEP SA12, the computation/control section 21 performs a subcutaneous fat tissue volume (AFS) estimation process. A subcutaneous fat tissue volume can be calculated by the above expression 26.

Then, in STEP SA13, the computation/control section 21 performs a splanchnic organ tissue volume (AVM) and splanchnic organ tissue impedance (ZVM) estimation process. The process in this STEP SA13 can be considered to be completely the same as the process in STEP S10 described in the first embodiment with reference to FIG. 16.

Then, in STEP SA14, the computation/control section 21 performs a visceral fat tissue impedance (ZFV) and visceral fat tissue volume (AFV) estimation process. The process in this STEP SA14 can be considered to be completely the same as the process in STEP S11 described in the first embodiment with reference to FIG. 17.

Then, in STEP SA15, the computation/control section 21 computes a visceral fat/subcutaneous fat ratio (V/S). This computation is carried out in accordance with the above expression 27 stored in the storage section 4.

Then, in STEP SA16, the computation/control section 21 computes a body mass index (BMI). The body mass index can be calculated from the body weight W and body height H stored in the storage section 4 in accordance with the following expression.

$$BMI = W/H^2$$

Then, in STEP SA17, the computation/control section 21 computes a trunk body fat percentage (% Fatt). The trunk body fat percentage is calculated from the subcutaneous fat tissue volume (AFS), visceral fat tissue volume (AFV), trunk skeletal muscle tissue cross-sectional area (AMM) and splanchnic organ tissue volume (AVM) stored in the storage section 4 in accordance with the following expression.

$$\%\text{Fatt}=(AFS+AFV)/[(AFS+AFV)+AMM+AVM]\times 100$$

Then, in STEP SA18, the computation/control section 21 computes a visceral fat percentage (% VFat). The visceral fat percentage is calculated from the trunk body fat percentage (% Fatt) and visceral fat/subcutaneous fat ratio (V/S) calculated by the above computations and stored in the storage section 4 in accordance with the following expression.

$$\%V\text{Fat}=\% \text{Fatt}\times (V/S)/[(V/S)+1]$$

Finally, in STEP SA19, the computation/control section 21 displays, in the display section 52, the visceral fat tissue information (AFV, % VFat), body composition information (% Fatt, AMM, AFS, AVM) and body mass index (BMI) obtained by the above computations and advice guidelines obtained by processes to be described later. Thereby, a series of processes are ended (STEP SA20).

Next, the trunk impedance measurement process in STEP SA7 will be described in detail with reference to the subroutine flowchart of FIG. 25. In this first embodiment, "process of removing influence of change by breathing" and "process of determining abnormal value by drinking and eating and retention of water (e.g. urine) in bladder or the like" as described in (12) and (13) in the above 7. are conducted. Firstly, in STEP SA25, the computation/control section 21 initializes a counter and the like and the number of samples for measurement data of the impedance Ztm of the trunk, based on an instruction from the input section 51 or the like.

Then, in STEP SA26, the computation/control section 21 determines whether it is measurement timing. When it has been determined that it is measurement timing, the computation/control section 21 performs a trunk impedance (Ztm) measuring electrode placement setting process and a trunk impedance ($Ztm_x$) measurement process in STEP SA27. Further, in STEP SA28, the computation/control section 21 performs a subcutaneous fat tissue layer impedance (ZFS) measuring electrode placement setting process and a subcutaneous fat tissue layer impedance ($ZFS_x$) measurement process and then returns to STEP SA26.

Meanwhile, when it has been determined in STEP SA26 that it is not measurement timing, the computation/control section 21 proceeds to STEP SA29 and performs a measured impedance (Zx) data smoothing process (e.g. a moving average process), i.e. $Z_x=(Z_{x-1}+Z_x)/2$, on the trunk impedance ($Ztm_x$) and the subcutaneous fat tissue layer impedance ($ZFS_x$). Then, in STEP SA30, the computation/control section 21 performs a trunk impedance measured data breathing change correction process. This correction process will be further described later with reference to the subroutine chart of FIG. 18. Unlike the trunk impedance, the subcutaneous fat tissue layer impedance ($ZFS_x$) is not subjected to a correction process because it is hardly influenced by a change in breathing.

Then, in STEP SA31, the computation/control section 21 performs a time-series stability confirmation process of measured impedance of each body part. This is carried out by determining whether each value after the trunk impedance measured data breathing change correction process in STEP SA30 has converged to a value within a predetermined change in a predetermined number of times. This process is completely the same as that described in the first embodiment with reference to FIG. 19. In STEP SA32, the computation/control section 21 determines whether the measured Ztm, and $ZFS_x$ satisfy stable conditions. This determination is made such that a median breathing value is determined at the point when a median breathing value in each breathing cycle enters a stable range within a predetermined number of times. When it is determined in this STEP SA32 that the stable conditions are satisfied, the computation/control section 21 proceeds to STEP SA33 and registers the impedance value of the determined median value as the impedance value of the trunk or the impedance value of the subcutaneous fat tissues and a final stable condition determined value as a measurement result value in the storage section 4. Meanwhile, when it is determined in STEP SA32 that the stable conditions are not satisfied, the computation/control section 21 returns to STEP SA26 and repeats the above processes. Processes in subsequent STEPS SA33 to 35 are completely the same as the processes in STEPS S30 to 32 described in the first embodiment with reference to FIG. 18. Therefore, descriptions thereof will be omitted.

Figure 26:
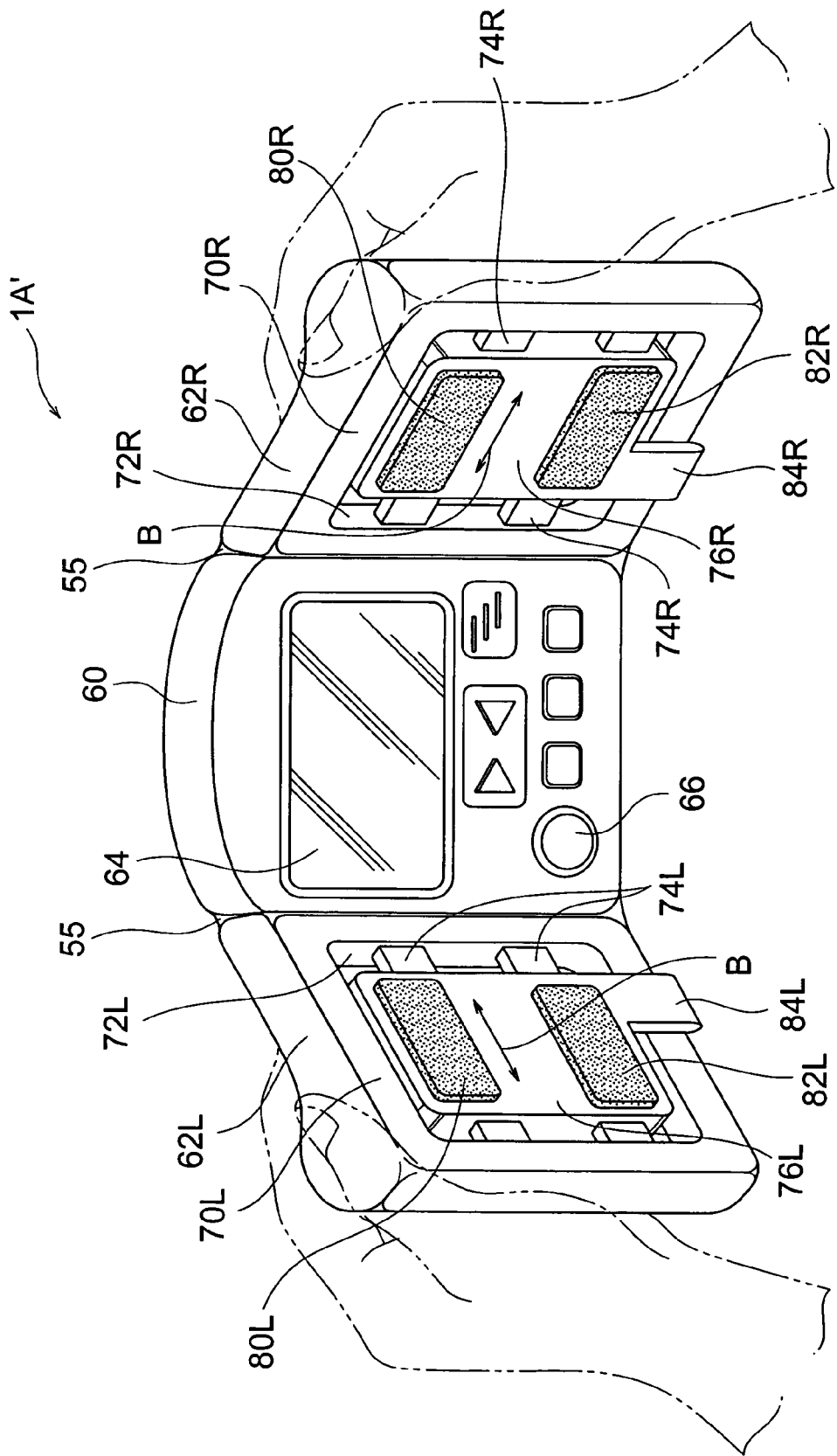
FIG. 26 is an external perspective view of a measuring apparatus according to the second embodiment of the present invention.

FIG. 26 is an external perspective view of a variation of the measuring apparatus according to the second embodiment of the present invention. An apparatus 1A' in this variation corresponds to the apparatus 1' in the first embodiment described with reference to FIG. 21. Primary differences between the apparatus 1A' and the apparatus 1' are that voltage measuring electrodes 80R and 80L and current applying electrodes 82R and 82L are provided in the upper and lower portions of the top surfaces of the slide supports 76R and 76L, respectively, and that positioning guide sections 84R and 84L are provided to increase the accuracy of positioning of the electrodes. Otherwise, the apparatus 1A' is the same as the apparatus 1'.

The positioning guide sections 84R and 84L are formed by, for example, extending portions of the slide supports 76R and 76L downward. In actual use, the apparatus 1A' is disposed around the navel A of a subject 71. At that time, the slide supports 76R and 76L are slid in the transverse direction (abdominal circumferential direction), so that the guide sections 84R and 84L are disposed in contact with a body part, such as anterior superior iliac spine of the subject 71 such that they bookend the pelvic crest (anterior superior iliac spine) of the iliac bone of the subject from their inner sides.

Figure 27:
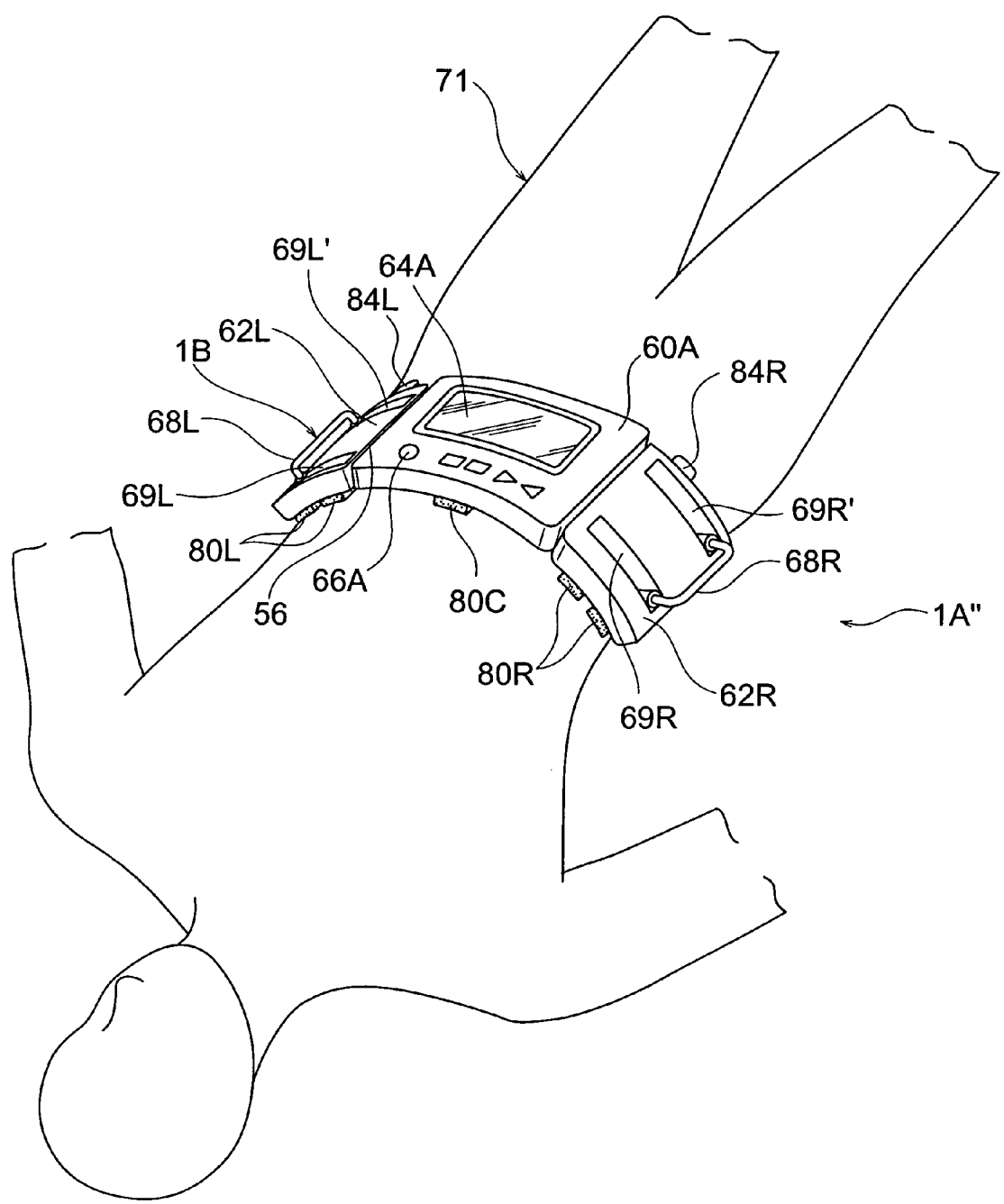
FIG. 27 is a diagram illustrating a variation of positioning guide sections according to the second embodiment of the present invention.

FIG. 27 shows another variation of the measuring apparatus according to the second embodiment. An apparatus 1A" shown in this variation has a liquid crystal display section 64A and various switches 66A on the surface opposite to the abdomen-contacting surface so that a user can view the liquid crystal display section and operate the switches during measurement. As is obvious, the constitution shown in FIG. 26 is suited for a case where a subject makes a measurement by himself, while the constitution shown in FIG. 27 is suited for a case where the subject 71 in a recumbent posture is measured by someone other than the subject. Further, according to the constitution of FIG. 27, it is possible to provide a central electrode 80C on (the abdomen-contacting side of) a main unit 60A. In the example of FIG. 27, the ends of grippers 68R and 68L are connected to slide supports (not shown) on which the electrodes 80R and 80L are mounted through holes 69R, 69R', 69L and 69L', so as to make the electrodes movable. A subject can slide the slide supports connected to the ends of the grippers 68R and 68L and the electrodes 80R and 80L provided on the slide supports to appropriate positions according to the size of the body of the subject by moving the grippers 68R and 68L in the extending direction of the holes 69 and 69'. The voltage measuring electrodes 80 and the current applying electrodes 82 may be implemented by metal-plating the surfaces of an SUS material and a resin material, as in the foregoing embodiments.

Although an example using two frequencies has been illustrated in the above embodiment, an improvement in the reliability and accuracy of measured values can be expected by using information measured by two or more frequencies and the frequency characteristic measurement accuracy of the skeletal muscle tissue layer for confirmation.

Further, it is possible to use the above f1 (frequency around 50 kHz) for estimation of skeletal muscle amount tissue volume having high sensitivity to rectus abdominis muscle out of abdominal muscles which are anti gravitational muscles in the skeletal muscle tissue layer and the above f2 (frequency of 150 kHz or higher) for estimation of skeletal muscle tissue volume. That is, for an impedance measured value by f1, since rectus abdominis muscle which is important as a development indicator for anti gravitational muscles can be acquired with high sensitivity, application thereof as useful information when development of the anti gravitational muscles is deformed is conceivable. The reason that the rectus abdominis muscle can be acquired with high sensitivity is that while other muscle tissues constituting the abdomen of the trunk have diagonal muscle fiber directions, the rectus abdominis muscles are arranged horizontally in the trunk longitudinal direction, so that higher volume-resistivity than those of other skeletal muscle tissue layers is measured upon energization from the surface of the abdomen of the trunk.

Further, according to the present invention, a visceral fat tissue volume, a skeletal muscle tissue volume and a subcutaneous fat tissue volume can deal with both results of a case of a cross-sectional area at the navel and a case where they are treated as volumes by providing a trunk abdominal section length.

Third Embodiment

Next, an example of a trunk subcutaneous fat measuring method and apparatus and trunk visceral/subcutaneous fat measuring method and apparatus according to a third embodiment of the present invention will be described based on the above measurement principle of the present invention. In the following description and drawings, for the same members as those in the first embodiment, the same numbers are used.

Figure 28:
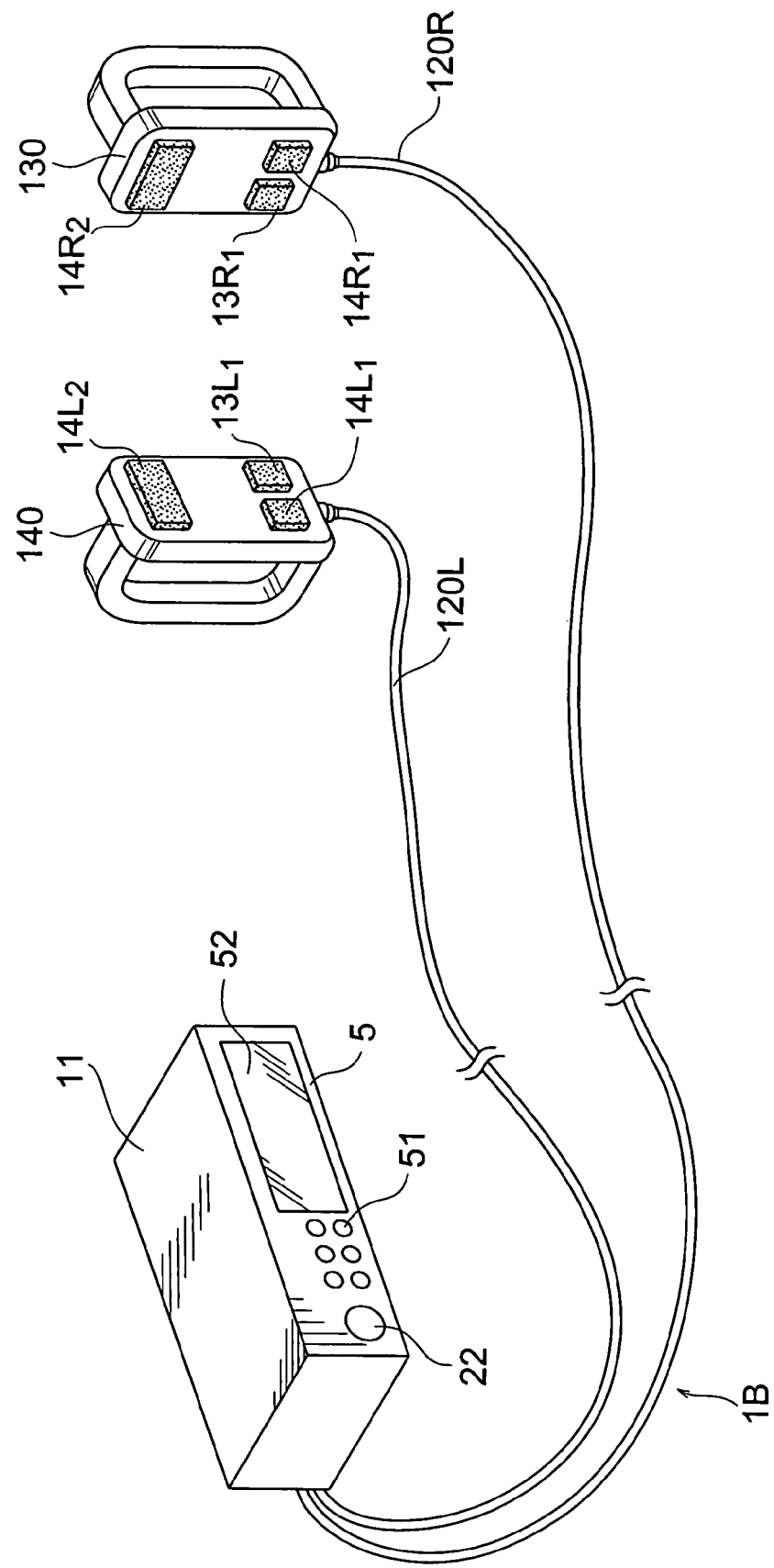
FIG. 28 is a schematic perspective view of the appearance of an example of a trunk visceral/subcutaneous fat measuring apparatus according to a third embodiment of the present invention.
Figure 29:
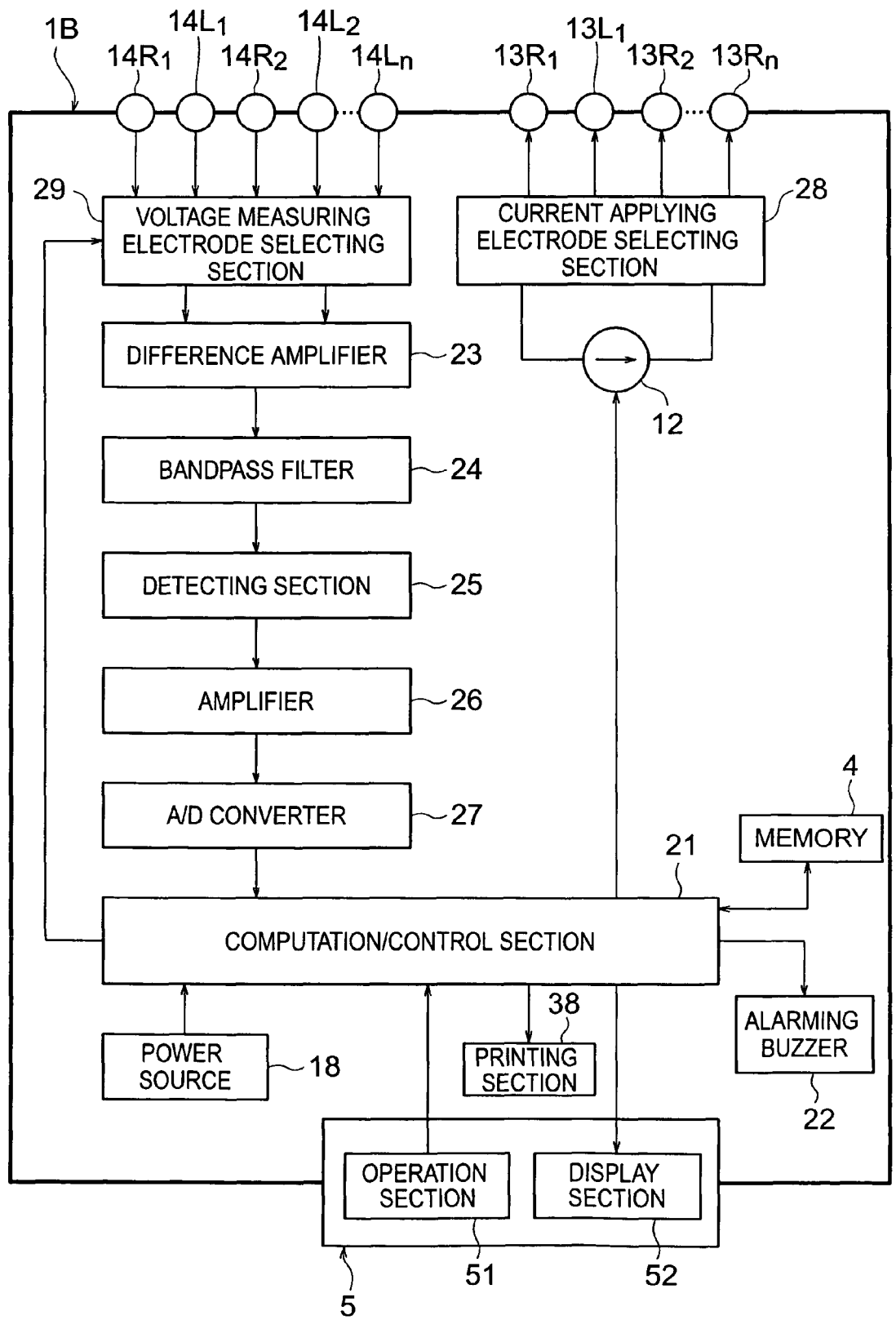
FIG. 29 is a block diagram illustrating the main unit of the trunk visceral/subcutaneous fat measuring apparatus according to the third embodiment of the present invention.

FIG. 28 is a diagram corresponding to FIG. 1 and is a schematic perspective view of the appearance of an example of a trunk visceral/subcutaneous fat measuring apparatus (trunk subcutaneous fat measuring apparatus) 1B according to the third embodiment of the present invention. FIG. 29 is a diagram corresponding to FIG. 3 and is a block diagram showing a main unit included in the trunk visceral/subcutaneous fat measuring apparatus (trunk subcutaneous fat measuring apparatus) 1B according to the third embodiment.

As is obvious from FIG. 28, a primary difference in appearance between the apparatus 1 and the apparatus 1B is that the apparatus 1B has current applying electrodes $13R_1$ and $13L_1$ and voltage measuring electrodes $14R_1$ and $14L_1$ in the lower portions of the contact surfaces of grip electrode sections 130 and 140 and voltage measuring electrodes $14R_2$ and $14L_2$ in the upper portions of the contact surfaces thereof. Further, as is obvious from FIG. 29, a primary difference in constitution between the apparatus 1 and the apparatus 1B is that the apparatus 1B comprises a current applying electrode selecting section 28 having a plurality of current applying electrodes and a voltage measuring electrode selecting section 29 having a plurality of voltage measuring electrodes.

A computation/control section 21 performs various inputs and outputs, measurements, computations and the like, such as computations of trunk skeletal muscle tissue cross-sectional area, trunk skeletal muscle tissue layer impedance, visceral fat tissue impedance, visceral fat tissue volume, splanchnic organ tissue volume, splanchnic organ tissue impedance, subcutaneous fat tissue volume, subcutaneous fat tissue layer impedance (the above measured impedance may be used), trunk visceral fat/subcutaneous fat ratio and the like based on body weight specifying information (such as a body weight) input from an operation section (input section) 51, measured impedances and the expressions 1 to 15, a process of removing the influence of change by breathing, a process of determining abnormality in splanchnic tissues, and the like.

A storage section 4 stores not only body specifying information such as a body height and a trunk length and the above expressions 1 to 15 but also appropriate messages for health guideline advice.

An impedance measuring section comprises a plurality of current applying electrodes 13 ($13R_1$, $13L_1$ ... $13R_n$, $13L_n$) for applying a current to a body part to be measured of a subject, a plurality of voltage measuring electrodes 14 ($14R_1$, $14L_1$ ... $14R_n$, $14L_n$) for measuring a potential difference in a body part to be measured of a subject, a current source 12 for supplying a current to the current applying electrodes 13, the voltage measuring electrode selecting section 29 for selecting a predetermined voltage measuring electrode 14 according to an application, the current applying electrode selecting section 28 for selecting a predetermined current applying electrode 13 according to an application, a difference amplifier 23 for amplifying a measured potential difference, a bandpass filter 24 for filtering, a detecting section 25, an amplifier 26, and an A/D converter 27. The numbers of the current applying electrodes $13R_1$, $13L_1$ ... $13R_n$, $13L_n$ and the voltage measuring electrodes $14R_1$, $14L_1$ ... $14R_n$, $14L_n$ are determined according to an application and are not particularly limited.

The current applying electrodes 13 ($13R_1$, $13L_1$ ... $13R_n$, $13L_n$) and the voltage measuring electrodes 14 ($14R_1$, $14L_1$ ... $14R_n$, $14L_n$) may be implemented by metal-plating the surfaces of an SUS material and a resin material, as in the case of the current applying electrodes 13R and 13L and the voltage measuring electrodes 14R and 14L in the first embodiment.

Since the principle of the present invention is nearly the same as that described in the first embodiment with reference to FIGS. 4 to 10, only differences therebetween will be described hereinafter.

Figure 30:
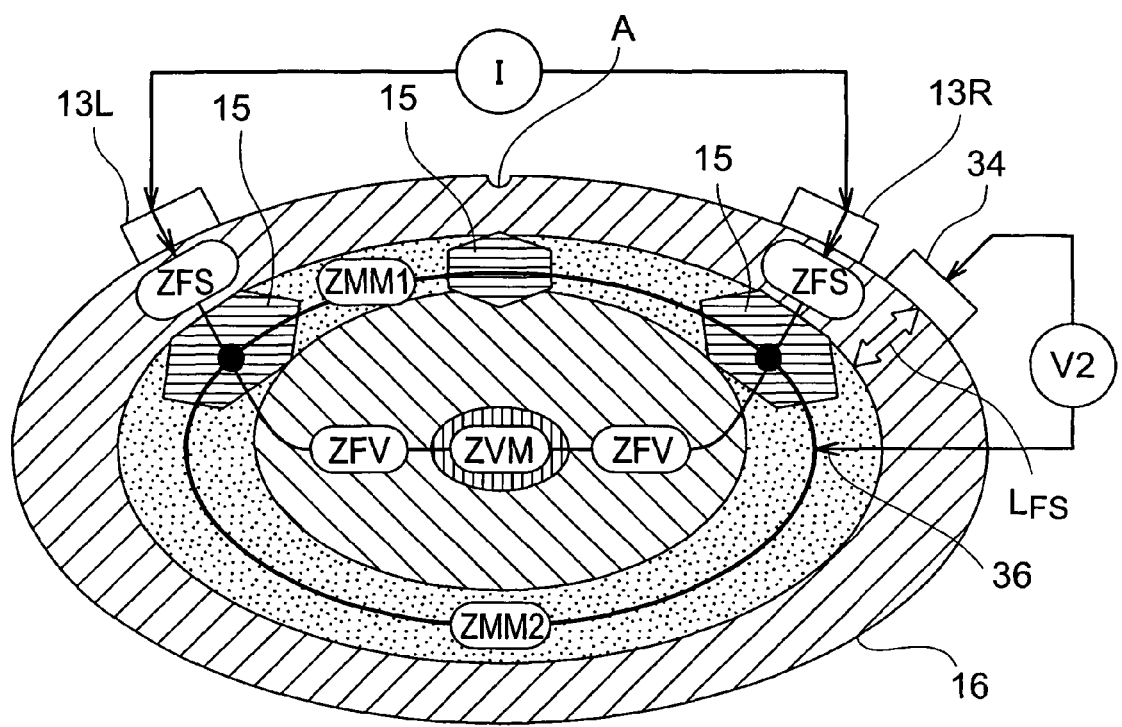
FIG. 30 is a schematic diagram illustrating an example of an electrode arrangement according to the third embodiment of the present invention with the structure of the abdomen of the trunk.

FIG. 30 shows an example of the electrode disposition method according to the present invention for acquiring subcutaneous fat tissue layer information, in the same manner as in FIG. 4 in the first embodiment. As will be described later, the present invention measures subcutaneous fat tissue layer information and visceral fat tissue information simultaneously as independent informations based on the electrode disposition method. The apparatus of the present invention has voltage measuring electrodes for measuring visceral fat tissues and voltage measuring electrodes for measuring a subcutaneous fat tissue layer and measures visceral fat tissue information and subcutaneous fat tissue layer information by switching an arrangement of these electrodes selectively by switching means. An object of measuring the informations simultaneously is to make it possible to relatively remove change error factors during measurement caused by breathing or the like by making both measurements in the same environment simultaneously, e.g. measuring the error factors at sampling timing faster than a change in breathing. Thus, the influences of heartbeat and other body motions other than breathing are also conceivable. The same object can be achieved by a smoothing process in the same measurement environment, in addition to the increase in speed.

Figure 31:
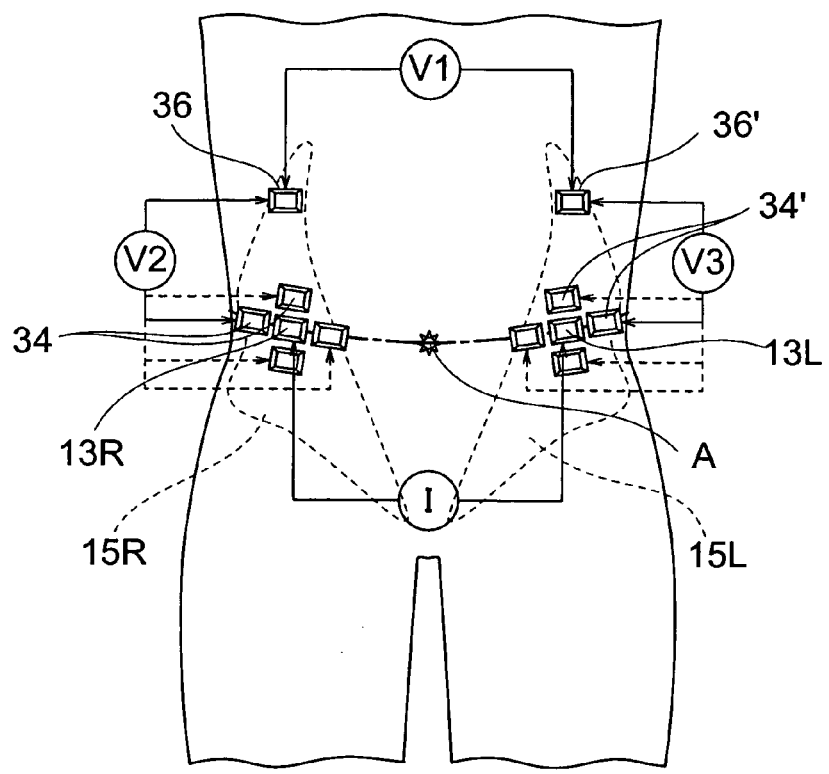
FIG. 31 is a diagram illustrating an electrode arrangement example for measuring information only about a subcutaneous fat tissue layer.
Figure 32:
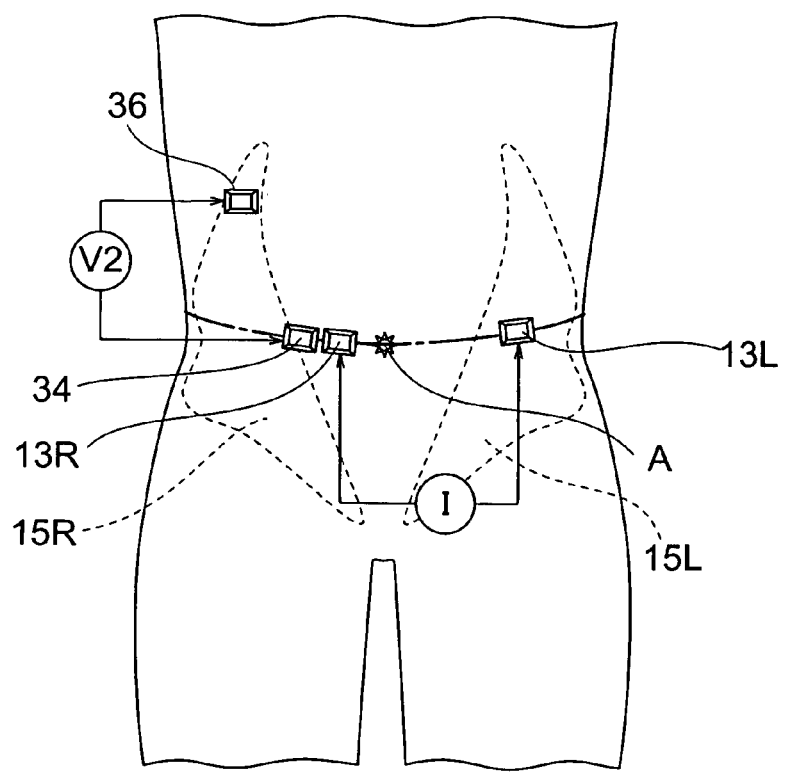
FIG. 32 is a diagram illustrating an electrode arrangement example for measuring information only about the subcutaneous fat tissue layer.
Figure 33:
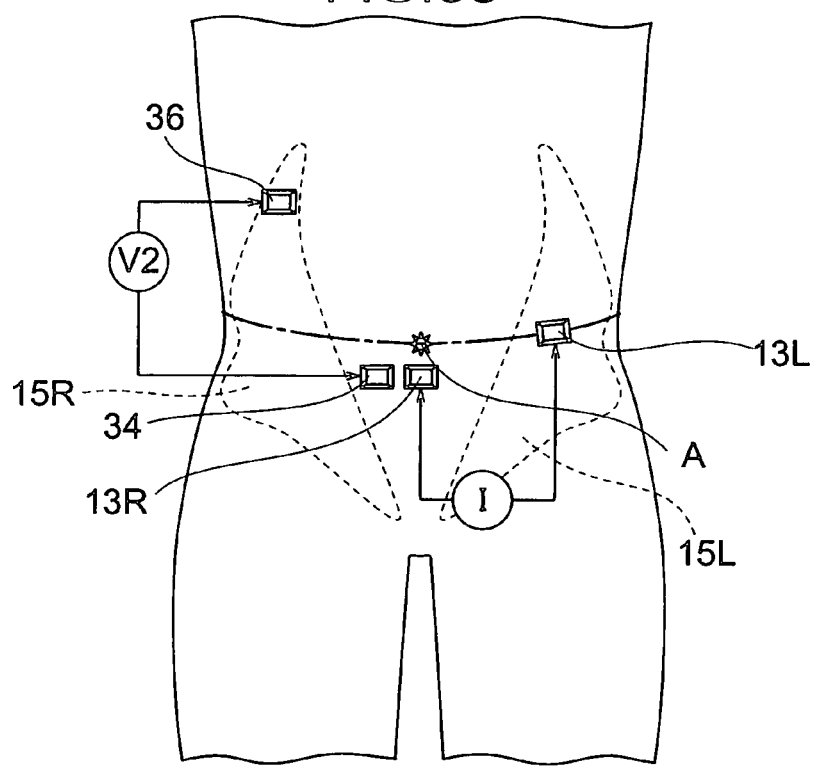
FIG. 33 is a diagram illustrating an electrode arrangement example for measuring information only about the subcutaneous fat tissue layer.
Figure 34:
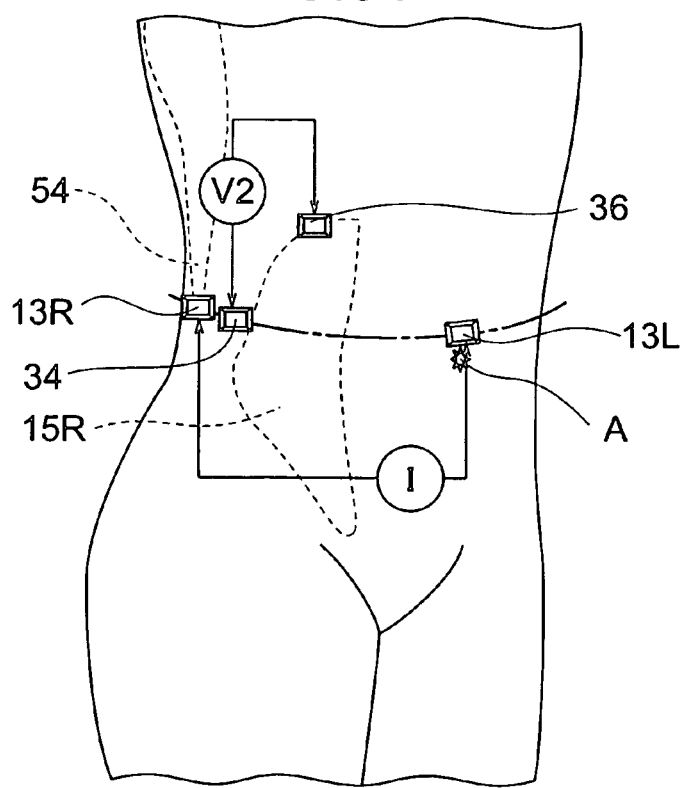
FIG. 34 is a diagram illustrating an electrode arrangement example for measuring information only about the subcutaneous fat tissue layer.

FIGS. 31 to 34 show specific examples of electrode arrangements for acquiring subcutaneous fat tissue layer information (not visceral fat tissue information). FIG. 31 is a diagram illustrating an electrode arrangement example of measuring the impedance of the subcutaneous fat tissue layer right underneath current applying electrodes 13L and 13R disposed in the left and right aponeurosis sections 15, wherein V2 indicates a right-front-side subcutaneous fat tissue measured potential and V3 indicates a left-front-side subcutaneous fat tissue measured potential. FIG. 32 is a diagram illustrating an electrode arrangement example of measuring the impedance of the subcutaneous fat tissue layer right underneath the current applying electrode 13R disposed in the vicinity of the navel, wherein V2 indicates an around-navel subcutaneous fat tissue measured potential. FIG. 33 is a diagram illustrating an electrode arrangement example of measuring the impedance of the subcutaneous fat tissue layer right underneath the current applying electrode 13R disposed under the navel, wherein V2 indicates an under-navel subcutaneous fat tissue measured potential. FIG. 34 is a diagram illustrating an electrode arrangement example of measuring the impedance of the subcutaneous fat tissue layer right underneath the current applying electrode 13R disposed in a lateral region 54, wherein V2 indicates the subcutaneous fat tissue measured potential of the lateral region 54.

To acquire subcutaneous fat tissue layer information (more specifically, a potential difference value or an impedance value), spreading resistance is used in this case. The spreading resistance has been generally considered unfavorable. However, since it can be said that spreading resistance right underneath the current applying electrode in particular represents information about the subcutaneous fat tissue layer, useful subcutaneous fat information can be acquired by measuring a potential difference in this region. The present invention acquires subcutaneous fat tissue layer information by focusing on this point.

To measure spreading resistance, at least one pair of current applying electrodes and at least one pair of voltage measuring electrodes capable of measuring a potential difference which occurs in a subject by a current applied from the current applying electrodes are provided. One of the current applying electrodes, for example, a current applying electrode, is used to apply a current to a body part where the subcutaneous fat tissue layer is thin or a body part having no or a little abdominal muscle portion of the skeletal muscle tissue layer, and the other current applying electrode, such as the current applying electrode 13L, is used to apply a current to a body part where the subcutaneous fat tissue layer is thick (or a subcutaneous fat tissue layer measured body part).

Meanwhile, voltage measuring electrodes 34 included in the voltage measuring electrode pairs are disposed at a site where the influence of spreading resistance right underneath the current applying electrode is dominant, i.e., in the vicinity of the current applying electrodes. Meanwhile, the other voltage measuring electrodes 36 are disposed at a remote site where the influence of the spreading resistance right underneath the current applying electrode is weak (site remote from the current applying electrodes by at least three times the distance between the current applying electrode and the voltage measuring electrodes 34), i.e., at a body part where the electrodes are not or hardly influenced by the subcutaneous fat tissue layer right underneath the current applying electrode. The former voltage measuring electrodes 34 may be disposed at a body part where fat is accumulated very thickly to the extent that the subcutaneous fat tissue layer reflects individual differences, such as around the navel, a lateral abdominal region (upper border of the iliac crest) or a lateral back region, and the latter voltage measuring electrodes 36 may be disposed at a body part where fat is hardly accumulated to the extent that the subcutaneous fat tissue layer reflects individual differences, e.g. between the navel and the upper border of the iliac crest (near the aponeurosis between the external abdominal oblique muscle and the rectus abdominis muscle). The same information can be acquired regardless of where around the current applying electrode the voltage measuring electrodes are disposed. For instance, as shown in FIG. 31, the subcutaneous fat tissue layers on the left and right sides can be measured by disposing the voltage measuring electrodes in the vicinity of the left and right current applying electrodes which oppose each other with the navel and the backbone as the central axis.

The measurement values of potential differences V2 and V3 which occur between the voltage measuring electrodes 34 and 36 by a current applied from the current applying electrodes are considered impedance information which is proportional to the impedance (ZFS) value of the subcutaneous fat tissue layer and to the thickness ($L_{FS}$) information of the subcutaneous fat tissue layer. When the impedance of the spreading resistance is represented by $\Delta Z$ and a constant corresponding to the area of the current applying electrode is represented by A0, the following expression holds.

$$\Delta Z \times \propto ZFS \propto L_{FS}/A0 \propto L_{FS}$$

Thus, the cross-sectional area AFS of the subcutaneous fat tissue layer can be determined by the following expression.

$$AFS = Lw \times L_{FS} = aa0 \times ZFS \times Lw + bb0 \qquad \text{expression 26}$$

In the above expression, Lw represents abdominal circumferential length, i.e. the length of the circumference of the abdomen 16, and aa0 and bb0 are constants showing different values for a male and a female.

To acquire visceral fat tissue information (e.g. a voltage value or an impedance value) together with the subcutaneous fat tissue layer information, at least one more pair of voltage measuring electrodes which are disposed in a different arrangement from the voltage electrode arrangement for measuring the subcutaneous fat tissue layer information (Thus, it is understood that at least two pairs of voltage measuring electrodes are required to implement the present method and apparatus capable of measuring subcutaneous fat tissue information and visceral fat tissue information simultaneously.)

Figure 35:
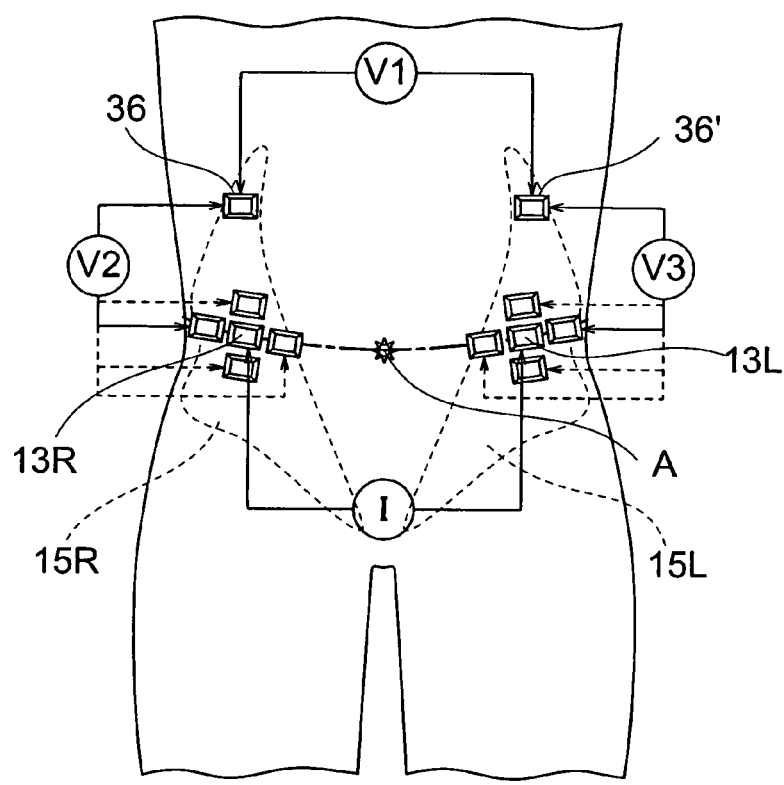
FIG. 35 is a diagram illustrating an electrode arrangement example for measuring subcutaneous fat tissue layer information and visceral fat tissue information simultaneously as independent informations.
Figure 36:
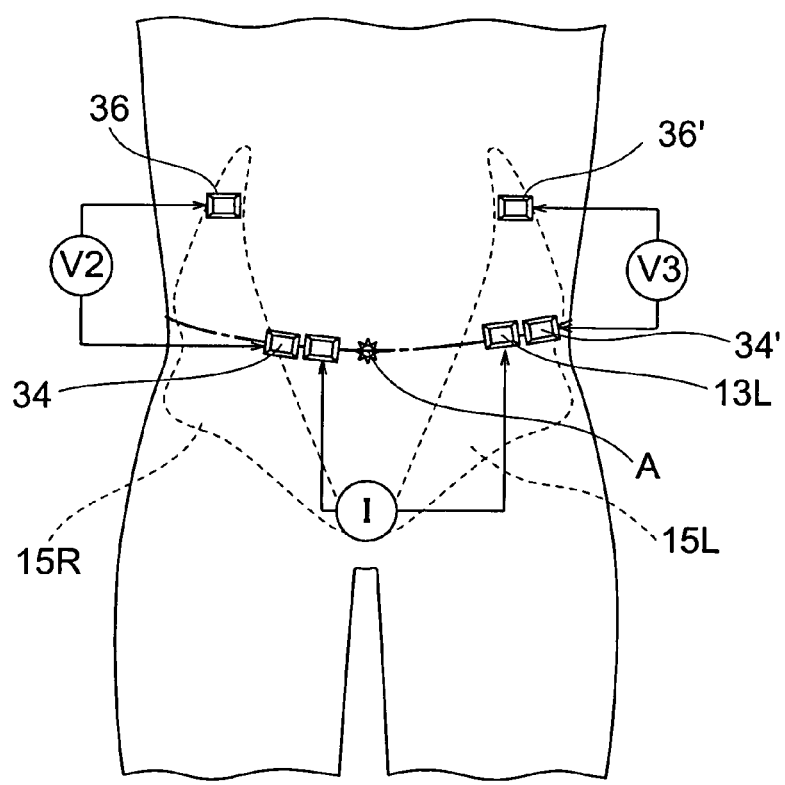
FIG. 36 is a diagram illustrating an electrode arrangement example for measuring subcutaneous fat tissue layer information and visceral fat tissue information simultaneously as independent informations.
Figure 37:
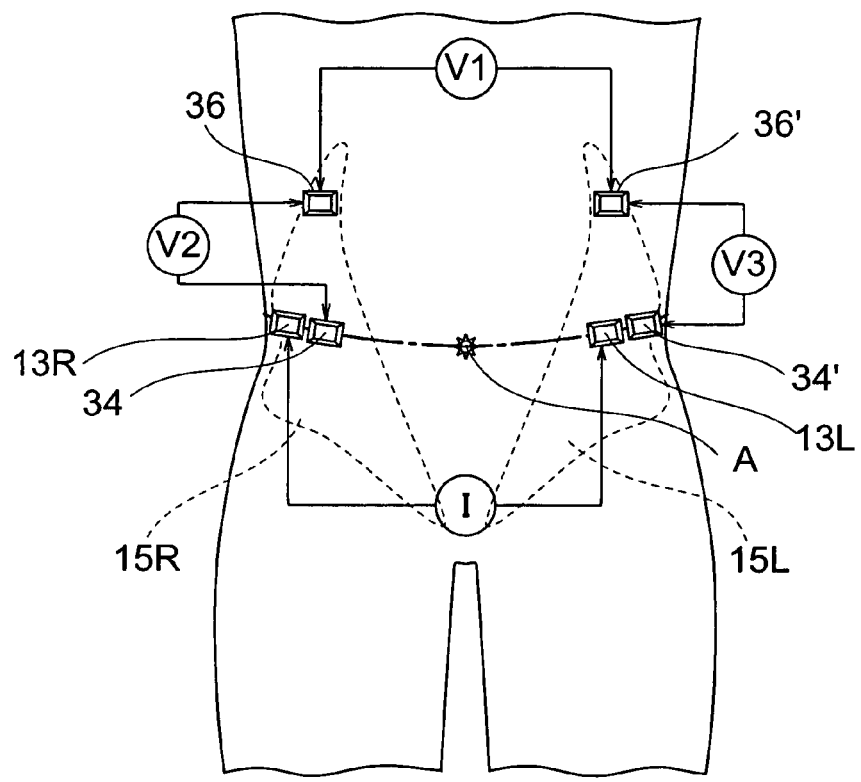
FIG. 37 is a diagram illustrating an electrode arrangement example for measuring subcutaneous fat tissue layer information and visceral fat tissue information simultaneously as independent informations.
Figure 38:
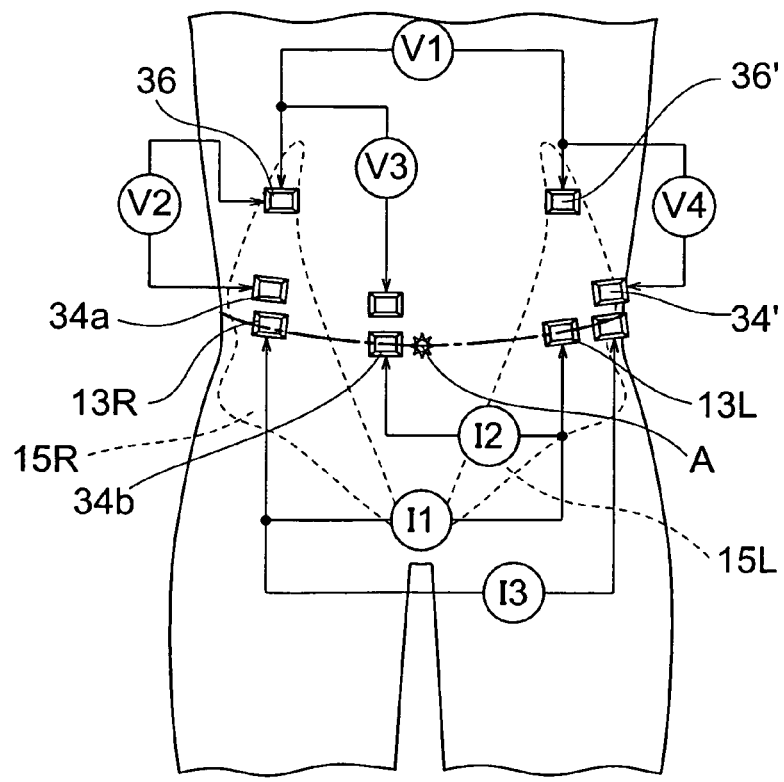
FIG. 38 is a diagram illustrating an electrode arrangement example for measuring subcutaneous fat tissue layer information and visceral fat tissue information simultaneously as independent informations.

FIGS. 35 to 38 show specific examples of electrode arrangements for measuring subcutaneous fat tissue layer information and visceral fat tissue information simultaneously. FIG. 35 is a diagram illustrating an electrode arrangement example of measuring visceral fat tissues and the impedance of the subcutaneous fat tissue layer right underneath current applying electrodes 13R and 13L disposed in the left and right aponeurosis sections 15R and 15L, wherein V1 indicates a visceral fat tissue measured potential, V2 indicates a right-front-side subcutaneous fat tissue measured potential and V3 indicates a left-front-side subcutaneous fat tissue layer measured potential. Since the tissue layer balance between the left and right sides of a living body are considered to be nearly symmetrical, V2≈V3 holds, and the same measurement results are obtained by using any of voltage measuring electrodes disposed in four directions in the vicinity of the current applying electrodes. FIG. 36 is a diagram illustrating an electrode arrangement example of measuring visceral fat tissues and the impedance of the subcutaneous fat tissue layer right underneath the current applying electrodes disposed in the vicinity of the navel A and the left aponeurosis section 15L, wherein V1 indicates a visceral fat tissue measured potential and V2 indicates an around-navel subcutaneous fat tissue layer measured potential. FIG. 37 is a diagram illustrating an electrode arrangement example of measuring visceral fat tissues and the impedance of the subcutaneous fat tissue layer right underneath the current applying electrodes 13L and 13R disposed in the right and left aponeurosis sections 15L and 15R, wherein V1 indicates a visceral fat tissue measured potential, V2 indicates a right-abdominal-side subcutaneous fat tissue layer measured potential and V3 indicates a left-front-side subcutaneous fat tissue layer measured potential. FIG. 38 is a diagram illustrating an electrode arrangement example of measuring visceral fat tissues and the impedance of the subcutaneous fat tissue layer right underneath the current applying electrodes disposed at multiple sites, wherein V1 in combination with I1 indicates a visceral fat tissue measured potential, V2 in combination with I1 indicates a right-front-side subcutaneous fat tissue layer measured potential, V3 in combination with I2 indicates an around-navel subcutaneous fat tissue layer measured potential, and V4 in combination with I3 indicates a left-abdominal-side subcutaneous fat tissue layer measured potential.

Measurement of the visceral fat tissues is not direct measurement of the visceral fat tissues. The model of FIG. 5 or FIG. 6 used in describing the first embodiment is assumed, and a complex of the splanchnic organ tissues and the visceral fat tissues is measured. In the measurement of the visceral fat tissues, to secure an optimum S/N condition, the amounts of currents passing from the current applying electrodes through the splanchnic organ tissues and visceral fat tissues under the skeletal muscle tissue layer are increased to secure the measurement sensitivity for the tissues to be measured. Further, a current is applied from a body part where the subcutaneous fat tissue layer is thin or a body part where the skeletal muscle tissue layer has no or a thin muscle belly portion by the current applying electrodes to minimize the influence of spreading resistance and improve the sensitivity of energization through the splanchnic organ tissues and the visceral fat tissues. Further, when an abdominal circumferential cross-sectional area is a measurement reference, a body part to which a current is applied from the current applying electrodes 13L and 13R is a body part where the subcutaneous fat tissue layer is deposited the most thinly or a skeletal muscle joining tissue area with good electrical conductivity where the skeletal muscle tissue layer has no or a thin muscle belly portion. An example thereof is a tendinous portion (such as tendinous intersection or aponeurosis) 15. More specifically, the body part is a section between the navel and the upper border of the iliac crest or a tendinous portion (aponeurosis) between the rectus abdominis muscle and the external abdominal oblique muscle.

To acquire visceral fat tissue information as well as subcutaneous fat tissue layer information, additional voltage measuring electrode pairs, i.e. V1 in FIGS. 35 to 37 and V1 and V3 in FIG. 38, are provided in the examples of FIGS. 35 to 38. These additional voltage measuring electrode pairs are disposed at a site with good electrical conductivity where the subcutaneous fat tissue layer is thin or where the skeletal muscle tissue layer has no or a thin muscle belly portion. As is obvious from the drawings, the voltage measuring electrodes 36 and 36' included in the voltage measuring electrode pairs for acquiring subcutaneous fat tissue layer information can also be used as voltage measuring electrodes included in these additional voltage measuring electrode pairs for acquiring visceral fat tissue information. For example, in FIG. 35, the voltage measuring electrodes 36 and 36' included in the voltage measuring electrode pair V1 for acquiring visceral fat tissue information can also be used as voltage measuring electrodes included in the voltage measuring electrode pair V2 for acquiring subcutaneous fat tissue layer information or voltage measuring electrodes included in the voltage measuring electrode pair V3 for acquiring subcutaneous fat tissue layer information.

Thus, in the constitutions of FIGS. 35 to 38, at least two voltage measuring electrode pairs, i.e. the voltage measuring electrode pair for measuring the subcutaneous fat tissue layer and the voltage measuring electrode pair for measuring visceral fat tissues are provided. A potential difference to be measured (any of V1 to V3), in other words, a body part be measured, can be selected easily by the voltage measuring electrode selecting section 29 shown in FIG. 29. Therefore, according to the present invention, visceral fat tissue information and subcutaneous fat tissue layer information can be easily measured separately by switching the electrode arrangement configuration having both an arrangement for measuring visceral fat tissues and an arrangement for measuring the subcutaneous fat tissue layer by the switching means.

As is obvious from the above description, in the present invention, the best distance condition is secured by adopting the electrode arrangement off the navel circumference, and the impedance (ZFS) of the subcutaneous fat tissue layer is separated and removed as proper measurement of the four-electrode technique. Further, in the present invention, not all of the four electrodes are disposed on the abdominal circumference, but at least one of them is disposed off the abdominal circumference so as to secure a more optimum S/N condition. As such a disposition method, for example, it is conceivable to dispose the current applying electrodes on the navel (abdominal) circumference and dispose one or both of the voltage measuring electrodes off the navel (abdominal) circumference. Further, it is also possible to dispose one of the current applying electrodes on the navel (abdominal) circumference and dispose the other current applying electrode off the navel (abdominal) circumference. Further, the current applying electrodes or the voltage measuring electrodes may be disposed in the above sections, i.e. body parts where the subcutaneous fat tissue layer is thin, on the left and right sides when viewed with the navel of a subject as the center therebetween. However, the voltage measuring electrodes are disposed in the trunk longitudinal direction within an abdominal region off the navel (abdominal) circumference.

The operations of the trunk visceral/subcutaneous fat measuring apparatus (trunk subcutaneous fat measuring apparatus) in the third embodiment are completely the same as those shown in FIGS. 14, 16, 17, 19 and 20 of the first embodiment and FIG. 25 of the second embodiment used in place of FIG. 18 of the first embodiment. Further, even in this third embodiment, the variation shown in FIG. 21 of the first embodiment can be used.

Fourth Embodiment

Next, an example of a trunk visceral fat measuring method and apparatus and health guideline advising apparatus using measured data according to a fourth embodiment of the present invention will be described based on the above described measurement principle of the present invention. In the following description and drawings, the same members as those in the first embodiment are given the same numbers.

Figure 39:
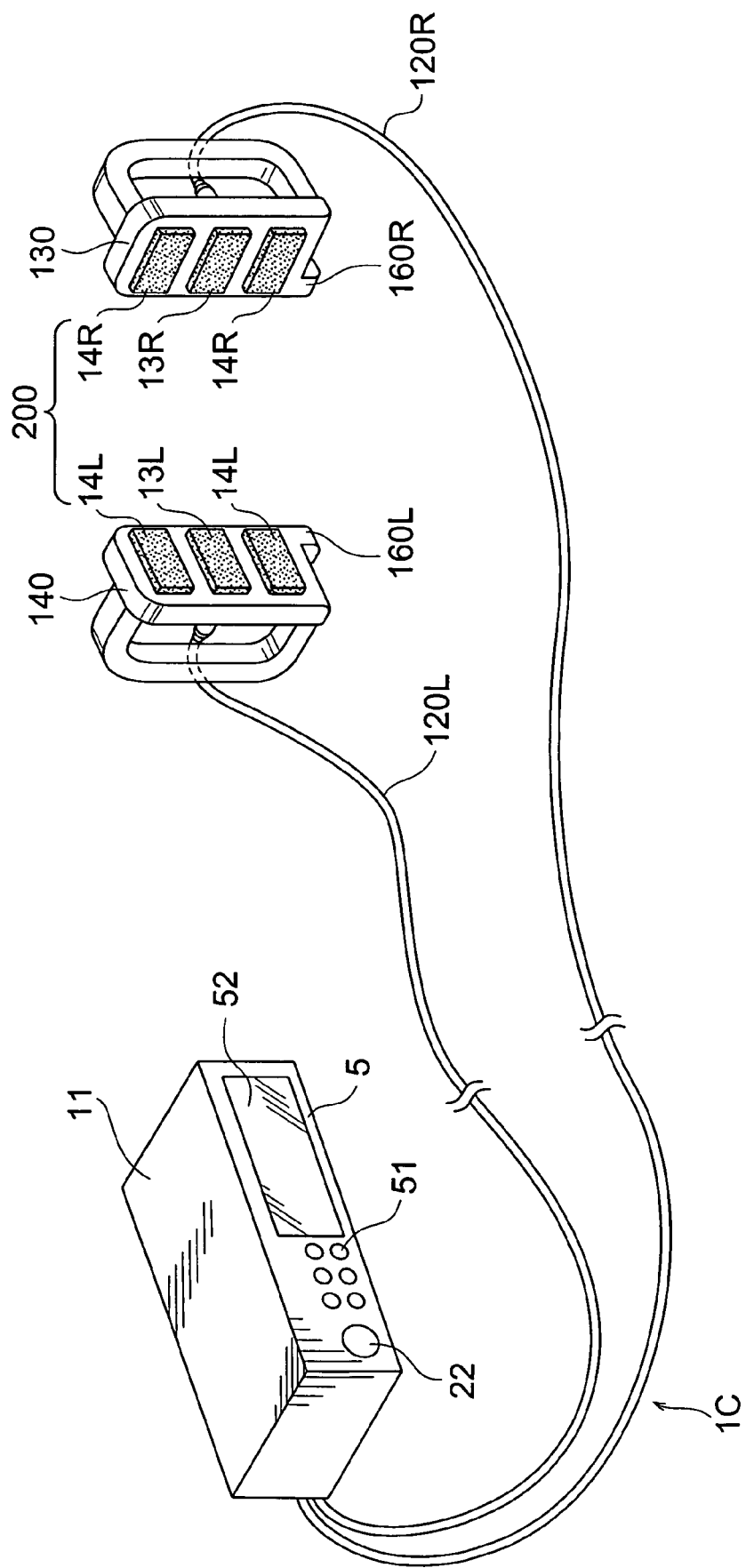
FIG. 39 is a schematic perspective view of the appearance of an example of a trunk visceral fat measuring apparatus according to a fourth embodiment of the present invention.
Figure 40:
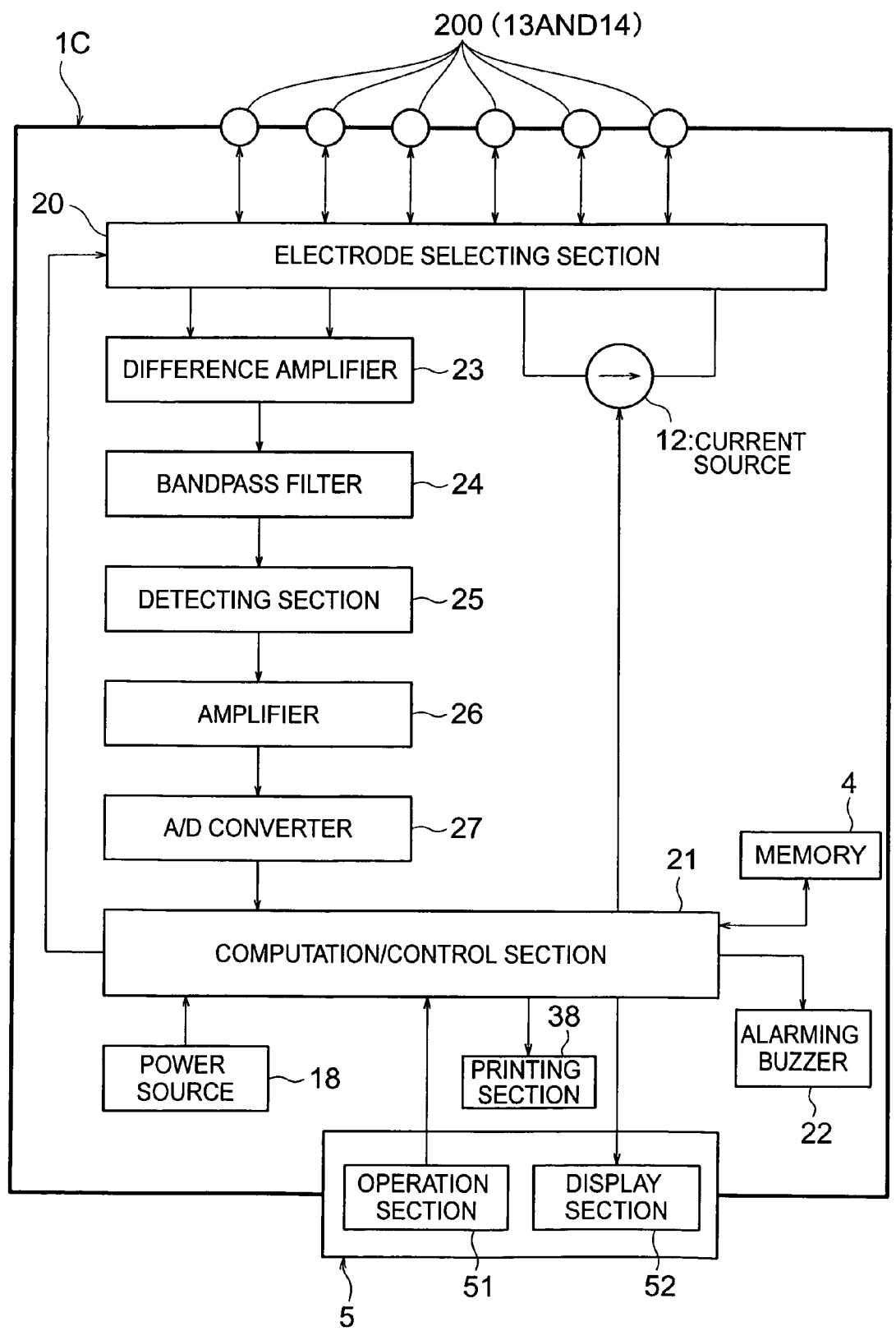
FIG. 40 is a block diagram illustrating the main unit of the trunk visceral fat measuring apparatus according to the fourth embodiment of the present invention.

FIG. 39 is a diagram corresponding to FIG. 1 and is a schematic perspective view of the appearance of an example of a trunk visceral fat measuring apparatus 1C according to the fourth embodiment of the present invention. FIG. 40 is a diagram corresponding to FIG. 3 and is a block diagram showing a main unit included in the trunk visceral fat measuring apparatus 1C according to the fourth embodiment.

As is obvious from FIG. 39, a primary difference in appearance between the apparatus 1 and the apparatus 1C is that the apparatus 1C has electrodes 200 (current applying electrodes 13R and 13L and voltage measuring electrodes 14R and 14L) on the contact surfaces of grip electrode sections 130 and 140 and that the apparatus 1C has guides 160R and 160L. Further, as is obvious from FIG. 40, a primary difference in constitution between the apparatus 1 and the apparatus 1C is that the apparatus 1C uses the electrodes 200.

In the apparatus 1C, the electrodes can be pressed against the same positions all the time by placing the guides 160R and 160L on the pelvis (anterior superior iliac spine). Although the number of the electrodes 200 shown in FIGS. 39 and 40 is 6, it may be increased to 8 according to the following measurement as shown in FIG. 16 or even more electrodes may be used as required.

In addition to the handy type shown in FIG. 2, the trunk visceral fat measuring apparatus 1C may be a belt type. This belt type comprises a small main unit and left and right grip electrode sections connected to both sides of the main unit bendably and stretchably by a rubber material or a resin material, thereby constituting a belt form as a whole, and is pressed against the abdomen upon use.

A computation/control section 21 performs various inputs and outputs, measurements, computations and the like, such as computations of trunk skeletal muscle tissue cross-sectional area, trunk skeletal muscle tissue layer impedance, visceral fat tissue impedance, visceral fat tissue volume, splanchnic organ tissue volume, splanchnic organ tissue impedance, subcutaneous fat tissue volume, trunk visceral fat/subcutaneous fat ratio and the like based on body weight specifying information (such as a body weight) input from an operation section 51, measured impedances and the above expressions 1 to 15, a process of removing the influence of change by breathing, a process of determining abnormality in splanchnic organ tissues, and the like.

A storage section 4 stores not only body specifying information such as a body height and a trunk length and the above expressions 1 to 15 but also appropriate messages for health guideline advice.

An impedance measuring section comprises electrodes 200 that comprise current applying electrodes 13 (13R, 13L) for applying a current to a body part to be measured of a subject and voltage measuring electrodes 14 (14R, 14L) for measuring a potential difference in a body part to be measured of a subject, a current source 12 for supplying a current to the current applying electrodes 13, an electrode selecting section 20 for selecting electrodes to be used as the current applying electrodes 13 and electrodes to be used as the voltage measuring electrodes 14 from the electrodes 200, a difference amplifier 23 for amplifying a potential difference measured by the voltage measuring electrodes 14, a bandpass filter 24 for filtering, a detecting section 25, an amplifier 26, and an A/D converter 27.

The electrodes 200 may be implemented by metal-plating the surfaces of an SUS material and a resin material, as in the case of the current applying electrodes 13R and 13L and the voltage measuring electrodes 14R and 14L in the first embodiment.

The electrode selecting section 20 is connected between the electrodes 200 (current applying electrodes 13 and voltage measuring electrodes 14) and the difference amplifier 23 and the current source 12 and selects electrodes to be used as the current applying electrodes 13 (13R, 13L) from the electrodes 200 and connects the electrodes to the current source 12 and selects electrodes to be used as the voltage measuring electrodes 14 (14R, 14L) from the electrodes 200 and connects the electrodes to the difference amplifier 23. For example, as shown in FIG. 1, the electrode selecting section 20 connects electrodes such that a pair of current applying electrodes (13R, 13L) are situated in the central portions of the contact surfaces of the grip electrodes 130 and 140 and a pair of voltage measuring electrodes (14R, 14L) are situated in the upper and lower portions of the contact surfaces thereof. Further, the electrode selecting section 20 may select electrodes such that the current applying electrodes and the voltage measuring electrodes are in arrangement relationships as shown in FIGS. 14 to 18 to be described later.

The principle of the present invention is the same as that described in the first embodiment with reference to FIGS. 4 to 10, and an example of actual disposition of the electrodes is the same as that described in the first embodiment with reference to FIGS. 11 to 13. Therefore, descriptions thereof will be omitted.

According to the present invention, multiple measurements by arrangements of combinations of multiple electrode pairs are performed based on the electrode arrangement methods shown in FIGS. 11 to 13. Electrode arrangement examples for carrying out such multiple measurements will be described hereinafter.

FIGS. 41 to 45 show multiple electrode arrangement examples for measuring visceral fat tissues according to the present invention and are diagrams showing the abdomen viewed with the navel A of a subject as the center.

Figure 41:
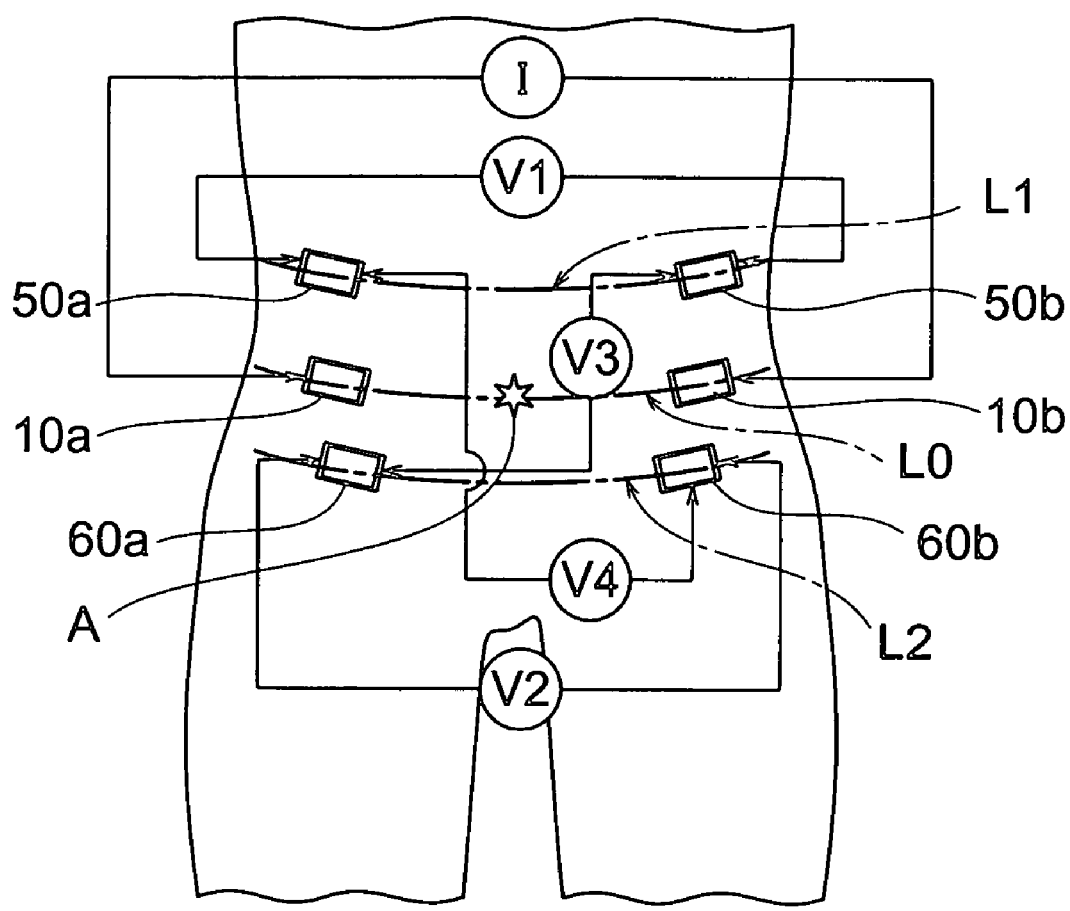
FIG. 41 is a diagram illustrating an electrode arrangement example for performing multiple measurements according to the fourth embodiment of the present invention.

(i) Multiple Measurements with Two Pairs of Voltage Measuring Electrodes for One Pair of Current Applying Electrodes In the electrode arrangement example of FIG. 41, a pair of current applying electrodes (10a, 10b) are disposed on the navel circumferential surface (L0), and two pairs of voltage measuring electrodes (50a, 50b) and (60a, 60b) are disposed on upper and lower parallel surfaces (L1, L2) which are distant from the navel circumferential surface (L0) only by a certain distance. In this arrangement example, a virtual energization route (straight route between the current applying electrodes) is situated on the navel circumferential surface (L0).

As shown in FIG. 41, when a current applied between the current applying electrodes is I and measured potential differences between the voltage measuring electrodes are V1, V2, V3 and V4, measured impedances are expressed as follows.

$Ztm1 = V1/I$ $Ztm2 = V2/I$ $Ztm3 = V3/I$ $Ztm4 = V4/I$

These impedances are averaged by the following expression.

$Ztm\text{mean} = (Ztm1 + Ztm2 + Ztm3 + Ztm4)/4$

Alternatively, they are weighted averaged by the following expression.

$Ztm\text{mean} = (n1 \times Ztm1 + n2 \times Ztm2 + n3 \times Ztm3 + n4 \times Ztm4)/\Sigma n$     expression 28 wherein n1 to n4 are weighted average constants, and $\Sigma n$ is $n1+n2+n3+n4$.

Such a weighted average process is particularly useful when a difference in the degree of contribution between body parts to be measured exists due to a difference in the internal tissue structure.

Figure 42:
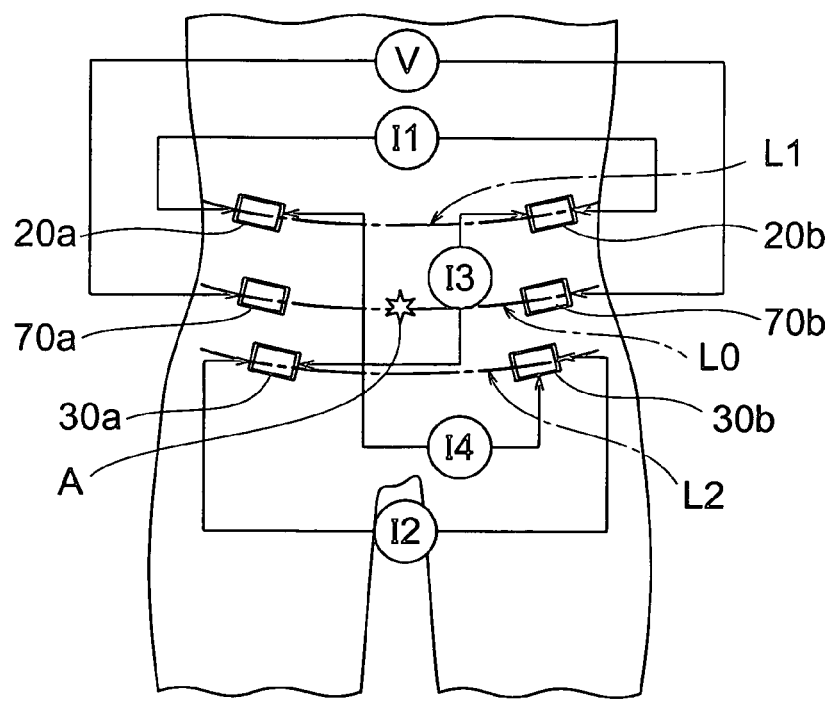
FIG. 42 is a diagram illustrating an electrode arrangement example for performing multiple measurements according to the fourth embodiment of the present invention.

(ii) Multiple Measurements with One Pair of Voltage Measuring Electrodes for Two Pairs of Current Applying Electrodes In the electrode arrangement example of FIG. 42, two pairs of current applying electrodes (20a, 20b) and (30a, 30b) are disposed on surfaces (L1, L2) parallel to the navel circumferential surface (L0), and a pair of voltage measuring electrodes (70a, 70b) are disposed on the navel circumferential surface (L0). In this arrangement example, as virtual energization routes (straight route between the current applying electrodes), virtual energization routes (energization routes of applied currents I1 and I2) on surfaces close to the navel circumferential surface in the trunk longitudinal direction and virtual energization routes (energization routes of applied currents I3 and I4) on energization surfaces crossing the navel circumferential surface diagonally are combined.

As shown in FIG. 42, when currents applied between the current applying electrodes are I1, I2, I3 and I4 and a measured potential difference between the voltage measuring electrodes is V, measured impedances are expressed as follows.

$$Ztm1=V/I1$$

$$Ztm2=V/I2$$

$$Ztm3=V/I3$$

$$Ztm4=V/I4$$

These impedances are averaged by the following expression.

$$Ztm\text{mean}=(Ztm1+Ztm2+Ztm3+Ztm4)/4$$

Alternatively, they are weighted averaged by the following expression.

$$Ztm\text{mean}=(n1\times Ztm1+n2\times Ztm2+n3\times Ztm3+n4\times Ztm4)/\Sigma n$$

wherein n1 to n4 are weighted average constants, and $\Sigma n$ is n1+n2+n3+n4.

Figure 43:
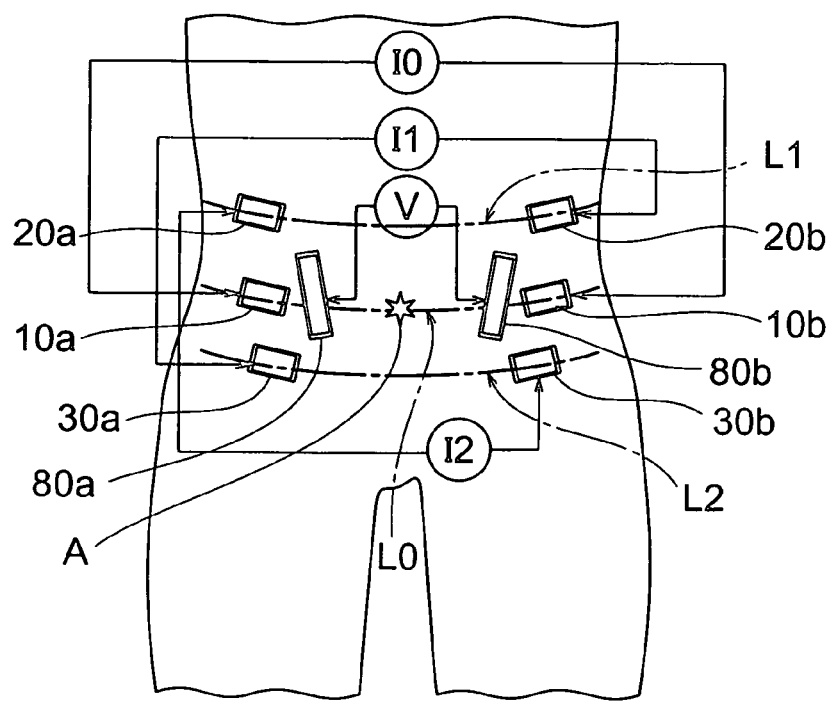
FIG. 43 is a diagram illustrating an electrode arrangement example for performing multiple measurements according to the fourth embodiment of the present invention.

(iii) Multiple Measurements with One Pair of Voltage Measuring Electrodes for Three Pairs of Current Applying Electrodes In the electrode arrangement example of FIG. 43, three pairs of current applying electrodes (10a, 10b), (20a, 20b) and (30a, 30b) are disposed on the navel circumferential surface (L0) and surfaces (L1, L2) parallel to the circumferential surface, and a pair of voltage measuring electrodes (80a, 80b) are disposed on the navel circumferential surface (L0). In this arrangement example, as virtual energization routes (straight route between the current applying electrodes), a virtual energization route (energization route of applied current I0) on the navel circumferential surface and virtual energization routes (energization routes of applied currents I1 and I2) on energization surfaces crossing the navel circumferential surface diagonally are combined.

As shown in FIG. 43, when currents applied between the current applying electrodes are I0, I1 and I2 and a measured potential difference between the voltage measuring electrodes is V, measured impedances are expressed as follows.

$$Ztm0=V/I0$$

$$Ztm1=V/I1$$

$$Ztm2=V/I2$$

These impedances are averaged by the following expression.

$$Ztm\text{mean}=(Ztm0+Ztm1+Ztm2)/3$$

Alternatively, they are weighted averaged by the following expression.

$$Ztm\text{mean}=(n0\times Ztm0+n1\times Ztm1+n2\times Ztm2)/\Sigma n$$

wherein n1 to n3 are weighted average constants, and $\Sigma n$ is n1+n2+n3.

(iv) Multiple Measurements with Electrodes Shared as Current Applying Electrodes and Voltage Measuring Electrodes In this measurement, sharing of six electrodes as shown in FIG. 1 can be implemented by switching between the functions of current applying electrodes and voltage measuring electrodes, and multiple measurements are implemented by a minimum number of electrodes. This switching of the functions of the electrodes is performed by the electrode selecting section 20 as described above.

Figure 44:
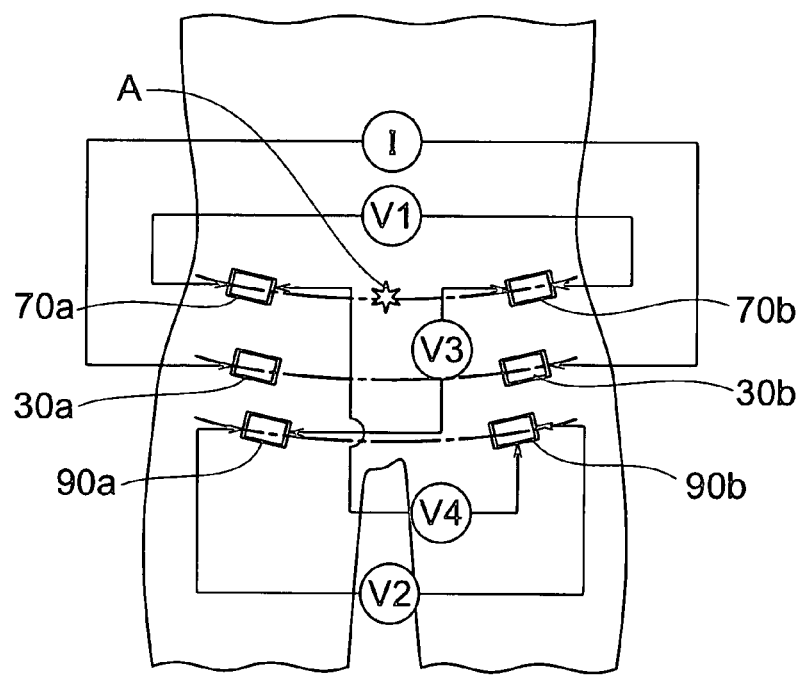
FIG. 44 is a diagram illustrating an electrode arrangement example for performing multiple measurements according to the fourth embodiment of the present invention.
Figure 45:
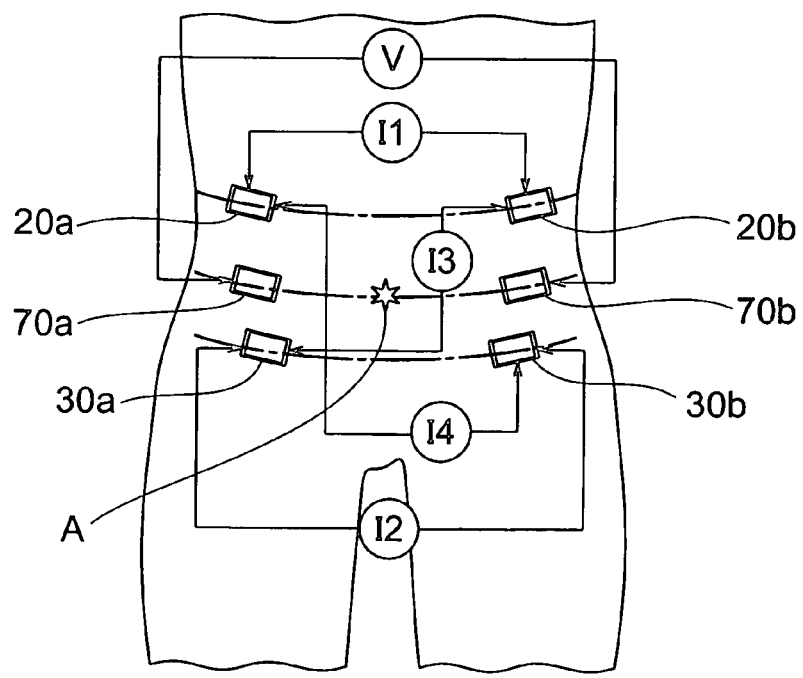
FIG. 45 is a diagram illustrating an electrode arrangement example for performing multiple measurements according to the fourth embodiment of the present invention.

FIG. 44 is an electrode arrangement example in multiple measurements with two pairs of voltage measuring electrodes for a pair of current applying electrodes, and as in the above measurements (i), two pairs of voltage measuring electrodes (70a, 70b) and (90a, 90b) are disposed on the navel circumferential surface or a circumferential surface parallel to the navel circumferential surface with a pair of current applying electrodes (30a, 30b) situated between the pairs. Meanwhile, FIG. 45 is an electrode arrangement example in multiple measurements with one pair of voltage measuring electrodes for two pairs of current applying electrodes, and as in the above measurements (ii), two pairs of current applying electrodes (20a, 20b) and (30a, 30b) are disposed on the navel circumferential surface or a circumferential surface parallel to the navel circumferential surface with a pair of voltage measuring electrodes (70a, 70b) situated between the pairs.

In this case, the above electrodes are connected to the electrode selecting section 20. This electrode selecting section 20 switches between the functions of the voltage measuring electrodes and the current applying electrodes. When they are used as the voltage measuring electrodes, they are connected to the difference amplifier 23, while when they are used as the current applying electrodes, they are connected to the current source 12. By such operations, the electrodes are shared as current applying electrode pairs and voltage measuring electrode pairs. For example, a pair of current applying electrodes (30a, 30b) in FIG. 44 are switched to a pair of voltage measuring electrodes (70a, 70b) in FIG. 45, and two pairs of voltage measuring electrodes (70a, 70b) and (90a, 90b) in FIG. 44 are switched to two pairs of current applying electrodes (20a, 20b) and (30a, 30b) in FIG. 45.

The operations of the trunk visceral fat measuring apparatus according to the fourth embodiment are the same as those illustrated in FIGS. 14 to 17 of the first embodiment except for the trunk impedance measurement process in STEP S6 illustrated in FIG. 1. Since there are some differences with respect to the trunk impedance measurement process, only this process will be described with reference to FIG. 46 hereinafter.

Figure 46:
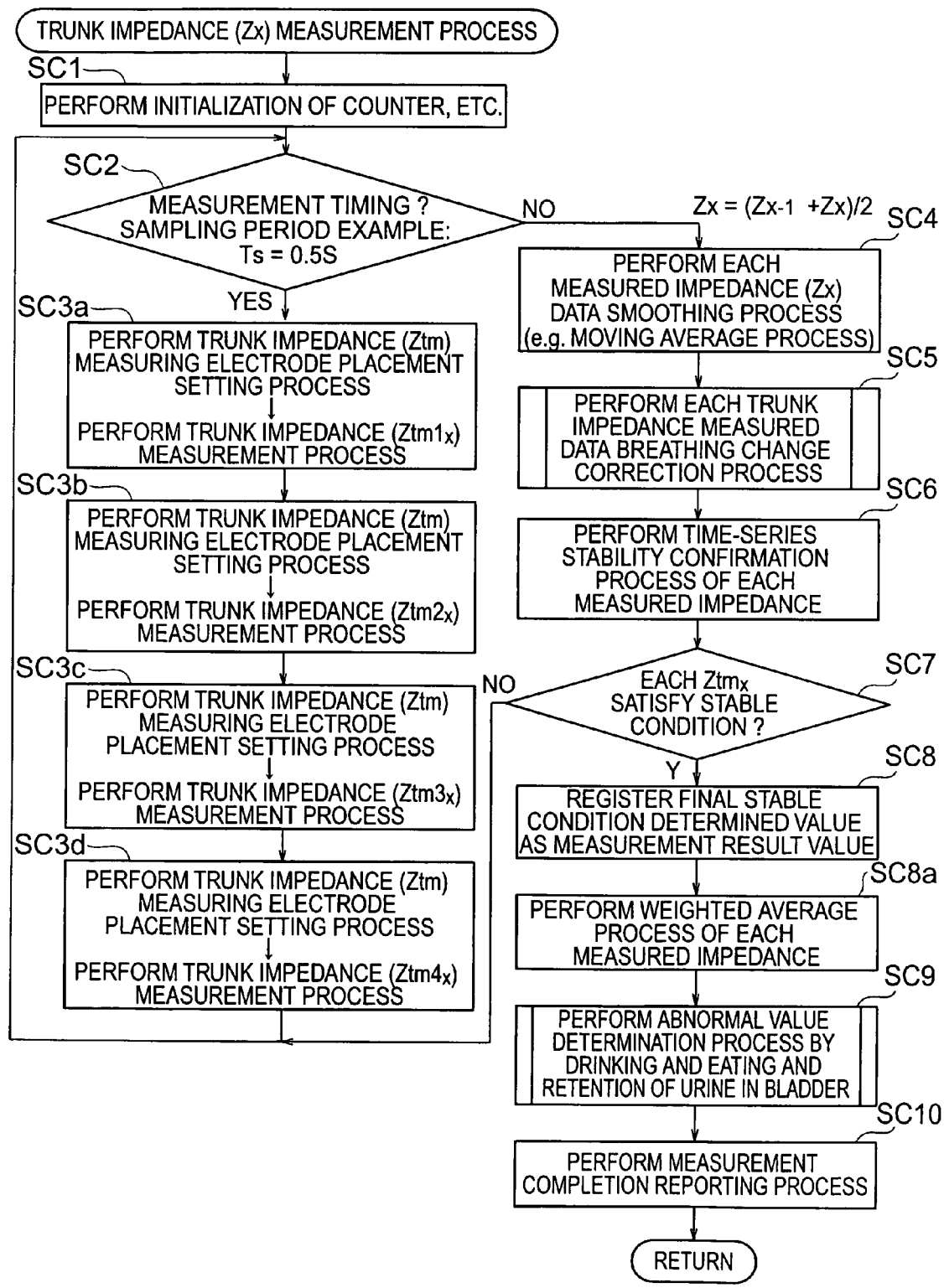
FIG. 46 is a diagram illustrating the process flow of measurement of the impedance of the trunk as a subroutine of the basic flow.

FIG. 46 is a diagram corresponding to FIG. 18 of the first embodiment and is used in place of this FIG. 18. In this embodiment, "process of removing influence of change by breathing" and "process of determining abnormal value by drinking and eating and retention of water (e.g. urine) in bladder or the like" as described in (12) and (13) in the above 7. are conducted. Firstly, in STEP SC1, the computation/control section 21 initializes a counter, for example, the number of samples for measurement data of the impedance Ztm of the trunk, and a flag F, based on an instruction from the operation section 51 or the like. The flag F takes "1" or "0".

Then, in STEP SC2, the computation/control section 21 determines whether it is measurement timing. When it has been determined that it is measurement timing, the computation/control section 21 performs a trunk impedance (Ztm) measuring electrode placement setting process and a trunk impedance ($Ztm_x$) measurement process in STEPS SC3a to SC3d. In this subroutine flowchart, a case where four measured values are obtained as in the electrode arrangement example shown in FIG. 14 or 15 is assumed, and in this case, the computation/control section 21 measures trunk impedances ($Ztm1_x$, $Ztm2_x$, $Ztm3_x$, $Ztm4_x$) in turn.

Meanwhile, when it has been determined in STEP SC2 that it is not measurement timing, the computation/control section 21 proceeds to STEP SC4 and performs a measured impedance (Zx) data smoothing process (e.g. a moving average process). Then, in STEP SC5, the trunk impedance measured data breathing change correction process described in the first embodiment with reference to FIG. 19 is performed.

Then, in STEP SC6, the computation/control section 21 performs a time-series stability confirmation process of measured impedance of each body part. This is carried out by determining whether each value after the trunk impedance measured data breathing change correction process in STEP SC5 has converged to a value within a predetermined change in a predetermined number of times. In STEP SC7, the computation/control section 21 determines whether the measured $Ztm_x$ satisfies a stable condition. This determination is made such that a median breathing value is determined at the point when a median breathing value in each breathing cycle enters a stable range within a predetermined number of times. When it is determined in this STEP SC7 that the stable condition is satisfied, the computation/control section 21 proceeds to STEP SC8 and registers the impedance value of the determined median value as the impedance value of the trunk and a final stable condition determined value as a measurement result value in the storage section 4. Meanwhile, when it is determined in STEP SC7 that the stable condition is not satisfied, the computation/control section 21 returns to STEP SC2 and repeats the above processes.

Subsequent to STEP SC8, the computation/control section 21 performs a weighted average process of each measured impedance in STEP SC8a. This weighted average process is performed by use of the registered measurement result values (Ztm1, Ztm2, Ztm3, Ztm4) and the above expression 28.

Figure 20:
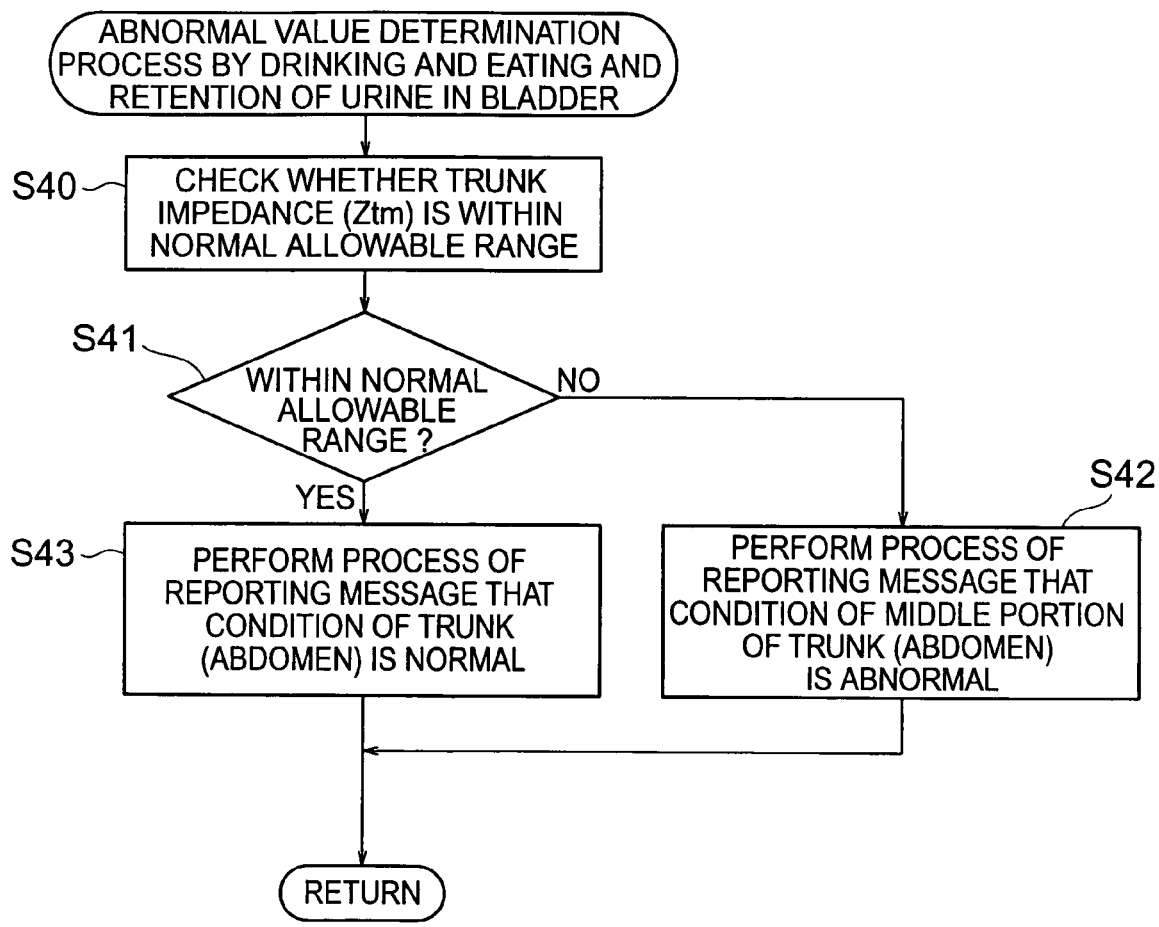
FIG. 20 is a diagram illustrating the process flow of determination of abnormal value by drinking and eating and retention of urine in the bladder as a subroutine of the trunk impedance measurement process flow of FIG. 18.

Subsequent to STEP SC8a, the computation/control section 21 performs the abnormal value determination process by drinking and eating and retention of urine in bladder which has been described in the first embodiment with reference to FIG. 20 in STEP SC9 and informs completion of measurements by means of the alarming buzzer 22 (refer to FIG. 2), thereby completing measurements, in STEP SC10.

FIG. 47 shows a variation of the trunk visceral fat measuring apparatus according to the fourth embodiment of the present invention. An apparatus 1C' in this variation corresponds to the apparatus 1' described in the first embodiment with reference to FIG. 21. The apparatus 1C' comprises electrodes and a main unit which are integrated and is used such that the whole apparatus is pressed against the abdomen like a belt. Unlike the example of FIG. 28, a main unit 60 in FIG. 47 is connected directly to left and right grip electrode sections 62R and 62L by joints 55. The joints 55 are formed of a rubber material or a resin material so as to be movable as indicated by the arrow. The grip electrode sections 62R and 62L have a plurality of electrodes 80L and 80R. These electrodes may be movable and adjustable as indicated by the arrow (refer to electrode 35). Further, the grip electrode sections 62R and 62L have positioning guides 84R and 84L. Further, the main unit 60 has a display section 64. Although not particularly shown, it is also possible in this variation to place the display section on the front side as in FIG. 27.

What is claimed is:

1. A trunk visceral fat measuring method comprising steps of:

applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and determining the visceral fat tissue amount of the trunk by use of impedance of the trunk which has been obtained by use of the potential difference wherein:

one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween, the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween, the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction, and the method further comprises:

determining a trunk skeletal muscle tissue volume based on body specifying information;

determining impedance of trunk skeletal muscle tissue layer based on the determined trunk skeletal muscle tissue volume and the body specifying information;

determining a splanchnic organ tissue volume of the trunk based on the body specifying information;

determining impedance of the splanchnic organ tissue of the trunk based on the determined splanchnic organ tissue volume of the trunk and the body specifying information;

determining impedance of the visceral fat tissue of the trunk based on the determined impedance of the trunk, the determined impedance of the trunk skeletal muscle tissue layer and the determined impedance of the splanchnic organ tissue of the trunk; and determining the visceral fat tissue amount of the trunk based on the determined impedance of the visceral fat tissue of the trunk and body specifying information.

2. The trunk visceral fat measuring method of claim 1, wherein the step of determining the impedance of the visceral fat tissue of the trunk based on the impedance of the trunk, the determined impedance of the trunk skeletal muscle tissue layer and the impedance of the splanchnic organ tissue of the trunk is characterized by an electrical equivalent circuit of the trunk in which the impedance of the trunk skeletal muscle tissue layer is connected in parallel to a series circuit of the impedance of the splanchnic organ tissue of the trunk and the impedance of the trunk visceral fat tissue.

3. A trunk visceral fat measuring method comprising steps of:
applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and
determining the visceral fat tissue amount of the trunk by use of impedance of the trunk which has been obtained by use of the potential difference, wherein:
one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween,
the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween,
the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction,
in the step of applying a current from a pair of current applying electrodes, the current is applied at a first frequency and a second frequency which is higher than the first frequency, and
the method further comprises:
determining impedance of a skeletal muscle tissue layer of the trunk based on the measured impedance of the trunk;
determining a splanchnic organ tissue volume of the trunk based on body specifying information;
determining impedance of splanchnic organ tissues of the trunk based on the determined splanchnic organ tissue volume of the trunk and the body specifying information;
determining impedance of visceral fat tissues of the trunk based on the measured impedance of the trunk, the determined impedance of the skeletal muscle tissue layer of the trunk and the determined impedance of the splanchnic organ tissues of the trunk; and
determining the visceral fat tissue amount of the trunk based on the determined impedance of the visceral fat tissues of the trunk and the body specifying information.

4. A trunk visceral fat measuring method comprising steps of:
applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and
determining the visceral fat tissue amount of the trunk by use of impedance of the trunk which has been obtained by use of the potential difference, wherein:
one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween,
the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween,
the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction,
in the step of applying a current from a pair of current applying electrodes, the current is applied at a first frequency and a second frequency which is higher than the first frequency, and
the method further comprises:
determining a splanchnic organ tissue volume of the trunk based on body specifying information;
determining impedance of splanchnic organ tissues of the trunk based on the determined splanchnic organ tissue volume of the trunk and the body specifying information;
determining impedance of visceral fat tissues of the trunk based on the measured impedance of the trunk and the determined impedance of the splanchnic organ tissues of the trunk; and
determining the visceral fat tissue amount of the trunk based on the determined impedance of the visceral fat tissues of the trunk and the body specifying information.

5. The trunk visceral fat measuring method of claim 3 or 4, wherein the step of determining the impedance of the visceral fat tissues of the trunk is characterized by an electrical equivalent circuit of the trunk in which the impedance of the trunk skeletal muscle tissue layer is connected in parallel to a series circuit of the impedance of the splanchnic organ tissues of the trunk and the impedance of the trunk visceral fat tissues.

6. The trunk visceral fat measuring method of claim 3 or 4, wherein the step of determining the impedance of the visceral fat tissues of the trunk is characterized by an electrical equivalent circuit of the trunk in which each of the impedance of the subcutaneous fat tissue layer of the trunk and the impedance of the trunk skeletal muscle tissue layer is connected in parallel to a series circuit of the impedance of the splanchnic organ tissues of the trunk and the impedance of the trunk visceral fat tissues.

7. A trunk visceral fat measuring method comprising steps of:
applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and determining the visceral fat tissue amount of the trunk by use of impedance of the trunk which has been obtained by use of the potential difference, wherein:

one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween, the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween, the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction, in the step of applying a current from a pair of current applying electrodes, the current is applied at a first frequency and a second frequency which is higher than the first frequency, and the method further comprises:
  determining impedance of a skeletal muscle tissue layer of the trunk based on the measured impedance of the trunk;
  determining a subcutaneous fat tissue volume of the trunk based on body specifying information;
  determining impedance of a subcutaneous fat tissue layer of the trunk based on the determined subcutaneous fat tissue volume of the trunk and the body specifying information;
  determining a splanchnic organ tissue volume of the trunk based on body specifying information;
  determining impedance of splanchnic organ tissues of the trunk based on the determined splanchnic organ tissue volume of the trunk and the body specifying information;
  determining impedance of visceral fat tissues of the trunk based on the measured impedance of the trunk, the determined impedance of the skeletal muscle tissue layer of the trunk, the determined impedance of the subcutaneous fat tissue layer of the trunk and the determined impedance of the splanchnic organ tissues of the trunk; and
  determining the visceral fat tissue amount of the trunk based on the determined impedance of the visceral fat tissues of the trunk and body specifying information.

8. A trunk visceral fat measuring method comprising steps of:
applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and
determining the visceral fat tissue amount of the trunk by use of impedance of the trunk which has been obtained by use of the potential difference, wherein:

one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween, the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween, the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction, in the step of applying a current from a pair of current applying electrodes, the current is applied at a first frequency and a second frequency which is higher than the first frequency, and the method further comprises:
  determining a subcutaneous fat tissue volume of the trunk based on body specifying information;
  determining impedance of a subcutaneous fat tissue layer of the trunk based on the determined subcutaneous fat tissue volume of the trunk and the body specifying information;
  determining a splanchnic organ tissue volume of the trunk based on the body specifying information;
  determining impedance of splanchnic organ tissues of the trunk based on the determined splanchnic organ tissue volume of the trunk and the body specifying information;
  determining impedance of visceral fat tissues of the trunk based on the measured impedance of the trunk, the determined impedance of the subcutaneous fat tissue layer of the trunk and the determined impedance of the splanchnic organ tissues of the trunk; and
  determining the visceral fat tissue amount of the trunk based on the determined impedance of the visceral fat tissues of the trunk and the body specifying information.

9. A trunk visceral fat measuring method comprising steps of:
applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and
determining the visceral fat tissue amount of the trunk by use of impedance of the trunk which has been obtained by use of the potential difference, wherein:

one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween, the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween, the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction, a current is applied from one current applying electrode included in at least one current applying electrode pair to a body part which is a section between the navel and the upper border of the iliac crest or aponeurosis between the rectus abdominis muscle and the external abdominal oblique muscle, one voltage measuring electrode included in one voltage measuring electrode pair out of at least two voltage measuring electrode pairs is disposed at a position where the influence of spreading resistance right underneath the current applying electrode is predominant, the other voltage measuring electrode is disposed at a remote position where influence of spreading resistance right underneath the current applying electrode is weak to measure a potential difference between the voltage measuring electrodes so as to obtain subcutaneous fat tissue information, the other voltage measuring electrode pair out of at least two voltage measuring electrode pairs are disposed at a remote position where the influence of the spreading resistance right underneath the current applying electrode is weak to measure a voltage so as to obtain visceral fat tissue information, the one voltage measuring electrode pair and the other voltage measuring electrode pair are selected to obtain the subcutaneous fat tissue layer information and the visceral fat tissue information selectively, a subcutaneous fat tissue volume of the trunk is determined based on the impedance of the trunk which has been determined by use of the potential difference measured by the above one voltage measuring electrode pair and body specifying information, impedance of a trunk subcutaneous fat tissue layer is determined based on the determined subcutaneous fat tissue volume of the trunk and the body specifying information, a skeletal muscle tissue volume of the trunk is determined based on the body specifying information, impedance of a skeletal muscle tissue layer is determined based on the determined skeletal muscle tissue volume of the trunk and the body specifying information, a splanchnic organ tissue volume of the trunk is determined based on the body specifying information, impedance of splanchnic organ tissues of the trunk is determined based on the determined splanchnic organ tissue volume of the trunk and the body specifying information, impedance of the visceral fat tissues of the trunk is determined based on the impedance of the trunk which has been determined by use of the potential difference measured by the above other voltage measuring electrode pair, the determined impedance of the subcutaneous fat tissue layer of the trunk, the determined impedance of the skeletal muscle tissue layer of the trunk and the determined impedance of the splanchnic organ tissues of the trunk, and the visceral fat tissue amount of the trunk is determined based on the determined impedance of the visceral fat tissues of the trunk and the body specifying information.

10. The method described in claim 9, wherein the step of determining the impedance of the visceral fat tissues of the trunk based on the impedance of the trunk, the determined impedance of the skeletal muscle tissue layer of the trunk and the impedance of the splanchnic organ tissues of the trunk is characterized by an electrical equivalent circuit of the trunk in which the impedance of the skeletal muscle tissue layer of the trunk is connected in parallel to a series circuit of the impedance of the splanchnic organ tissues of the trunk and the impedance of the visceral fat tissues of the trunk.

11. The method described in claim 9, wherein the step of determining the impedance of the visceral fat tissues of the trunk based on the impedance of the trunk, the determined impedance of the skeletal muscle tissue layer of the trunk and the impedance of the splanchnic organ tissues of the trunk is characterized by an electrical equivalent circuit of the trunk in which each of the impedance of the skeletal muscle tissue layer of the trunk and the impedance of the subcutaneous fat tissue layer of the trunk is connected in parallel to a series circuit of the impedance of the splanchnic organ tissues of the trunk and the impedance of the visceral fat tissues of the trunk.

12. A trunk visceral fat measuring method comprising steps of:

applying a current from a pair of current applying electrodes to a section between the navel and the upper border of the iliac crest or aponeurosis between the rectus abdominis muscle and the external abdominal oblique muscle; measuring a potential difference which has occurred in the tissue through which the current has passed by a pair of voltage measuring electrodes; and determining the visceral fat tissue amount of the trunk by use of impedance of the trunk which has been obtained by use of the potential difference, wherein:

one of the current applying electrodes and one of the voltage measuring electrodes are disposed at a section between the navel and the upper border of the iliac crest or aponeurosis between the rectus abdominis muscle and the external abdominal oblique muscle positioned at either the left side or the right side when viewed, in the trunk circumferential direction, with the navel as the center therebetween, the other current applying electrode and the other voltage measuring electrodes are disposed at a section between the navel and the upper border of the iliac crest or aponeurosis between the rectus abdominis muscle and the external abdominal oblique muscle positioned at the other side when viewed, in the trunk circumferential direction, with the navel as the center therebetween, the pair of current applying electrodes and the pair of voltage measuring electrodes are disposed at a section between the navel and the upper border of the iliac crest or aponeurosis between the rectus abdominis muscle and the external abdominal oblique muscle, these pairs being positioned away from each other in a trunk length direction, at least one pair of current applying electrodes or at least one pair of voltage measuring electrodes are further disposed on the navel circumferential surface or at a position distant from the navel circumferential surface in the trunk longitudinal direction by a certain distance, internal tissue information around the navel is measured in turn by a combination of the current applying electrode pair and the electrode pair, the impedance of the trunk is measured by processing the measured information, the impedance of the trunk is measured, impedance of skeletal muscle tissue layer of the trunk is determined based on body specifying information, impedance of splanchnic organ tissues of the trunk is determined based on the body specifying information, impedance of visceral fat tissues of the trunk is determined based on the measured impedance of the trunk, the determined impedance of the skeletal muscle tissue layer of the trunk and the determined impedance of the splanchnic organ tissues of the trunk, and the visceral fat tissue volume of the trunk is determined based on the determined impedance of the visceral fat tissues of the trunk and the body specifying information.

13. The method described in claim 12, wherein the impedance of the skeletal muscle tissue layer of the trunk is determined based on the skeletal muscle tissue volume of the trunk which has been determined based on body specifying information and body specifying information, and the impedance of the splanchnic organ tissues of the trunk is determined based on the splanchnic organ tissue volume of the trunk which has been determined based on body specifying information and body specifying information.

14. The method described in claim 12 or 13, wherein the step of determining the impedance of the visceral fat tissues of the trunk based on the impedance of the trunk, the determined impedance of the skeletal muscle tissue layer of the trunk and the impedance of the splanchnic organ tissues of the trunk is characterized by an electrical equivalent circuit of the trunk in which the impedance of the skeletal muscle tissue layer of the trunk is connected in parallel to a series circuit of the impedance of the splanchnic organ tissues of the trunk and the impedance of the visceral fat tissues of the trunk.

* * * * *